US008809625B2

(12) United States Patent
Herrmann et al.

(10) Patent No.: US 8,809,625 B2
(45) Date of Patent: Aug. 19, 2014

(54) **COMPOSITIONS AND METHODS FOR THE SUPPRESSION OF TARGET POLYNUCLEOTIDES FROM *LYGUS***

(75) Inventors: Rafael Herrmann, Wilmington, DE (US); Michael Lassner, Urbandale, IA (US); Albert L. Lu, Newark, DE (US); Mark E. Nelson, Newark, DE (US); James K. Presnail, Avondale, PA (US); Janet A. Rice, Wilmington, DE (US)

(73) Assignees: Pioneer Hi-Bred International, Inc., Johnston, IA (US); E.I. Du Pont de Nemours and Company, Wilmington, DE (US)

( * ) Notice: Subject to any disclaimer, the term of this patent is extended or adjusted under 35 U.S.C. 154(b) by 1485 days.

(21) Appl. No.: 12/351,379

(22) Filed: Jan. 9, 2009

(65) Prior Publication Data
US 2009/0192117 A1 Jul. 30, 2009

Related U.S. Application Data

(60) Provisional application No. 61/021,685, filed on Jan. 17, 2008, provisional application No. 61/021,676, filed on Jan. 17, 2008.

(51) Int. Cl.
*C12N 15/82* (2006.01)
*C12N 15/87* (2006.01)
*A01H 1/00* (2006.01)

(52) U.S. Cl.
USPC ............ 800/285; 800/286; 800/278; 800/288

(58) Field of Classification Search
None
See application file for complete search history.

(56) References Cited

U.S. PATENT DOCUMENTS

| 2003/0150017 A1 | 8/2003 | Mesa et al. |
| 2005/0095199 A1 | 5/2005 | Whyard et al. |
| 2006/0021087 A1 | 1/2006 | Baum et al. |
| 2006/0075515 A1 | 4/2006 | Luethy et al. |
| 2006/0200878 A1 | 9/2006 | Lutfiyya et al. |
| 2006/0272049 A1 | 11/2006 | Waterhouse et al. |
| 2007/0199100 A1 | 8/2007 | Michaeli et al. |

FOREIGN PATENT DOCUMENTS

| EP | 1 818 405 A3 | 8/2007 |
| WO | WO 01/34815 A | 5/2001 |
| WO | WO 01/37654 A2 | 5/2001 |
| WO | WO 02/00904 A | 1/2002 |
| WO | WO 03/052110 A2 | 6/2003 |
| WO | WO 2005/049841 A1 | 6/2005 |
| WO | WO 2005/077116 A | 8/2005 |
| WO | WO 2005/110068 A2 | 11/2005 |
| WO | WO 2006/044480 A2 | 4/2006 |
| WO | WO 2006/045590 A2 | 5/2006 |
| WO | WO 2006/047495 A | 5/2006 |
| WO | WO 2007/003023 A | 1/2007 |
| WO | WO 2007/087153 A2 | 8/2007 |
| WO | WO 2007/095469 A2 | 8/2007 |

OTHER PUBLICATIONS

Mueller et al. 2005, Genbank Accession No. DU884652.*
Agrawal, N., et al., "siRNA-Directed Silencing of Transgene Expressed in Cultured Insect Cells", *Biochemical and Biophysical Research Communications*, 2004, pp. 428-434, vol. 320, No. 2, Elsevier Science Publishers Ltd., United Kingdom.
Atkinson, H. J., et al., "Engineering Plants for Nematode Resistance," *Ann. Rev. Phytopathol*, 2003, pp. 615-639, vol. 41.
Bakhetia, M., et al., "RNA Interference and Plant Parasitic Nematodes," *Trends in Plant Science*, 2005, pp. 362-367, vol. 10, No. 8, Elsevier Science Publishers Ltd., United Kingdom.
Boutla, A., et al., "Induction of RNA Interference in *Caenorhabditis elegans* by RNAs Derived From Plants Exhibiting Post-Transcriptional Gene Silencing", *Nucleic Acids Research*, 2002, pp. 1688-1694, vol. 30, No. 7.
Gao, B., et al., "The Parasitome of the Phytonematode *Heterodera glycines*,", *Molecular Plant-Microbe Interactions*, 2003, pp. 720-726, vol. 16, No. 8, APS Press, USA.
Gao, B., et al., "Identification of Putative Parasitism Genes Expressed in the Esophageal Gland Cells of the Soybean Cyst Nematode *Heterodera glycines*," *Molecular Plant-Microbe Interactions*, 2001, pp. 1247-1254, vol. 14., No. 10, APS Press, USA.
Urwin, P. E., et al., "Ingeston of Double-Stranded RNA by Preparasitic Juvenile Cyst Nematodes Leads to RNA Interference," *Molecular Plant-Microbe Interactions*, 2002, pp. 747-752, vol. 15, No. 8.
Zhu, Y. C., et al., Enhanced Esterase Gene Expression and Activity in a Malathion-Resistant Strain of the Tarnished Plant Bug, *Lygus lineolaris, Insect Biochemistry and Molecular Biology*, 2004, pp. 1175-1186, vol. 34, Elsevier Science Publishers Ltd., United Kingdom.
Zhu, Y. C., et al., Comparative Study on Glutathione S-Transferase Activity, cDNA, and Gene Expression Between Malathion Susceptible and Resistant Strains of the Tarnished Plant Bug, *Lygus lineolaris*, 2006, *Pesticide Biochemistry and Physiology*, pp. 62-72, vol. 87, Elsevier Science Publishers Ltd., United Kingdom.
Database EMBL [online]: Database Access No. DY786966.

* cited by examiner

*Primary Examiner* — Li Zheng
(74) *Attorney, Agent, or Firm* — Pioneer Hi Bred Int'l, Inc.

(57) ABSTRACT

Methods and compositions are provided which employ a silencing element that, when ingested by a pest, such as a pest from the *Lygus* genus, is capable of decreasing the expression of a target sequence in the pest. In specific embodiments, the decrease in expression of the target sequence controls the pest and thereby the methods and compositions are capable of limiting damage to a plant. The present invention provides various target polynucleotides from specific polypeptide families as disclosed herein, or active variants thereof, wherein a decrease in expression of one or more the sequences in the target pest controls the pest. Further provided are silencing elements which when ingested by the pest decrease the level of the target polypeptide and thereby control the pest. Plants, plant parts, bacteria and other host cells comprising the silencing elements or an active variant or fragment thereof of the invention are also provided.

23 Claims, No Drawings

COMPOSITIONS AND METHODS FOR THE SUPPRESSION OF TARGET POLYNUCLEOTIDES FROM *LYGUS*

CROSS-REFERENCE TO RELATED APPLICATIONS

This application claims priority to U.S. Provisional Application No. 61/021,685, filed Jan. 17, 2008 and U.S. Provisional Application No. 61/021,676; filed Jan. 17, 2008; both of which are herein incorporated by reference in their entirety.

FIELD OF THE INVENTION

The present invention relates generally to methods of molecular biology and gene silencing to control pests.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 366630seqlist.txt, a creation date of Dec. 23, 2008, and a size of 50 Kb. The sequence listing filed via EFS-Web is part of the specification and is hereby incorporated in its entirety by reference herein.

BACKGROUND OF THE INVENTION

Insect pests are a serious problem in agriculture. They destroy millions of acres of staple crops such as corn, soybeans, peas, and cotton. Yearly, these pests cause over $100 billion dollars in crop damage in the U.S. alone. In an ongoing seasonal battle, farmers must apply billions of gallons of synthetic pesticides to combat these pests. Other methods employed in the past delivered insecticidal activity by microorganisms or genes derived from microorganisms expressed in transgenic plants. For example, certain species of microorganisms of the genus *Bacillus* are known to possess pesticidal activity against a broad range of insect pests including Lepidoptera, Diptera, Coleoptera, Hemiptera, and others. In fact, microbial pesticides, particularly those obtained from *Bacillus* strains, have played an important role in agriculture as alternatives to chemical pest control. Agricultural scientists have developed crop plants with enhanced insect resistance by genetically engineering crop plants to produce insecticidal proteins from *Bacillus*. For example, corn and cotton plants genetically engineered to produce Cry toxins (see, e.g., Aronson (2002) *Cell Mol. Life Sci.* 59(3):417-425; Schnepf et al. (1998) *Microbiol. Mol. Biol. Rev.* 62(3):775-806) are now widely used in American agriculture and have provided the farmer with an alternative to traditional insect-control methods. However, these Bt insecticidal proteins only protect plants from a relatively narrow range of pests. Moreover, these modes of insecticidal activity provided varying levels of specificity and, in some cases, caused significant environmental consequences. Thus, there is an immediate need for alternative methods to control pests.

BRIEF SUMMARY OF THE INVENTION

Methods and compositions are provided which employ a silencing element that, when ingested by a pest, such as a pest from the *Lygus* genus, is capable of decreasing the expression of a target sequence in the pest. In specific embodiments, the decrease in expression of the target sequence controls the pest and thereby the methods and compositions are capable of limiting damage to a plant. The present invention provides various target polynucleotides from specific polypeptide families as disclosed herein, and further provides various target polynucleotides set forth in SEQ ID NOS:1-21 or active variants or fragments thereof, wherein a decrease in expression of one or more of the sequences in the target pest controls the pest (i.e., has insecticidal activity). Further provided are silencing elements, which when ingested by the pest, decrease the level of expression of one or more of the target polynucleotides. In specific embodiment, the pest that is controlled is *Lygus Hesperus*. Plants, plant parts, bacteria and other host cells comprising the silencing elements or an active variant or fragment thereof are also provided.

In another embodiment, a method for controlling a pest from the *Lygus* genus is provided. The method comprises feeding to a pest from the *Lygus* genus a composition comprising a silencing element, wherein said silencing element, when ingested by said *Lygus*, reduces the level of a target sequence in the *Lygus* and thereby controls the *Lygus*. Further provided are methods to protect a plant from *Lygus*. Such methods comprise introducing into the plant or plant part a silencing element of the invention. When the plant expressing the silencing element is ingested by the pest, the level of the target sequence is decreased and the pest is controlled.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

Methods and compositions are provided which employ a silencing element that, when ingested by a pest, such as a pest from the *Lygus* genus, is capable of decreasing the expression of a target sequence in the pest. In specific embodiments, the decrease in expression of the target sequence controls the pest and thereby the methods and compositions are capable of limiting damage to a plant or plant part. In specific embodiments, the present invention provides target polynucleotide which encode a potassium channel polypeptide, a cuticle polypeptide, an endocuticle polypeptide, a chitin binding polypeptide, a chitinase polypeptide, a hormone inducible polypeptide, a translation initiation factor, a voltage dependant channel, an EIF-related polypeptide, a polypeptide having a coiled coil helix domain, a polypeptide having a zinc finger domain, a receptor associated finger polypeptide, a lethal timorous imaginal disc polypeptide, a ribonucleoprotein, a cathepsin protease polypeptide, a polyprotein deformed destructor, and a death associated leucine rich polypeptide. The present invention provides a target polynucleotides set forth in SEQ ID NOS:1-21 or active variants and fragments thereof. Silencing elements designed in view of these target polynucleotides are provided which, when ingested by the pest, decrease the expression of one or more of the target sequences and thereby controls the pest (i.e., has insecticidal activity). These results provide the first report of insecticidal activity of dsRNA against *Lygus Hesperus*.

As used herein, by "controlling a pest" or "controls a pest" is intended any affect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack, or deterring the pests from eating the plant.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

Reducing the level of expression of the target polynucleotide or the polypeptide encoded thereby, in the pest results in the suppression, control, and/or killing the invading pathogenic organism. Reducing the level of expression of the target sequence of the pest will reduce the disease symptoms resulting from pathogen challenge by at least about 2% to at least about 6%, at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by pests from the *Lygus* genus.

Assays that measure the control of a pest are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. See, for example, Thomma et al. (1998) *Plant Biology* 95:15107-15111, herein incorporated by reference. See, also the examples below.

The invention is drawn to compositions and methods for protecting plants from a plant pest, such as pests from the Hemiptera order, or inducing resistance in a plant to a plant pest, such as pests from the Hemiptera order. The Hemiptera order comprises four suborders, the Sternorrhyncha (e.g. aphids, whiteflies), Auchenorrhyncha (e.g. cicadas, leafhoppers), Coleorrhyncha, and Heteroptera (e.g. true bugs) and about 67,500 species. Accordingly, the compositions and methods are useful in protecting plants against any member of the Hemiptera order including those of the family Cicadellidae, Membracidae, Fulgoridae, Coccidae, Aphididae, Lygaeidae, Pentatomidae, and Miridae.

In specific embodiments, the invention is drawn to compositions and methods for protecting plants from a plant pest, such as pests from the *Lygus* genus, or inducing resistance in a plant to a plant pest, such as pests from the *Lygus* genus. The *Lygus* genus comprises over 40 species of plant feeding insects in the family Miridae. As used herein, the term "*Lygus*" or "*Lygus* Bug" is used to refer to any member of the *Lygus* genus. Accordingly, the compositions and methods are also useful in protecting plants against any *Lygus* including, for example, *Lygus adspersus*, *Lygus alashanensis*, *Lygus borealis*, *Lygus elisus*, *Lygus gemellatus*, *Lygus Hesperus*, *Lygus lineolaris*, or *Lygus rugulipennis*. In particular embodiment, methods control *Lygus Hesperus*.

In other embodiments, the pest is a plant sap-sucking insect. As used herein, "plant sap-sucking insects" are insects which feed on plants using their sharp mouth parts which can be inserted into a plant to take fluid from the plant vascular system. In one embodiment, these are insects feeding directly on the fluids in the plant vascular system. In the insertion site, plant cells can also be damaged which may or may not be used as a food source by the plant sap-sucking insect. These insects are plant pests because their feeding reduces the vitality of the crop they feed on and they can transmit viral disease. Also, such sap-sucking insects can create a sugar-rich fluid named honeydew that accumulates on lower plant parts and such parts soon become covered by certain black or brown fungi known as sooty molds, hence interfering with photosynthesis.

Included in such plant sap-sucking insects are aphids or Homopteran insects of the Aphididae, and plant sap-sucking insects as used herein include but are not limited to the peach-potato aphid *Myzus persicae*, the bean aphid *Aphis fabae*, the pea aphid *Acyrthosiphumpisun*, the cabbage aphid *Brevicoryne brassicae*, the grain aphid *Sitobion avenae*, the rose-grain aphid *Metopolophium dirhodum*, the Russian wheat aphid *Diuraphis noxia* (*Mordvilko*), the English grain aphid *Macrosiphum avenae*, the greenbug aphid *Schizaphis graminum* (*Rondani*), the carrot aphid *Cavariella aegopodii*, the potato aphid *Macrosiphum euphorbiae*, the groundnut aphid *Aphiscraccivora*, the cotton aphid *Aphis gossypii*, the black citrus aphid *Toxoptera aurantii*, the brown citrus apid *Toxoptera ciidius*, the willow aphid *Cavariella* spp., the corn leaf aphid *Rhopalosiphum maidis*, the aphid *Rhopalosiphum padi*, the willow leaf aphids *Chaitophorus* spp., the black pine aphids *Cinara* spp., the Sycamore Aphid *Drepanosiphum platanoides*, the Spruce aphids *Elatobium* spp., *Aphis citricola*, *Lipaphis* as *Laodelphax striatellus* (small brown planthopper), *Nilaparvata lugens* (rice brown plant hopper) and *Sogatella furcifera* (white-backed rice planthopper), and Deltocephalidae (or leafhoppers) such as *Flexamia DeLong* spp., *Nephotettix cincticeps* and *Nephotettix virescens*, *Amrasca bigutulla*, and the potato leafhopper *Empoasca* filament. Also included are scales (also named scale insects) such as *Aonidiella aurantii* (California red scale), *Comstockaspis perniciosa* (San Jose scale), *Unaspis citri* (citrus snow scale), *Pseudaulacaspis pentagona* (white peach scale), *Saissetia oleae* (brown olive scale), *Lepidosaphes beckii* (purple scale), *Ceroplastes rubens* (red wax scale) and *Icerya purchasi* (cottonycushion scale), besides Tingidae (or lace bugs) and Psyllidae insects, and spittle bugs.

Further included as plant sap-sucking insects are Heteropteran insects and Hemipteran insects of the Auchenorrhyncha that feed from the plants' vascular system, such as sap-sucking insects of the Cicadoidea (such as Cicadas), Cercopoidea (spittlebugs or froghoppers), Membracoidea (leafhoppers and treehoppers), and Fulgoroidea (planthoppers), e.g., the cotton seed sucker bug *Dysdercus peruvianus* (Heteroptera, Pyrrhocoridae), the apple dimpling bug, *Campylomma liebknechti* (Hemiptera: Miridae) and the greenmirid, *Creontiades dilutus* which are cotton sucking insect pests, and the Lygusbugs (Hemiptera: Miridae, e.g., *Lygus hesperus*).

II. Target Sequences

As used herein, a "target sequence" comprises any sequence in the pest that one desires to decrease the level of expression. In specific embodiments, decreasing the level of the target sequence in the pest controls the pest. For instance the target sequence can be essential for growth and development. While the target sequence can be expressed in any tissue of the pest, in specific embodiments of the invention, the sequences targeted for suppression in the pest are expressed in cells of the gut tissue of the pest, cells in the midgut of the pest, and cells lining the gut lumen or the midgut. Such target sequences can be involved in gut cell metabolism, growth or differentiation.

Non-limiting examples of target sequences of the invention include a polynucleotide set forth in SEQ ID NO:1, 2, 3, 4, 5, 6, 7, 8, 9, 10, 11, 12, 13, 14, 15, 16, 17, 18, 19, 20 or 21. In specific embodiments, the silencing element comprises at least or consists of 15, 20, 22, 25 or greater consecutive nucleotides of any one of SEQ ID NO:1, 2, 3, 4, 5, 6, 7, 8, 9, 10, 11, 12, 13, 14, 15, 16, 17, 18, 19, 20, or 21. In further embodiments, the silencing element comprises or consists of at least one of the sequences set forth in SEQ ID NO: 22-408. It is recognized that such silencing elements can further comprise one or more thymine residues at the 3' end. Such residues can aid in stabilization. The element can have, for example, 1, 2, 3, 4, 5, 6 or more thymine residues at its 3' end. In further embodiments, the silencing element comprises SEQ ID NO: 23 and 24; 26 and 27; 29 and 30; 32 and 33; 35 and 36; 38 and 39; 41 and 42; 44 and 45; 47 and 48; 50 and 51; 53 and 54; 56 and 57; 59 and 60; 62 and 63; 65 and 66; 68 and 69; 71 and 72; 74 and 75; 77 and 78; 80 and 81; 83 and 84; 86 and 87; 89 and 90; 92 and 93; 95 and 96; 98 and 99; 101 and 102; 104 and 105; 107 and 108; 1 and 111; 113 and 114; 116 and 117; 119 and 120; 122 and 123; 125 and 126; 128 and 129; 131 and 132; 134 and 135; 137 and 138; 140 and 141; 143 and 144; 146 and 147; 149 and 150; 152 and 153; 155 and 156; 158 and 159; 161 and 162; 164 and 165; 167 and 168; 170 and 171; 173 and 174; 176 and 177; 179 and 180; 182 and 183; 185 and 186; 188 and 189; 191 and 192; 194 and 195; 197 and 198; 200 and 201; 203 and 204; 206 and 207; 209 and 210; 212 and 213; 215 and 216; 218 and 219; and/or 221 and 222. As exemplified elsewhere herein, decreasing the level of expression of these target sequence in *Lygus* controls the pest.

In specific embodiments, the target sequence comprises SEQ ID NO:7, 8, 9, 11, 12 or 14. In further embodiments, the silencing element comprises or consists of at least one of the sequences set forth in SEQ ID NOS:283, 284, 285, 289, 290, 291, 292, 293, 294, 304, 305, 306, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347 or 348. In still further embodiments, the silencing element comprises or consists of SEQ ID NOS: 284 and 285, 290 and 291, 293 and 294; 305 and 306; 317 and 318; 320 and 321; 323 and 324; 326 and 327; 329 and 330; 332 and 333; 335 and 336; 338 and 339; 341 and 342; 344 and 345; or 347 and 348. As exemplified elsewhere herein, expression of these sequences controls *lygus*.

III. Silencing Elements

By "silencing element" is intended a polynucleotide which when ingested by a pest, is capable of reducing or eliminating the level or expression of a target polynucleotide or the polypeptide encoded thereby. The silencing element employed can reduce or eliminate the expression level of the target sequence by influencing the level of the target RNA transcript or, alternatively, by influencing translation and thereby affecting the level of the encoded polypeptide. Methods to assay for functional silencing elements that are capable of reducing or eliminating the level of a sequence of interest are disclosed elsewhere herein. A single polynucleotide employed in the methods of the invention can comprises one or more silencing elements to the same or different target polynucleotides.

In specific embodiments, the target sequence is not a plant endogenous gene. In other embodiments, while the silencing element controls pests, preferably the silencing element has no effect on the normal plant or plant part.

As discussed in further detail below, silencing elements can include, but are not limited to, a sense suppression element, an antisense suppression element, a double stranded RNA, a miRNA, or a hairpin suppression element. Non-limiting examples of silencing elements that can employed to decrease expression of these target *Lygus* sequences comprise or consists of fragments and variants of the sense or antisense sequence of the sequence set forth in SEQ ID NO:1, 2, 3, 4, 5, 6, 7, 8, 9, 10, 11, 12, 13, 14, 15, 16, 17, 18, 19, 20, or 21 or SEQ ID NOS: 22-408. or fragments and variants of the sense or antisense sequence thereof.

In specific embodiments, the silencing element comprises or consists of at least one of the sequences set forth in SEQ ID NO: 21-408. It is recognized that such silencing elements can further comprise one or more thymine residues at the 3' end. Such residues can aid in stabilization. The element can have, for example, 1, 2, 3, 4, 5, 6 or more thymine residues at its 3' end. In further embodiments, the silencing element comprises SEQ ID NO: 23 and 24; 26 and 27; 29 and 30; 32 and 33; 35 and 36; 38 and 39; 41 and 42; 44 and 45; 47 and 48; 50 and 51; 53 and 54; 56 and 57; 59 and 60; 62 and 63; 65 and 66; 68 and 69; 71 and 72; 74 and 75; 77 and 78; 80 and 81; 83 and 84; 86 and 87; 89 and 90; 92 and 93; 95 and 96; 98 and 99; 101 and 102; 104 and 105; 107 and 108; 110 and 111; 113 and 114; 116 and 117; 119 and 120; 122 and 123; 125 and 126; 128 and 129; 131 and 132; 134 and 135; 137 and 138; 140 and 141; 143 and 144; 146 and 147; 149 and 150; 152 and 153; 155 and 156; 158 and 159; 161 and 162; 164 and 165; 167 and 168; 170 and 171; 173 and 174; 176 and 177; 179 and 180; 182 and 183; 185 and 186; 188 and 189; 191 and 192; 194 and 195; 197 and 198; 200 and 201; 203 and 204; 206 and 207; 209 and 210; 212 and 213; 215 and 216; 218 and 219; and/or 221 and 222.

In other embodiments, the silencing element comprises or consists of at least one of the sequences set forth in SEQ ID NOS:283, 284, 285, 289, 290, 291, 292, 293, 294, 304, 305, 306, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347 or 348. In still further embodiments, the silencing element comprises or consists of SEQ ID NOS: 284 and 285, 290 and 291, 293 and 294; 305 and 306; 317 and 318; 320 and 321; 323 and 324; 326 and 327; 329 and 330; 332 and 333; 335 and 336; 338 and 339; 341 and 342; 344 and 345; or 347 and 348. As exemplified elsewhere herein, expression of these sequences controls *lygus*.

By "reduces" or "reducing" the expression level of a polynucleotide or a polypeptide encoded thereby is intended to mean, the polynucleotide or polypeptide level of the target sequence is statistically lower than the polynucleotide level or polypeptide level of the same target sequence in an appropriate control pest which is not exposed to (i.e., has not ingested) the silencing element. In particular embodiments of the invention, reducing the polynucleotide level and/or the polypeptide level of the target sequence in a pest according to the invention results in less than 95%, less than 90%, less than 80%, less than 70%, less than 60%, less than 50%, less than 40%, less than 30%, less than 20%, less than 10%, or less than 5% of the polynucleotide level, or the level of the polypeptide encoded thereby, of the same target sequence in an appropriate control pest. Methods to assay for the level of the RNA transcript, the level of the encoded polypeptide, or the activity of the polynucleotide or polypeptide are discussed elsewhere herein.

i. Sense Silencing Elements

As used herein, a "sense silencing element" comprises a polynucleotide designed to express an RNA molecule corresponding to at least a part of a target messenger RNA in the "sense" orientation. Expression of the RNA molecule comprising the sense suppression element reduces or eliminates the level of the target polynucleotide or the polypeptide encoded thereby. The polynucleotide comprising the sense suppression element may correspond to all or part of the sequence of the target polynucleotide, all or part of the 5' and/or 3' untranslated region of the target polynucleotide, all or part of the coding sequence of the target polynucleotide, or all or part of both the coding sequence and the untranslated regions of the target polynucleotide.

Typically, a sense suppression element has substantial sequence identity to the target polynucleotide, optimally greater than about 65% sequence identity, more optimally greater than about 85% sequence identity, about 90%, 91%, 92%, 93%, 94%, 95%, 96%, 97%, 98% or 99% sequence identity. See, U.S. Pat. Nos. 5,283,184 and 5,034,323; herein incorporated by reference. The sense suppression element can be any length so long as it does not interfere with intron splicing and allows for the suppression of the targeted sequence. The sense suppression element can be, for example, 15, 20, 22, 25, 30, 50, 100, 150, 200, 250, 300, 350, 400, 450, 500, 600, 700, 900 or longer.

ii. Antisense Silencing Elements

As used herein, an "antisense silencing element" comprises a polynucleotide which is designed to express an RNA molecule complementary to all or part of a target messenger RNA. Expression of the antisense RNA suppression element reduces or eliminates the level of the target polynucleotide. The polynucleotide for use in antisense suppression may correspond to all or part of the complement of the sequence encoding the target polynucleotide, all or part of the complement of the 5' and/or 3' untranslated region of the target polynucleotide, all or part of the complement of the coding sequence of the target polynucleotide, or all or part of the complement of both the coding sequence and the untranslated regions of the target polynucleotide. In addition, the antisense suppression element may be fully complementary (i.e., 100% identical to the complement of the target sequence) or partially complementary (i.e., less than 100% identical to the complement of the target sequence) to the target polynucleotide. In specific embodiments, the antisense suppression element comprises at least 85%, 90%, 91%, 92%, 93%, 94%, 95%, 96%, 97%, 98%, or 99% sequence identity to the target polynucleotide. Antisense suppression may be used to inhibit the expression of multiple proteins in the same plant. See, for example, U.S. Pat. No. 5,942,657. Furthermore, the antisense suppression element can be complementary to a portion of the target polynucleotide. Generally, sequences of at least 25, 50, 100, 200, 300, 400, 450 nucleotides or greater may be used. Methods for using antisense suppression to inhibit the expression of endogenous genes in plants are described, for example, in Liu et al (2002) *Plant Physiol.* 129:1732-1743 and U.S. Pat. Nos. 5,759,829 and 5,942,657, each of which is herein incorporated by reference. In specific embodiments, the antisense element comprise or consists of the complement of at least 15, 20, 22, 25 or greater contiguous nucleotides of any one of SEQ ID NO: 1-408.

iii. Double Stranded RNA Silencing Element

A "double stranded RNA silencing element" or "dsRNA" comprises at least one transcript that is capable of forming a dsRNA either before or after ingestion by a pest. Thus, a "dsRNA silencing element" includes a dsRNA, a transcript or polyribonucleotide capable of forming a dsRNA or more than one transcript or polyribonucleotide capable of forming a dsRNA. "Double stranded RNA" or "dsRNA" refers to a polyribonucleotide structure formed either by a single self-complementary RNA molecule or a polyribonucleotide structure formed by the expression of least two distinct RNA strands. The dsRNA molecule(s) employed in the methods and compositions of the invention mediate the reduction of expression of a target sequence, for example, by mediating RNA interference "RNAi" or gene silencing in a sequence-specific manner. In the context of the present invention, the dsRNA is capable of reducing or eliminating the level or expression of a target polynucleotide or the polypeptide encoded thereby in a pest.

The dsRNA can reduce or eliminate the expression level of the target sequence by influencing the level of the target RNA transcript, by influencing translation and thereby affecting the level of the encoded polypeptide, or by influencing expression at the pre-transcriptional level (i.e., via the modulation of chromatin structure, methylation pattern, etc., to alter gene expression). See, for example, Verdel et al. (2004) *Science* 303:672-676; Pal-Bhadra et al. (2004) *Science* 303:669-672; Allshire (2002) *Science* 297:1818-1819; Volpe et al. (2002) *Science* 297:1833-1837; Jenuwein (2002) *Science* 297:2215-2218; and Hall et al. (2002) *Science* 297:2232-2237. Methods to assay for functional iRNA that are capable of reducing or eliminating the level of a sequence of interest are disclosed elsewhere herein. Accordingly, as used herein, the term "dsRNA" is meant to encompass other terms used to describe nucleic acid molecules that are capable of mediating RNA interference or gene silencing, including, for example, short-interfering RNA (siRNA), double-stranded RNA (dsRNA), micro-RNA (miRNA), hairpin RNA, short hairpin RNA (shRNA), post-transcriptional gene silencing RNA (ptgsRNA), and others.

In specific embodiments, at least one strand of the duplex or double-stranded region of the dsRNA shares sufficient sequence identity or sequence complementarity to the target polynucleotide to allow for the dsRNA to reduce the level of expression of the target sequence. As used herein, the strand that is complementary to the target polynucleotide is the "antisense strand" and the strand homologous to the target polynucleotide is the "sense strand."

In one embodiment, the dsRNA comprises a hairpin RNA. A hairpin RNA comprises an RNA molecule that is capable of folding back onto itself to form a double stranded structure. Multiple structures can be employed as hairpin elements. In specific embodiments, the dsRNA suppression element comprises a hairpin element which comprises in the following order, a first segment, a second segment, and a third segment, where the first and the third segment share sufficient complementarity to allow the transcribed RNA to form a double-stranded stem-loop structure.

The "second segment" of the hairpin comprises a "loop" or a "loop region." These terms are used synonymously herein and are to be construed broadly to comprise any nucleotide sequence that confers enough flexibility to allow self-pairing to occur between complementary regions of a polynucleotide (i.e., segments 1 and 2 which form the stem of the hairpin). For example, in some embodiments, the loop region may be substantially single stranded and act as a spacer between the self-complementary regions of the hairpin stem-loop. In some embodiments, the loop region can comprise a random or nonsense nucleotide sequence and thus not share sequence identity to a target polynucleotide. In other embodiments, the loop region comprises a sense or an antisense RNA sequence or fragment thereof that shares identity to a target polynucleotide. See, for example, International Patent Publication No.

WO 02/00904, herein incorporated by reference. In specific embodiments, the loop region can be optimized to be as short as possible while still providing enough intramolecular flexibility to allow the formation of the base-paired stem region. Accordingly, the loop sequence is generally less than 1000, 900, 800, 700, 600, 500, 400, 300, 200, 100, 50, 25, 20, 15, 10 nucleotides or less.

The "first" and the "third" segment of the hairpin RNA molecule comprise the base-paired stem of the hairpin structure. The first and the third segments are inverted repeats of one another and share sufficient complementarity to allow the formation of the base-paired stem region. In specific embodiments, the first and the third segments are fully complementary to one another. Alternatively, the first and the third segment may be partially complementary to each other so long as they are capable of hybridizing to one another to form a base-paired stem region. The amount of complementarity between the first and the third segment can be calculated as a percentage of the entire segment. Thus, the first and the third segment of the hairpin RNA generally share at least 50%, 60%, 70%, 80%, 85%, 90%, 91%, 92%, 93%, 94%, 95%, 96%, 97%, 98%, 99%, up to and including 100% complementarity.

The first and the third segment are at least about 1000, 500, 400, 300, 200, 100, 50, 40, 30, 25, 22, 20, 15 or 10 nucleotides in length. In specific embodiments, the length of the first and/or the third segment is about 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 20 nucleotides. In other embodiments, the length of the first and/or the third segment comprises at least 10-20 nucleotides, 20-35 nucleotides, 30-45 nucleotides, 40-50 nucleotides, 50-100 nucleotides, or 100-300 nucleotides. See, for example, International Publication No. WO 0200904. In specific embodiments, the first and the third segment comprises at least 20 nucleotides having at least 85% complementary to the first segment. In still other embodiments, the first and the third segments which form the stem-loop structure of the hairpin comprises 3' or 5' overhang regions having unpaired nucleotide residues.

In specific embodiments, the sequences used in the first, the second, and/or the third segments comprise domains that are designed to have sufficient sequence identity to a target polynucleotide of interest and thereby have the ability to decrease the level of expression of the target polynucleotide. The specificity of the inhibitory RNA transcripts is therefore generally conferred by these domains of the silencing element. Thus, in some embodiments of the invention, the first, second and/or third segment of the silencing element comprise a domain having at least 10, at least 15, at least 19, at least 20, at least 21, at least 22, at least 23, at least 24, at least 25, at least 30, at least 40, at least 50, at least 100, at least 200, at least 300, at least 500, at least 1000, or more than 1000 nucleotides that share sufficient sequence identity to the target polynucleotide to allow for a decrease in expression levels of the target polynucleotide when expressed in an appropriate cell. In other embodiments, the domain is between about 15 to 50 nucleotides, about 20-35 nucleotides, about 25-50 nucleotides, about 20 to 75 nucleotides, about 40-90 nucleotides about 15-100 nucleotides.

In specific embodiments, the domain of the first, the second, and/or the third segment has 100% sequence identity to the target polynucleotide. In other embodiments, the domain of the first, the second and/or the third segment having homology to the target polypeptide have at least 50%, 60%, 70%, 80%, 85%, 90%, 91%, 92%, 93%, 94%, 95%, 96%, 97%, 98%, 99%, or greater sequence identity to a region of the target polynucleotide. The sequence identity of the domains of the first, the second and/or the third segments to the target polynucleotide need only be sufficient to decrease expression of the target polynucleotide of interest. See, for example, Chuang and Meyerowitz (2000) *Proc. Natl. Acad. Sci. USA* 97:4985-4990; Stoutjesdijk et al. (2002) *Plant Physiol.* 129: 1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

The amount of complementarity shared between the first, second, and/or third segment and the target polynucleotide or the amount of complementarity shared between the first segment and the third segment (i.e., the stem of the hairpin structure) may vary depending on the organism in which gene expression is to be controlled. Some organisms or cell types may require exact pairing or 100% identity, while other organisms or cell types may tolerate some mismatching. In some cells, for example, a single nucleotide mismatch in the targeting sequence abrogates the ability to suppress gene expression. In these cells, the suppression cassettes of the invention can be used to target the suppression of mutant genes, for example, oncogenes whose transcripts comprise point mutations and therefore they can be specifically targeted using the methods and compositions of the invention without altering the expression of the remaining wild-type allele.

Any region of the target polynucleotide can be used to design the domain of the silencing element that shares sufficient sequence identity to allow expression of the hairpin transcript to decrease the level of the target polynucleotide. For instance, the domain can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof. In specific embodiments a domain of the silencing element shares sufficient homology to at least about 15 consecutive nucleotides from about nucleotides 1-50, 50-100, 100-150, 150-200, 200-250, 250-300, 300-350, 350-400, 400-450, 450-500, 550-600, 600-650, 650-700, 750-800, 850-900, 950-1000, 1000-1050, 1050-1100, 1100-1200, 1200-1300, 1300-1400, 1400-1500, 1500-1600, 1600-1700, 1700-1800, 1800-1900, 1900-2000 of the target sequence. In some instances to optimize the siRNA sequences employed in the hairpin, the synthetic oligodeoxyribonucleotide/RNAse H method can be used to determine sites on the target mRNA that are in a conformation that is susceptible to RNA silencing. See, for example, Vickers et al. (2003) *J. Biol. Chem.* 278:7108-7118 and Yang et al. (2002) *Proc. Natl. Acad. Sci. USA* 99:9442-9447, herein incorporated by reference. These studies indicate that there is a significant correlation between the RNase-H-sensitive sites and sites that promote efficient siRNA-directed mRNA degradation.

The hairpin silencing element may also be designed such that the sense sequence or the antisense sequence do not correspond to a target polynucleotide. In this embodiment, the sense and antisense sequence flank a loop sequence that comprises a nucleotide sequence corresponding to all or part of the target polynucleotide. Thus, it is the loop region that determines the specificity of the RNA interference. See, for example, WO 02/00904, herein incorporated by reference.

In specific embodiments, the silencing element comprising the hairpin comprises a sequence selected from the group consisting of a polynucleotide comprising or consist of at least one of the sequences set forth in SEQ ID NO: 22-408. In further embodiments, the hairpin comprises a sequence selected from the group consisting of SEQ ID NO: 23 and 24; 26 and 27; 29 and 30; 32 and 33; 35 and 36; 38 and 39; 41 and 42; 44 and 45; 47 and 48; 50 and 51; 53 and 54; 56 and 57; 59 and 60; 62 and 63; 65 and 66; 68 and 69; 71 and 72; 74 and 75; 77 and 78; 80 and 81; 83 and 84; 86 and 87; 89 and 90; 92 and 93; 95 and 96; 98 and 99; 101 and 102; 104 and 105; 107 and 108; 110 and 111; 113 and 114; 116 and 117; 119 and 120; 122 and 123; 125 and 126; 128 and 129; 131 and 132; 134 and 135; 137 and 138; 140 and 141; 143 and 144; 146 and 147; 149 and 150; 152 and 153; 155 and 156; 158 and 159; 161 and 162; 164 and 165; 167 and 168; 170 and 171; 173 and 174; 176 and 177; 179 and 180; 182 and 183; 185 and 186; 188 and 189; 191 and 192; 194 and 195; 197 and 198; 200 and 201; 203 and 204; 206 and 207; 209 and 210; 212 and 213; 215 and 216; 218 and 219; and/or 221 and 222.

In other embodiments, the hairpin comprises or consist of a sequence selected from the group consisting of at least one of the sequences set forth in SEQ ID NOS: 284 and 285, 290 and 291, 293 and 294; 305 and 306; 317 and 318; 320 and 321; 323 and 324; 326 and 327; 329 and 330; 332 and 333; 335 and 336; 338 and 339; 341 and 342; 344 and 345; or 347 and 348. As exemplified elsewhere herein, expression of these sequences controls *lygus*.

In addition, transcriptional gene silencing (TGS) may be accomplished through use of a hairpin suppression element where the inverted repeat of the hairpin shares sequence identity with the promoter region of a target polynucleotide to be silenced. See, for example, Aufsatz et al. (2002) *PNAS* 99 (Suppl. 4):16499-16506 and Mette et al. (2000) *EMBO J* 19(19):5194-5201.

In other embodiments, the dsRNA can comprise a small RNA (sRNA). sRNAs can comprise both micro RNA (miRNA) and short-interfering RNA (siRNA) (Meister and Tuschl (2004) *Nature* 431:343-349 and Bonetta et al. (2004) *Nature Methods* 1:79-86). miRNAs are regulatory agents comprising about 19 ribonucleotides which are highly efficient at inhibiting the expression of target polynucleotides. See, for example Javier et al. (2003) *Nature* 425: 257-263, herein incorporated by reference. For miRNA interference, the silencing element can be designed to express a dsRNA molecule that forms a hairpin structure containing a 19-nucleotide sequence that is complementary to the target polynucleotide of interest. The miRNA can be synthetically made, or transcribed as a longer RNA which is subsequently cleaved to produce the active miRNA. Specifically, the miRNA can comprise 19 nucleotides of the sequence having homology to a target polynucleotide in sense orientation and 19 nucleotides of a corresponding antisense sequence that is complementary to the sense sequence.

When expressing an miRNA, it is recognized that various forms of an miRNA can be transcribed including, for example, the primary transcript (termed the "pri-miRNA") which is processed through various nucleolytic steps to a shorter precursor miRNA (termed the "pre-miRNA"); the pre-miRNA; or the final (mature) miRNA is present in a duplex, the two strands being referred to as the miRNA (the strand that will eventually basepair with the target) and miRNA*. The pre-miRNA is a substrate for a form of dicer that removes the miRNA/miRNA* duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) *Genes & Development* 18:2237-2242 and Guo et al. (2005) *Plant Cell* 17:1376-1386).

The methods and compositions of the invention employ silencing elements that when transcribed "form" a dsRNA molecule. Accordingly, the heterologous polynucleotide being expressed need not form the dsRNA by itself, but can interact with other sequences in the plant cell or in the pest gut after ingestion to allow the formation of the dsRNA. For example, a chimeric polynucleotide that can selectively silence the target polynucleotide can be generated by expressing a chimeric construct comprising the target sequence for a miRNA or siRNA to a sequence corresponding to all or part of the gene or genes to be silenced. In this embodiment, the dsRNA is "formed" when the target for the miRNA or siRNA interacts with the miRNA present in the cell. The resulting dsRNA can then reduce the level of expression of the gene or genes to be silenced. See, for example, U.S. Provisional Application No. 60/691,613, filed Jun. 17, 2005, entitled "Methods and Compositions for Gene Silencing, herein incorporated by reference. The construct can be designed to have a target for an endogenous miRNA or alternatively, a target for a heterologous and/or synthetic miRNA can be employed in the construct. If a heterologous and/or synthetic miRNA is employed, it can be introduced into the cell on the same nucleotide construct as the chimeric polynucleotide or on a separate construct. As discussed elsewhere herein, any method can be used to introduce the construct comprising the heterologous miRNA.

IV. Variants and Fragments

By "fragment" is intended a portion of the polynucleotide or a portion of the amino acid sequence and hence protein encoded thereby. Fragments of a polynucleotide may encode protein fragments that retain the biological activity of the native protein. Alternatively, fragments of a polynucleotide that are useful as a silencing element or a suppressor enhancer element do not need to encode fragment or variant proteins that retain biological activity. Thus, fragments of a nucleotide sequence may range from at least about 10, about 15, 20 nucleotides, about 50 nucleotides, about 75 nucleotides, about 100 nucleotides, 200 nucleotides, 300 nucleotides, 400 nucleotides, 0.500 nucleotides, 600 nucleotides, 700 nucleotides and up to the full-length polynucleotide employed in the invention. Methods to assay for the activity of a desired silencing element are described elsewhere herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polypeptides employed in the invention. Variant polynucleotides also include synthetically derived polynucleotide, such as those generated, for example, by using site-directed mutagenesis, but continue to retain the desired activity. Generally, variants of a particular polynucleotide of the invention (i.e., a silencing element) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein. A silencing element or suppressor enhancer element of a variant target sequence need not encodes a protein, but rather will have the ability to reduce the level of expression of the target sequence.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides employed in the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, as discussed elsewhere herein. Such variants may result from, for example, genetic polymorphism or from human manipulation. Biologically active variants of a native protein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as I-15 amino acid residues, as few as 1-10, such as 6-10, as few as 5, as few as 4, 3, 2, or even 1 amino acid residue.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

V. DNA Constructs

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotide encoding the silencing element employed in the methods and compositions of the invention can be provided in expression cassettes for expression in a plant or organism of interest. It is recognized that multiple silencing elements including multiple identical silencing elements, multiple silencing elements targeting different regions of the target sequence, or multiple silencing elements from different target sequences can be used. In this embodiment, it is recognized that each silencing element can be contained in a single or separate cassette, DNA construct, or vector. As discussed, any means of providing the silencing element is contemplated. A plant or plant cell can be transformed with a single cassette comprising DNA encoding one or more silencing elements or separate cassettes comprising each silencing element can be used to transform a plant or plant cell or host cell. Likewise, a plant transformed with one component can be subsequently transformed with the second component. One or more silencing elements can also be brought together by sexual crossing. That is, a first plant comprising one component is crossed with a second plant comprising the second component. Progeny plants from the cross will comprise both components.

The expression cassette can include 5' and 3' regulatory sequences operably linked to the polynucleotide of the invention. "Operably linked" is intended to mean a functional linkage between two or more elements. For example, an operable linkage between a polynucleotide of the invention and a regulatory sequence (i.e., a promoter) is a functional link that allows for expression of the polynucleotide of the invention. Operably linked elements may be contiguous or non-contiguous. When used to refer to the joining of two protein coding regions, by operably linked is intended that the coding regions are in the same reading frame. The cassette may additionally contain at least one additional polynucleotide to be cotransformed into the organism. Alternatively, the additional polypeptide(s) can be provided on multiple expression cassettes. Expression cassettes can be provided with a plurality of restriction sites and/or recombination sites for insertion of the polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter), a polynucleotide comprising the silencing element employed in the methods and compositions of the invention, and a transcriptional and translational termination region (i.e., termination region) functional in plants. The regulatory regions (i.e., promoters, transcriptional regulatory regions, and translational termination regions) and/or the polynucleotides employed in the invention may be native/analogous to the host cell or to each other. Alternatively, the regulatory regions and/or the polynucleotide employed in the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked polynucleotide encoding the silencing element, may be native with the plant host, or may be derived from another source (i.e., foreign or heterologous) to the promoter, the polynucleotide comprising silencing element, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The polynucleotide encoding the silencing element can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

An inducible promoter, for instance, a pathogen-inducible promoter could also be employed. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression within a particular plant tissue. Tissue-preferred promoters include Yamamoto et al. (1997) *Plant J.*=12(2):255-265; Kawamata et al. (1997) *Plant Cell Physiol.* 38(7):792-803; Hansen et al. (1997) *Mol. Gen Genet.* 254(3): 337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

In one embodiment of this invention the plant-expressed promoter is a vascular-specific promoter such as a phloem-specific promoter. A "vascular-specific" promoter, as used herein, is a promoter which is at least expressed in vascular cells, or a promoter which is preferentially expressed in vascular cells. Expression of a vascular-specific promoter need not be exclusively in vascular cells, expression in other cell types or tissues is possible. A "phloem-specific promoter" as used herein, is a plant-expressible promoter which is at least expressed in phloem cells, or a promoter which is preferentially expressed in phloem cells.

Expression of a phloem-specific promoter need not be exclusively in phloem cells, expression in other cell types or tissues, e.g., xylem tissue, is possible. In one embodiment of this invention, a phloem-specific promoter is a plant-expressible promoter at least expressed in phloem cells, wherein the expression in non-phloem cells is more limited (or absent) compared to the expression in phloem cells. Examples of suitable vascular-specific or phloem-specific promoters in accordance with this invention include but are not limited to the promoters selected from the group consisting of: the SCSV3, SCSV4, SCSV5, and SCSV7 promoters (Schunmann et al. (2003) *Plant Functional Biology* 30:453-60; the rolC gene promoter of *Agrobacterium rhizogenes* (Kiyokawa et al. (1994) *Plant Physiology* 104:801-02; Pandolfini et al. (2003) *BioMedCentral (BMC) Biotechnology* 3:7, (www-.biomedcentral.com/1472-6750/3/7); Graham et al. (1997) *Plant Mol. Biol.* 33:729-35; Guivarc'h et al. (1996); Almon et al. (1997) *Plant Physiol.* 115:1599-607; the rolA gene promoter of *Agrobacterium rhizogenes* (Dehio et al. (1993) *Plant Mol. Biol.* 23:1199-210); the promoter of the *Agrobacterium tumefaciens* T-DNA gene 5 (Korber et al. (1991) *EMBO J.* 10:3983-91); the rice sucrose synthase RSs1 gene promoter (Shi et al. (1994) *J. Exp. Bot.* 45:623-31); the CoYMV or Commelina yellow mottle badnavirus promoter (Medberry et al. (1992) *Plant Cell* 4:185-92; Zhou et al. (1998) *Chin. J. Biotechnol.* 14:9-16); the CFDV or coconut foliar decay virus promoter (Rohde et al. (1994) *Plant Mol. Biol.* 27:623-28; Hehn and Rhode (1998) *J. Gen. Virol.* 79:1495-99); the RTBV or rice tungro bacilliform virus promoter (Yin and Beachy (1995) *Plant J.* 7:969-80; Yin et al. (1997) *Plant J.* 12:1179-80); the pea glutamin synthase GS3A gene (Edwards et al. (1990) *Proc. Natl. Acad. Sci. USA* 87:3459-63; Brears et al. (1991) *Plant J.* 1:235-44); the inv CD111 and inv CD141 promoters of the potato invertase genes (Hedley et al. (2000) *J. Exp. Botany* 51:817-21); the promoter isolated from *Arabidopsis* shown to have phloem-specific expression in tobacco by Kertbundit et al. (1991) *Proc. Natl. Acad. Sci. USA* 88:5212-16); the VAHOX1 promoter region (Tornero et al. (1996) *Plant J.* 9:639-48); the pea cell wall invertase gene promoter (Zhang et al. (1996) *Plant Physiol.* 112:1111-17); the promoter of the endogenous cotton protein related to chitinase of US published patent application 20030106097, an acid invertase gene promoter from carrot (Ramloch-Lorenz et al. (1993) *The Plant J.* 4:545-54); the promoter of the sulfate transporter geneSultr1; 3 (Yoshimoto et al. (2003) *Plant Physiol.* 131:1511-17); a promoter of a sucrose synthase gene (Nolte and Koch (1993) *Plant Physiol.* 101:899-905); and the promoter of a tobacco sucrose transporter gene (Kuhn et al. (1997) *Science* 275-1298-1300).

Possible promoters also include the Black Cherry promoter for Prunasin Hydrolase (PH DL1.4 PRO) (U.S. Pat. No. 6,797,859), Thioredoxin H promoter from cucumber and rice (Fukuda A et al. (2005). *Plant Cell Physiol.* 46(11):1779-86), Rice (RSs1) (Shi, T. Wang et al. (1994). *J. Exp. Bot.* 45(274): 623-631) and maize sucrose synthese-1 promoters (Yang, N-S. et al. (1990) *PNAS* 87:4144-4148), PP2 promoter from pumpkin Guo, H. et al. (2004) *Transgenic Research* 13:559-566), At SUC2 promoter (Truernit, E. et al. (1995) *Planta* 196(3):564-70. At SAM-1 (S-adenosylmethionine synthetase) (Mijnsbrugge K V. et al. (1996) *Planr. Cell. Physiol.* 37(8): 1108-1115), and the Rice tungro bacilliform virus (RTBV) promoter (Bhattacharyya-Pakrasi et al. (1993) *Plant J.* 4(1):71-79).

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16.215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

VI. Compositions Comprising Silencing Elements

One or more of the polynucleotides comprising the silencing element can be provided as an external composition such as a spray or powder to the plant, plant part, seed, a pest, or an area of cultivation. In another example, a plant is transformed with a DNA construct or expression cassette for expression of at least one silencing element. In either compositions, the silencing element, when ingested by an insect, can reduce the level of a target pest sequence and thereby control the pest (i.e., any pest from the *Lygus* genus, such as, *Lygus hesperus*). It is recognized that the composition can comprise a cell (such as plant cell or a bacterial cell), in which a polynucleotide encoding the silencing element is stably incorporated into the genome and operably linked to promoters active in the cell. Compositions comprising a mixture of cells, some cells expressing at least one silencing element are also encompassed. In other embodiments, compositions comprising the silencing elements are not contained in a cell. In such embodiments, the composition can be applied to an area inhabited by a pest. In one embodiment, the composition is applied externally to a plant (i.e., by spraying a field or area of cultivation) to protect the plant from the pest.

The composition of the invention can further be formulated as bait. In this embodiment, the compositions comprise a food substance or an attractant which enhances the attractiveness of the composition to the pest.

The composition comprising the silencing element can be formulated in an agriculturally suitable and/or environmentally acceptable carrier. Such carriers can be any material that the animal, plant or environment to be treated can tolerate. Furthermore, the carrier must be such that the composition remains effective at controlling a pest. Examples of such carriers include water, saline, Ringer's solution, dextrose or other sugar solutions, Hank's solution, and other aqueous physiologically balanced salt solutions, phosphate buffer, bicarbonate buffer and Tris buffer. In addition, the composition may include compounds that increase the half-life of a composition.

It is recognized that the polynucleotides comprising sequences encoding the silencing element can be used to transform organisms to provide for host organism production of these components, and subsequent application of the host organism to the environment of the target pest(s). Such host organisms include baculoviruses, bacteria, and the like. In this manner, the combination of polynucleotides encoding the silencing element may be introduced via a suitable vector into a microbial host, and said host applied to the environment, or to plants or animals.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be stably incorporated into the genome of the cell (e.g., chromosome, plasmid, plastid, or mitochondrial DNA), converted into an autonomous replicon, or transiently expressed (e.g., transfected mRNA).

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the sequences encoding the silencing element, and desirably, provide for improved protection of the components from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir*, and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pollulans*. Of particular interest are the pigmented microorganisms.

A number of ways are available for introducing the polynucleotide comprising the silencing element into the microorganism host under conditions that allow for stable maintenance and expression of such nucleotide encoding sequences. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (2000); *Molecular Cloning. A Laboratory Manual* ($3^{rd}$ ed.; Cold Spring Harbor Laboratory Press, Plainview, N.Y.); Davis et al. (1980) *Advanced Bacterial Genetics* (Cold Spring Harbor Laboratory, Cold Spring Harbor, N.Y.; and the references cited therein.

Suitable host cells include the prokaryotes and the lower eukaryotes, such as fungi. Illustrative prokaryotes, both Gram-negative and Gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as *photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

Characteristics of particular interest in selecting a host cell for purposes of the invention include ease of introducing the coding sequence into the host, availability of expression systems, efficiency of expression, stability in the host, and the presence of auxiliary genetic capabilities. Characteristics of interest for use as a pesticide microcapsule include protective qualities, such as thick cell walls, pigmentation, and intracellular packaging or formation of inclusion bodies; leaf affinity; lack of mammalian toxicity; attractiveness to pests for ingestion; and the like. Other considerations include ease of formulation and handling, economics, storage stability, and the like.

Host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

The sequences encoding the silencing elements encompassed by the invention can be introduced into microorganisms that multiply on plants (epiphytes) to deliver these components to potential target pests. Epiphytes, for example, can be gram-positive or gram-negative bacteria.

The silencing element can be fermented in a bacterial host and the resulting bacteria processed and used as a microbial spray in the same manner that *Bacillus thuringiensis* strains have been used as insecticidal sprays. Any suitable microorganism can be used for this purpose. *Pseudomonas* has been used to express *Bacillus thuringiensis* endotoxins as encapsulated proteins and the resulting cells processed and sprayed as an insecticide Gaertner et al. (1993), in *Advanced Engineered Pesticides*, ed. L. Kim (Marcel Decker, Inc.).

Alternatively, the components of the invention are produced by introducing heterologous genes into a cellular host. Expression of the heterologous sequences results, directly or indirectly, in the intracellular production of the silencing element. These compositions may then be formulated in accordance with conventional techniques for application to the environment hosting a target pest, e.g., soil, water, and foliage of plants. See, for example, EPA 0192319, and the references cited therein.

In the present invention, a transformed microorganism can be formulated with an acceptable carrier into separate or combined compositions that are, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention (i.e., at least one silencing element) are normally applied in the form of compositions and can be applied to the crop area, plant, or seed to be treated. For example, the compositions may be applied to grain in preparation for or during storage in a grain bin or silo, etc. The compositions may be applied simultaneously or in succession with other compounds. Methods of applying an active ingredient or a composition that contains at least one silencing element include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions comprising the silencing element can be in a suitable form for direct application or as a concentrate of primary composition that requires dilution with a suitable quantity of water or other dilutant before application.

The compositions (including the transformed microorganisms) can be applied to the environment of an insect pest (such as a pest from the *Lygus* genus) by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the composition(s) and/or transformed microorganism(s) may be mixed with grain to protect the grain during storage. It is generally important to obtain good control of pests in the early stages of plant growth, as this is the time when the plant can be most severely damaged. The compositions can conveniently contain another insecticide if this is thought necessary. In an embodiment of the invention, the composition(s) is applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, an insecticide, a fertilizer, in an inert carrier, and dead cells of a *Bacillus* strain or transformed microorganism of the invention.

VII. Plants, Plant Parts, and Methods of Introducing Sequences into Plants

In one embodiment, the methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. Nos. 5,886,244; and, 5,932,782; Tomes et al. (1995) in *Plant Cell, Tissue, and Organ Culture. Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the silencing element sequences of the invention can be provided to a plant using a variety of transient transformation methods. Such transient transformation methods include, but are not limited to, the introduction of the protein or variants and fragments thereof directly into the plant or the introduction of the transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, polynucleotides can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which its released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudoisuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies* balsamea); and cedars such as Western red cedar (*Thuja plicata*) and Alaska yellow-cedar (*Chamaecyparis noolkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

VIII. Methods of Use

The methods of the invention comprise methods for controlling a pest (i.e., pest from the *Lygus* genus, such as, *Lygus hesperus*) comprising feeding to a pest a composition comprising a silencing element of the invention, wherein said silencing element, when ingested by a pest (i.e., pests from the *Lygus* genus, such as, *Lygus hesperus*), reduces the level of a target polynucleotide of the pest and thereby controls the pest. The pest can be fed the silencing element in a variety of ways. For example, in one embodiment, the polynucleotide comprising the silencing element is introduced into a plant. As the *Lygus* feeds on the plant or part thereof expressing these sequences, the silencing element is delivered to the pest. When the silencing element is delivered to the plant in this manner, it is recognized that the silencing element can be expressed constitutively or alternatively, it may be produced in a stage-specific manner by employing the various inducible or tissue-preferred or developmentally regulated promoters that are discussed elsewhere herein. For example, the silience element could be expressed in aerial plant tissues such as, the leaves, stem, flower, etc. In other embodiments, the silencing element is expressed in a root. In these embodiments, Hemioptera such as grape phylloxera can be targeted.

In another method, a composition comprising at least one silencing element of the invention is applied to a plant. In such embodiments, the silencing element can be formulated in an agronomically suitable and/or environmentally acceptable carrier, which are preferably, suitable for dispersal in fields. In addition, the carrier can also include compounds that increase the half life of the composition. In specific embodiments, the composition comprising the silencing element is formulated in such a manner such that it persists in the environment for a length of time sufficient to allow it to be delivered to a pest. In such embodiments, the composition can be applied to an area inhabited by a pest. In one embodiment, the composition is applied externally to a plant (i.e., by spraying a field) to protect the plant from pests.

In certain embodiments, the constructs of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, U.S. Provisional Application No. 61/021,676, entitled "Compositions and Methods for the Suppression of Target Polynucleotides", filed Jan. 17, 2008 and herein incorporated by reference in its entirety.

As used herein, a "suppressor enhancer element" comprises a polynucleotide comprising the target sequence to be suppressed or an active fragment or variant thereof. It is recognize that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element. Thus, in specific embodiments, the suppressor enhancer element comprises a fragment or a variant of a polynucleotide encoding a potassium channel polypeptide, a cuticle polypeptide, an endocuticle polypeptide, a chitin binding polypeptide, a chitinase polypeptide, a hormone inducible polypeptide, a translation initiation factor, a voltage dependant channel, an EIF-related polypeptide, a polypeptide having a coiled coil helix domain, a polypeptide having a zinc finger domain, a receptor associated finger polypeptide, a lethal timorous imaginal disc polypeptide, a ribonucleoprotein, a cathepsin protease polypeptide, a polyprotein deformed destructor, and a death associated leucine rich polypeptide. In still other embodiments, the suppressor enhancer element comprises a polynucleotide set forth in SEQ ID NO: 1-42 or an active variant or fragment thereof.

It is recognized that multiple suppressor enhancer elements from the same target sequence or from different target sequences, or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element allows for the systemic production of RNAi occurs throughout the entire plant. In further embodiments, the plant or plant parts of the invention have improved loading of RNAi into the phloem of the plant over what would be observed with the expression of the silencing element construct alone and, thus provide better control of phloem feeding insects by an RNAi approach. In specific embodiments, the plants, plant parts, and plant cells of the invention can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell, or phloem when compared to an appropriate control. In other embodiments, the increase in the level of RNAi in the plant, plant part, plant cell, or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Methods to assay for an increase in the level of RNAi are discussed elsewhere herein.

The following examples are offered by way of illustration and not by way of limitation.

EXPERIMENTAL

Example 1

Specific Target Genes and Silencing Elements that Cause Insecticidal Activity Against *Lygus Hesperus*

Disruption of insect gene function via RNAi can produce specific activity against target insects. This specificity is enhanced by delivery of the dsRNAs via transgenic plants. Identification of gene function in insects via RNAi has been largely limited to injection of dsRNAs. In fact, past experiments have indicated that insects are not capable of systemic RNAi response based on exposure to dsRNAs.

As described below, we have demonstrated acute activity of numerous dsRNA pairs through injection experiments and additionally have demonstrated insect antagonism through ingestion of dsRNAs. This evidence identifies several gene/primer pair combinations with clear insecticidal properties. The use of dsRNAs in transgenic plants also addresses the potential complication of heterologous protein expression and the possible risks of allergic reaction, non-target activity, and environmental- or bioaccumulation. The data presented below represents the first test of disruption of these particular genes resulting in insecticidal activity in whole organisms and the first report of insecticidal activity of dsRNAs against L. Hesperus.

The invention describes specific target genes and the dsRNA sequences causing insecticidal activity against the hemipteran Lygus hesperus through RNA interference of the target gene's expression. Disruption of the genes targeted by the dsRNA sequences may be broadly insecticidal in numerous species. The specific dsRNA sequences display insecticidal activity upon ingestion indicating they can be utilized with a transgenic plant mode of delivery. Table 1 provides the polynucleotide of each target sequence from Lygus hesperus, a brief description of the function of the protein encoded by the target sequence, and a SEQ ID NO. Table 2 provides a summary of the blastx and blastn sequence homology results for each target sequence from Lygus hesperus. Table 3 provides a summary of primers used to suppress the target polynucleotides.

TABLE 1

Target Polynucleotides from Lygus Hesperus.

SEQ ID NO:1
ilh1c.pk005.o10.f
potassium plus
GCGTCACTTGCGACTCGTGTCTGAGCGGCAACTTCAAGGGAAA
151: GAGGTACAAATGTCTTTCCTGCTACGACTACGATCTGTGCACCAACTGCTACGAGTGTGGCCTCATCACGGGACT
226: CCACTCAGCAGAGCATCCCATGCAGTGCATCATCACCAGACATGACGTCGACCTGTACTTCGGGGGAGACATGAA
301: TGGCGACGGAAGTCAGTCCTACACGTGTCCTCATTGTGGTCTAATGGGGTTCAGTTTGTCGCTGTTGATCGAGCA
376: CGTGAGCGGTGAGCATATCGCGCTGAGCAACGCTGAAGTGATTTGCCCTGTTTGCGCCGCCACGCCAGTCAACCG
451: ACCGAACAACGTTCGCCAGGATTTTTTGGGGCACCTGACGCTGGAGCATCGCTACCCCTCGCGAGAGCTGACCGC
526: CTTCTTCGAAGAGCCCTCGTCCCGACACATGCCGAGTGGCGTCCGCCGGATTCCACCGCCACCAGGGCGCAGCGC
601: TGCCGGGCGTGGACGCCGGGTCGCACGTTCATTTCGGCTCCTCAGGCGCTCTTACTGGACTCACATCCTCCAGAG
676: AAAGTCCGGATCCCATCGCCGAGTTCTTCTCTCAGCTGTCTGgagtcgctcgtcctcaaggtcctgggccgattc SEQ ID NO:2
ilh1c.pk004.e6.f
cuticle protein plus
ACCCCCTGATCGCCGGGATCGTTGCCAATCAGTATCACGCTCAGGATGTG
226: CTCGGACAGTACACTTACGGCTACTCCGGAnCCCCATCCGCTAAACAAGAGGTTAAGACTGCTGACGGAATAACG
301: AGAGGATCTTACTCGTACATCGATGGAAACGGGTCTCGTACAGAGCGCTTCTTACGTTGCTGACCCCGTCAACGG
376: GTTCAGAGTCCACGCCACCAACCTGCCCGTGGGACCTGACGGGTCCGTCGCTGCCGCTCCCGTCGCCAGGCTCCT
451: CAGCCCTTTGGCCATCAGCCCTGTGATCAACCTCCACGGCGCTGCTCCCCTCAACCCCGACGGCACCGTCGCTGA
526: CACCCATGAAGTCGCTGTCGCCAAGGCCGCTCACCTCGCTGCCATCAACGAGGCTAGGGCTAGAGGCAAGAGGTC
601: nGCCCCGCTCAACCCCGACGGTACCGTCGCTGACACCCCCGAAGTTGCTGCTGCTAAGTGGGCTCATCTCGCTGA
676: GATCTCCAAAGCTGGTGGAATCCCTCTCGTATACGCTCCCAGATGGTGGGGACCTGGTGCTCCATTGAACGCTGA SEQ ID NO:3
ilh1c.pk001.e23.f
cuticle plus
CTACGCTGGCGGCCCCTCCGCCAAGGAAGAGATCAAGACCGCCGACGG
151: AATTACCCGCGGAGGATACTCATACATCGACGCCAACGGTATCGTCCAGAGCGCCTCTTACGTGTCGGATCCCGT
226: CAACGGATTCCGAGTAGCCGCCACTAACCTCCCCGCTGGACCTGCAGTCCCAGCTGGACCTTCAGTGGTTGCTGC
301: TGCTCCAGCTGTCGTTGCTGCTCCTGCTCCAGTTTTGGCTGCTGCCCCTGCTCCAATTGTGGCTTCAGCTCCCGT
376: TTGGGCTGCTCAACCAGCTGTTGTTGCCGCTCCAGCTCCTGTCGCTGTCGCCGAAGGCCCCGCAGTGACCGCCAC
451: CAACGTCCAGGAAGTTGCTGCCGCTGCTGCTGACGTCCCCGTTGCTGCTGATCTCCCCGAGATCATCGCTGCCCG
526: CTCTCTGCCCACCGTGGTTGCCACCAGGGCCGCCATCGCTCACCCCCTTGCCGCAACCTCCTGGTCCGGCATCGT
601: CCACCACCTGAAGAAGCGTTCCCTTGCCGCCGCTACCGTCGTCACTCCCCTTACTAGTTACCCCGGATCTACCGC
676: TCCCTTGGTTCACGCTTCTCCCGTTATTGCGGCTACACCTGTTATCTCCGCTCACTCGGGTTTGATCGCCACTGA
751: CTCTCTTGTAncctcaccacacctcgttggtgcagtangtnctgtcnagcccctccacaccgccntcctcanan SEQ ID NO:4
ilh1c.pk010.f11.f
endo cuticle plus
CATTCGGGAGACATTGCAAAACTGGATGCATAGGGGAAGTCTTTA
151: GGACGGATTTACGGCATACAGTACATGTTACTGTAAGACACGGCGCGTGACTGGACAGCAAGCAGAATGGAGGAG
226: GGACAAGTGTACCAATCATCCGACCAAACCAACTACGTTTACGATGAAGTGTTTCCTGCGCTACCTGAATCAGCC
301: AACCCGGCACCTCACAACGACATCAAAATTTGCAACAACAAAATGCGTGTTGGCTCATCTGTCATCACTCAGGTT
376: TTCCGAGTGCCAGCAGACGAGCGCCGCTACGATCACAACAACAGCTTTGGGGAAAAGGAATCCGTGAGGACCTGC
451: TCTGCCATCATGAAGGAAACTGGAGCAGTCATTGAGATCGCCACGAGCAAGGATATGTCTCTGACTTTCTTGGTG
526: ACTGGAAAGACCGACTCAGTGATGGATGCTCGAAGGAAGATACTGAGCAATTTTCAGACCCAAGCTTCATCCAAG
601: CTCTCTATTCCGAAAGAGCATCACAGGTGGATCCTTGGAAAAGCTGGTGGTCGTCTGAAGGATTTGGAAAAATCA
676: ACAGCCACCAAAATCTCCGTCCCTGGCATAAATGAACACTCGGATGAAATCACTGTGACGGGAACTCGTGAAGGG
751: ATCGACAAGGCCATCCATGAAATGCAAGTnatttcggacgaacaatccaagaagn TABLE 1-continued Target Polynucleotides from *Lygus Hesperus*.

SEQ ID NO:5
ilh1c.pk011.m15.f
cuticle plus
AACCCCCTGATCGCCGGGATCGTTGCCAATCAGTATCACGCTCAGGATGTG
226: CTCGGACAGTACACTTACGGCTACTCCGGAnCCCCATCCGCTAAACAAGAGGTTAAGACTGCTGACGGAATAACG
301: AGAGGATCTTACTCGTACATCGATGGAAACGGGTCTCGTACAGAGCGCTTCTTACGTTGCTGACCCCGTCAACGG
376: GTTCAGAGTCCACGCCACCAACCTGCCCGTGGGACCTGACGGGTCCGTCGCTGCCGCTCCCGTCGCCAGGCTCCT
451: CAGCCCTTTGGCCATCAGCCCTGTGATCAACCTCCACGGCGCTGCTCCCCTCAACCCCGACGGCACCGTCGCTGA
526: CACCCATGAAGTCGCTGTCGCCAAGGCCGCTCACCTCGCTGCCATCAACGAGGCTAGGGCTAGAGGCAAGAGGTC
601: nGCCCCGCTCAACCCCGACGGTACCGTCGCTGACACCCCCGAAGTTGCTGCTGCTAAGTGGGCTCATCTCGCTGA
676: GATCTCCAAAGCTCGTGGAATCCCTCTCGTATACGCTCCCAGATGGTGGGGACCTGGTGCTCCATTGAACGCTGA SEQ ID NO:6
ilh1c.pk005.d21.f
chitin binding plus
CCAACATGTATCTCTCAGTTGTTGGATTGGTGATGGCTTCCGCTG
151: CTTTCGTCAGCTGCGAGCCATCGAATTTCGCGTGTACTGGCGAGTCGAACTACAAGTATCCTGTGGAGGGCTCGT
226: GCCACAACTACTACCAGTGCGAAAAGGGCTCCACTACGCCTTCAATTCGAGACTGCTCGCTGCCGCTGCTTCGAT
301: TTCGGGATTTCGATCCAGTCAAATTGGAGTGTGACTGGTGCTGGCGGGTAGACTGTTCAGCCAAACCCGCACCCC
376: CACCGACTCCATCGCCGACTCCGGCGCCAACTTCAAGGCCTACTGCTGCGCCGACTACTGGACCAACCTCAGCGC
451: CCACTACTGGACCCACAGCGGCGCCAACCTCAGCGCCCACTGCTGCACCAACCTCAGCTCCCACTGCTGCTCCAA
526: CTCCAGCGCCCACTGCGCCGCCAACTCCAGCGCCCACTGCGGCGCCAACTCCAGCGCCCACTGCAGCACCAACCT
601: CAGCTCCCACTGCTGCTCCAACTCCAGCGCCTACTGCTGCTCCAACTCCAGCGCCTACTGCTGCGCCAACATCAG
676: CGCCCTCTACTGGACCCACTGTCGCCCCAACTCGCAGGCCAnctcaagaacccacaatggcaaaaaaatcttcga SEQ ID NO:7
ilh1c.pk011.f4.f
chitinase plus
CAAATAAGAAACATGAAGATAGTACCGTTCTTAGTTCTTCTACTT
151: GTTCAAACGGTTCTTTCCGAAACGACGCCGGCTTCAAACAATCGCCGTATTGTTTGCTACCACACAAGTTGGAGT
226: GCGTATCGTGTCCCAGAGGCAAAATTTACAGCGAAGAACATCAACCCGTACCTTTGCACTCATTTAATATATTCG
301: TTTGCCAATGTATTGGTAAATGAAGCAACCATCGTTCCTGGTGATGCATGGCAGGATATTGATAACCATCAGTTC
376: AGAGATTTTGTTGAGTTGAAAACCACATTCAACGAAAACCTGAAAACGTTACTCGCAATAGGAGGCTACAGAGAA
451: GGGTCGTCGAAGTTCACCCCTATCGCAGCCACCCCCACGAAAAGGGCAGCGTTTGCTCGCAACACGCTCAAGTTT
526: TTGAAAACTTACGGTTTTGACGGGCTCAACATCGATTGGCAGTTCCCTAACGATCAGCATAGAAATGGCAGTGTT
601: GAAGACTATAAGAACTTTGTGTATTTGCTGCAAGATATCGACAAAGTCTTCAGAGAGGAAGCTGCAGCTTCCGGG
676: AAACCTAAAATGATGTTGACCATTTCCGTTCGGGTAATACGCTGCTAATAGAAAGTGGCTATGATCTACCAAAT
751: CTAGCGAAGTATGTAGAGTTCATGAACGTCCTGAGCTACGATTACCACTTTGCn SEQ ID NO:8
ilh1c.pk004.122.f
hormone inducible; JH plus
TCCAGTTCTTTAACGAGGTAACCATGTACAAGACTATCTTAC
151: CTGAGTTGGGAGCCTTGGATTTGGGTTTGTGCCCGAAGATGTTCCATGGAGAGGCACATAATGGTAAAAATCCTG
226: AACAAGACATCGTGGTTATTGAAGATTTGTGTCCTCAAGGTTACAAAGTGCCGGAAAAGTTGTTTTTGGACGCTG
301: ATCACTTAGTGATGGCCATGAAAAAAATAGGGCAACTTCACGGATTATCTTATAAAATGAAAGTATCGTCTCCAG
376: AGAGGTTGTTCGAATTGAGGAATATGCTGATCCCGAAGGTGATTGACGATTCGAAAGGTCTCAATGATGCTTGTC
451: TGGCCAGGGGTTTCAAACCCTTGGTGGAGTCGAGCCCCAGTTACAGTGTAGTGAATAAAGTTTACAAGAAACTCG
526: TCGTAGCGGATGCCGTGGATGTTGCCTATAGTTTACAGAAGCCTGAAGAACCATTCGCCGTTATCACCCACGGTG
601: ATTTCAATGGTAATAACATATTGTATAAGTATGATGCCAGTTGGAAATGTAGTGGATATGAAAATGATAGATTTTG
676: GTTTCGCTTCTTATTTGGATCCTGCTGTTGACATAGCTTTCTTCCTGTACATGAACTCTTCTCCTGAAACTAGGA
751: AGCTGCACTGGGATTCATTCCTGAATGCATACTGGGAGGGAGTCATCTCTGTTGCTGGTGATCCn SEQ ID NO:9
ilh1c.pk003.d10.f
translation initiation factor Plus
CGTGTGCTGATCATTCGATATCCCGGAAACGTGTTTACTTTCCTTTATTG
151: TGCATAAATACACTTCCGTGGCGGTTCGCGATGTCGAATACAAAAGTCGCGTCTTCCGGTCAACCTAAGCTCTCC
226: TCCCAAGATCTTTCGACTCTTGACGTGACGGCGCTTACCCCATTGTCGCCAGAAGTCATCAGTAGACAAGCGACC
301: ATCAATATCGGTACTATTGGTCACGTGGCACATGGGAAagtcnactgtngnngaaagctgtgtctggtgttcnaa SEQ ID NO:10
ilh1c.pk010.d2.f
translation initiation factor plus
TTTTTGGTTTTCATTGAAAATTTCGATAATTTTCCAAAGTTT
151: TATTATGGTTCAAATTCAAAATGTTTTCTACTGATTTTGATTCTCACAGTATAATTTCGACGTGGAAGTGTTAAG
226: GGCTCAGTGATCGATGGCAGGGAAAGCTTTTTGATAACTATTGGTAAGTCCGAGTTTGTAAGATGACCTCTTTTC
301: AAAAGTGTGTAGGATTTGGTCGGATATTTCCTTTAGGGATTCTCAGAAATCACAATGTTGCATCTCGAAGGTGCA
376: TTCACGGCTCTTCCGTTTTGTACAAAAAGAGGAAAACCAGAGAGGAGAGGAAGTTGCCCAAAGCTATTGTTTACT
451: CTCCCAAATCGAAATGGAAACAAGGCGAGCCCGTTGACGTGTGGAAGCGTATGACAGTGGCGGAGGTAGCAAATA
526: CACTGGGTAAAGATGTAGGACACGTTTTAGAAGTTATGTCGTTCATTGACAACACGGAACAGTACAGAAAAGACC
601: GTGATGTCATCGACAACTTCAAAGTTATAGAAGAAATAGTGAAAAAGTCGGGTCATCGATGTAGGATGGCTAGTA
676: AGCCTACAGAAACTGAAGAAAAAAGTTTTAAAGATGTTGGAcgaagannccttcggattacgttgatcccaggcc TABLE 1-continued Target Polynucleotides from *Lygus Hesperus*.

SEQ ID NO:11 ilh1c.pk011.h12.f
voltage dependent channel Plus
TGCCCGAGTGCGTGTTTCGTCAAATAGAAACCCGGGTCTTTTCTGT
151: AAGAATTAAATCGCAATGGCTCCTCCTTTCTACGCTGATCTAGGTAAGAACGCCCGCGATGTCTTCGGTAAAGGG
226: TACCATTTCGGACTCCTGAAGCTCGACGTCAAGACCAAGACTAACACGGGCGTCGAATTCAGCATCGGCGGCGTT
301: CAAAACCTCGAAACCAAAAACGTAGTCGGCTCTCTCGAGACCAAGTACAAATTCAAGGAGTATGGCGTTACTTTC
376: ACGGAGAAATGGAACACTGACAACGTACTGGCCACTGAAATCGCCGTTGCTGATTTCTGCGATGGAGCAAAAATG
451: TCCCTTGACACCTCTTTTATCCCTCACAAGGGTGATAAGACCCTGCGATTGAAGGGCGAATTCAAGAATGACACC
526: TGCGCCATGAACCTGAAAGCGACTTCAAGTCTGGCGGACCTCTCGTCCGAGGTGGCGCTGTCCTCGGCTACGGA
601: GGCTGGCTATGTGGTTACGCCACGGCCTTCGACGTTAGCAAGAGTAAACTCACCGAAAACAAAGTCACCATGGGA
676: TTCATCACAAAAGATTTCATCTTGAACACCGTTATCAATGACGGAAGAGTCTTCTCTGGTTCCATCTACCACAAA
751: GTTAACAGCAAGTTGGAAACTGGAGTCCAGATCTCGTGGGCCTCTGATAACAACAGCACCGACTTCGGCATCGnc

SEQ ID NO:12 ilh1c.pk002.a24.f
voltage dependent channel plus
aTTCTGCTTGGGTTTTTTATTTAGTTGAAC
151: AGTTTTCCGTGGACTCTTATGACGATAACTTCCTCATTCCAAATCTTCTTCGGGACTATCCATCATTTTAATCAG
226: AAGTAGAAGCCGACTATTCTAAAAACCACCTATGGGCCTCCATTCTTCGCGGATCTCGGTAAAAACTCGAGAGA
301: CATCTTCAATAAAGGTTATAATTTCGGGCTGCTTAAGTTGGACATAAAAACCAGAACAGAAACCGGAGTTGAGTT
376: CGAAATCGGTGGAGTCCAGAACCTTGAGACGAAAAATGTAGCCGGCTCGCTCGAGACTAAGTACAAATTCAAGGA
451: CTTCGGGATCAGCTTTTCGGAGAAATGGAATACGGATAATGTTCTTCAGCTAGAAGTAGCTGCTGCTGATATCTG
526: CGAAGGAGTCAAAATGTCCTGCATGAGTATCATGACTCCTTCTTCAGATGAGGAGAAAGGTGGCACTGACAAAAT
601: TTTGAGATTCAAGAGTGAATATAAGAATGCTATCATGGCTGTGAACTTGGAGAGCGATTTCAAAGCTGGTGGTCC
676: GACCTTGGGAGTCTCTGGCGTTTTTGGATTAGGTGGATGGTTGCTCGGAGCTATAGCGGCATTAGATACTGAGAC
751: TTCGAAAGTGATGACCTTCTCTTTGGGAATGGGAnTTTTAACCAAAGACTTCATACTAAACACCGCTGTTATCAA
826: CAAGGGAACAGACTTCann

SEQ ID NO:13 ilh1c.pk009.f20.f
EIF-related factor plus
CGAAAGCAAACAGGACATCATATTTCGCAGGAATAAATTGGAAGA
151: TCCCATCACACGAGAAAGCAAACCGGACGTCATATTTCGCAGGGTGCGAGGTATCCTCAACAAGCTCACTCCTGA
226: GAAATTCGATAAGCTAAGCGATGACCTCTTGAAAGAAGAATTTAATTCTGATGTCATTCTCAAAGGCGTCATTCT
301: ATTGGTGTTTGAAAAAGCACTAGATGAGCCGAAGTACAGTGCTATGTATGCTCAGCTCTGCCGGCGACTTTGTGA
376: AGAGATCCGAAGTGCCGACCAGCCTGAACCCTGCCCTTTTCGCCATTTGCTTCTGTCCAGCTGCAAAGCTCAGTT
451: TGAGAGCCGTTCGAAGCACACTAGCAGCAAGCGGAAATCGCTCGGGAACATAAAGTTCATCGGAGAGCTTTGCAA
526: ACTTGGAATCCTTCAGCGCGACATCTTGTACAGGTGTTTGATCCAACTTCTCGAACACAAGACCAAGACGCCTGA
601: CGAAATGGCCGAAGATCTTGAGTGCGTCTGTCAGATCCTCCGCACTTGCGGCCACATCTTGGACAACGAGGAAGC
676: TCAGAAGCTGATGAATCAACTTTTTGATCGTATGGCGTCCCTCTCCAAGAACGTCAACCTGCCGATCCGGATCCG
751: CTTCATGCTCCGTGACATTATCGAGCTCCGGAGGGATAACTGGGTTc

SEQ ID NO:14 ilh1c.pk002.d9.f
coiled coil helix domain . . .
CTAACTTTCCTnTTCCGCGTTGTTGCGTTCCTGTGAAATTTCACTAA
151: AATTGTGATTATTTTATTGTACTCAGAACTATACCTACTTCGTATTTCGATTTGAATACATTCCAAGGGCTTTCG
226: CATGACTCAAACTTTCTTCTAGAAGTGGTTTGTTGCGACGTGTTGAGTTCAATAGTGTGGTATTCACAACCGGTT
301: TCGCCCATTGGGCCATCAACGAGTATTTTCCAGGTGATGATCTATTGATATGGGGGGCGTAGCCGCTTCAAGTCC
376: TTTGCCAGACGAAGAACCCCGACCTGAAGCTCCAGGCAGCAGGAAGGCAGACGAAGTACCTGCTGAGAGTGGTCA
451: GAACCCCGCAGGACAACCTCACCCAGATGGCGCCAAGGAAGAAGAGAACGGAGATAACGAGGnAAAGGCCTGGCC
526: TTATAAAGCCGATGGATCTATAAATTGGGATTGCCCATGTTTGGGAGGGATGGCACATGGGCCCTGTGGCGATG
601: AGTTCAGAGCTGCTTTCTCCTGTTTCCACTATTCCACTGCTGAACAAAAAGGCTCCGACTGTTTggnaaccgttc

SEQ ID NO:15 ilh1c.pk003.j7.f
zinc finger domain
CACAAAAAGCTCCATACAGGTGAACGCCC
151: TTTCAAATGCGCACACTGCGTTCGGACTTTCAGCCGGAAAGAGCACTTAGTACGGCATGCCCACTCTCATACAGG
226: ACAAAAACTCTTCAACTGCGACGTCTGCGGGAAAAGCTTCAGTCGGAAAGACAACGTACGGAAACACCGGAAAAC
301: GCATGAAACGACAGGTCCGTACTCTTGCGAGTTCTGCGGTATGCAGTTCAACGTTCGGCCGTACTATATAATGCA
376: CAAAAACAAGCACAAAGACGGGTCGTGCGTCCTTGAAGTGAAGAAGGTTGATGTTGAGGAGTCTATCACGTACGA
451: AGnTCAGGAAGAGTCTCCAGATGTTCATTCGAACGAATCCAATTCCTTCCAACAGGTAACATCTAGCACATCCAC
526: TTCAATACTGGAAAAAGCGTTGACGCAAGAAGGCTGAACTTTGGACTTCTTGAATTAACTTTAGGCCAAACTATT
601: ACAGAGTTGACAAGTATGGAGTGTGCTCAGAGGATTAGTTGGTGGAAGTAACTAGTCCAGAAGCTATTCAGAATT
676: AAGAACTAGAATTGAATGCAACAGCAATCAGTTTGCCCTTTCAGTTTGTGGTTTGTTTTTCTGTTGGAAACTATC
751: TCTCGGGCATGAATAAGGAATGTGTACCAAGTATTTCAGTCTTCCTCTGCTCTGTGATGTAACTCTGTGCTTCC
826: TTTCCTATACTCGCGTTGGTAATCAA TABLE 1-continued Target Polynucleotides from *Lygus Hesperus*.

SEQ ID NO:16
ilh1c.pk003.o10.f
receptor associated finger
AAGAATTGTAAATCAATATCAAAATGGAGATGATGAAGTCAGA
151: TGTCGACTGAAAAGAATGTTTGGATTCCAAGAGATCCAAAAGCTCATTAAATATAACGTAAATACTGTGCTGTCC
226: ATGGACTGGCTTGACCGTAATGCCAAAAACTGTCCGAAATGCAACGnnCCCATTCAGAAAGTCAGTGGATGTAAC
301: CATATGGTATGCTGGAAATGCAAAACATCTTTTTGCTGGCACTGCCTATGCTTTACGTGCATAGGATAGTAAGGA
376: CGTGAGATGATCCTGTAGTTACAGCTCTCTTGCCACTGACTACCTAGAAATATCGCACTAGTCATAGTCAGCCAC
451: CCTCCTCTACCTCGCCATTATCTCATTTGGGCTGTGACAAACACAAACCTCGTGTATATCTCGTATACATTACTA
526: TGTACCTTGTTTGCGCTGTGACATCTCAGGAACCCCTTGATATGAAAATTTAAGTGGTAAAAAAACTTTTTTACG
601: ATTCCGaaaaaaaaaaaaaaaaaaaaacccnactttcttgtacaaagttggcattataagaaagcattgcttatca SEQ ID NO:17
ilh1c.pk004.b8.f
lethal tumorous imaginal discs
GCCTCTCTTCAAGTTTTTGCGGTGTCGGAATGTCAAATTAAATA
151: ATTGTTCCGATCAAATTAATATGTCTAGCATACGATTTCTTAGAAAATTCAGTGGATTTAGAATCAGTGGTTTCC
226: TAGTAGTGGGGCAGTGTGGTGCGCAGAAAATTTGCAGCTTAGGTCATTTGAAATCTCAAGAGAACTCTAGTTTAC
301: TAAGATTTACCGGTGTTAGTACGAGAAATTTCCATTTGGGAGTGGCATCTCTCGCCAGAAAGACTACTACGAGA
376: TCTTGGGCATCTCTAGAAACGCGTCGGTCAAGGAAGTGAAAAAAGCGTACTATCAGCTGGCCAAGAAATACCATC
451: CAGACACGAATAAAAnnnnTCCGAACGCCGCCAAGAAGTTTCAAGAAGTATCAGAAGCCTATGAGGTACTGAGTG
526: ACGACACCAAGAGGAAACAATATGATCAATGGGGTACGACGTCGGAGCAGATGGGCCGAGAAGGTGCTGGTACAG
601: GTCCAGGTAACATGGGCGGCTTCAACTGGCAGTACCGGGCTTCCGTGGACCCTCAGGAGCTCTTCAGGAAGATCT
676: TTGGAGACGCTGCAGGCGGATTTTCCACCGGATTCGACGATTTCGCTGAGTCTAGATTCGGTCACGGTGCTGCCG
751: AAGAAATTCTAATGAAACTCACCTTCTCTCAAGCCGTGCGGGGAGTGAGCAAAGAAATATACGTTAATGt SEQ ID NO:18
ilh1c.pk004.d17.f
ribonucleoprotein
GATGATCACnTTTACGGCTAATACTCGTAGATCTCCAGTTT
151: CGATACAAATTTGAATTCAACGAGATAACCGAATGAAATGACTTGGAAATCAGCTTAAAAGCAGTGAACTCAGCG
226: GTAGAGGGGAAAATGTCTCACTCCGACTCAAGAACAGGGAAAACCTCCAGAAGTACGAATGAGTCGAAATCAGGA
301: GCCTCGGGGCGACAGAAAACTTCAAGAACTGAGCCGAAAACCCCGAAAACTGAGTCAAAAACCTCGAAGTCAGCG
376: TCGAAAACCTCGAAGTCAGAAGGGAAGTCTGTGTTGTCTGAAAGTAGAGATAAAAGTAATAAATTTTCAAAAAGC
451: GAATCTGAGTCGTATCGCAAGTCCGATGCGAGGGGACAGCGGGACGAGGCACCAGGACCGTCAGACAGCAGAACA
526: GGAAAAGACGTCACTGGGGATAGGAAAACTAAGAAACAGAAAAGTAAGAAAAGGGGTCGACGGATCTACTGGAGAA
601: TCGAAGAAACTCCCAGTGTCGTCCTCAAGAACGTCGGAAGCGCCGCGGAACATCCGAGATCTCTTGAGGAGGATC
676: AACGAGGAGAACGAATCTCAGCCAACACCTTCTTCTCGTCTGAAAGAnCCCAAGCCGGAGAGGACGAAGAGTAAA
751: GTTCCATCCAAAGCACCGCAGGCGAGTATTCCAGATAGGGACGTGGTACGAGCAAAAGCTGCGGAAncggccttg SEQ ID NO:19
ilh1c.pk004.k13.f
cathepsin; protease
GTTCACCAAGGAAGTATCGCACCACATTCTCTGCCAAAC
151: TACAGCAGGATCCCAAACCACCGGAATGAACACCATTTTGGCTCTCGCAAGTCTGTTGGGCTGCTGTCTGGCGGC
226: GTCCGTTCCGGATTCGAAGTGGGATTCTTTCAAGGCCAAATACGGAAAAACGTACGACGACCCAAAAGTCGATAG
301: TGAGAGACGTAACAACTACGGAAAAACGCTAGAGATGATCAAGGCTCACAACGCACTCTATGGACAGGGCCGGGT
376: GTCCTACTACCTGGCAGAGAACCATCTTGCAGACTTGTCGTCCAGTGAACGAATGAAGTTAAGAGGATTCAGAAA
451: ATCCGAAAGTCAATCGGGCGGCAGAATCCACCAGCACACTGGATTGGGCCGACCCGATTCCGTCGATTGGCGAAA
526: CAAAAGCGTTGTGACCAGCGTCAAAAATCAAGGACAATGTGGTAGCTGCTGGGCTTTCAGTGCGACTGCAGCAGT
601: GGAATCGCAATACGCTATCAAAACCGGGCAATTAGTGGATCTCAGCGAGCAGCAGGTAGTGGACTGTGACCGTAA
676: TGGTCACGCTTGCAAGTATGGTGACAACCTTGACGCGTTAGGGTATATCGAGGAAGAAGGTCAGGAGCTTCTTTC
751: CTCTTATCCCTACATTGCTGAGCCAGAGACTTGTCAATACGCAGCAGATAAAGTGAAGGTGAAGATTGCGAGTTT
826: CCnn SEQ ID NO:20
ilh1c.pk011.a8.f
polyprotein deformed destructor
GTCTTAAGTGATGAAGATGTTGTGTTAGGTTTACCGGG
151: CGTGCCAGGATACCATGCTATGGAAATGGCAACGTCTGAAGGTTTTCCTTTCACAGCAAGTCGACCACAAGGAAG
226: TTCCAATAAGCGGTGGTTGTTTAACATCAATGAGAATGCCGAGAAGAGATCCTTAATCGCCATGGACCCCTTATT
301: GGTGAAAGTGTTAGAATCGAAGAGGGTTCAGAGAGATCGAGGGTTGATTCCGTGTACCGTTTTTGTAGACTGCTT
376: GAAGGATTCACGAATAGCGAATGAATCTTACCTCACACCCGGTAAGACTAGGATCTTCTCTATCTCACCGGTTGA
451: CTTTACGATTGAGTTTCGGAAGTATTTCCTTGATATCCTAGCGGCGCAACAACAAAGTCGATTCCACCTAGAGCA
526: TATGGTAGGTATGAATGTTCATTCGCTTGAGTGGACTTTACTAGCCGCCGTATCCAATCTGTGGGTTCTGCAGT
601: GATCTGTGGTGATTACTCGAACTTTGGTCCTGGTTTGGATAGCGAAGTTGTTGCAGCTGTTGGGGACGTTTGGGC
676: TGATTGGTATGAGTTTTACGAGACCGCTCAGGGCGTCTCGGAAGAGGAGAGAAAGCGACGCCgccnaagtaagaa SEQ ID NO:21
ilh1c.pk011.d10.f
death associated leucine rich . . .
CATGGCGTACGGTGTAACAAGAGTCGTGTTCCGCTGCGAGGAAGCT
151: CAGGAATCCGGAnAATTGGATCTGTCGGAATGTCAACTCATGCAGGTGCCGGACGCGGTCTACCACTTGATGAGG
226: CACACGGAACTGAAGGCGTGTAATCTCTCAAGCAACGTCATCACCAAAATTCCCCCGAAATTCGCGGTCAACTTT
301: TCTCTCATTACAGAGCTGAACCTGGCGCACAACCAGATGAGCAAACTCCCGGACGAGCTCGCCG

TABLE 2

Summary of homology for the target nucleotides.

| Lygus target sequences: | Homology |
|---|---|
| ilh1c.pk005.o10.f | blastx: *melanogaster*; *drosophila*; modulatory; potassium; channel; isoform; *sapiens*; homo; *rerio*; *danio*; *anopheles*; *musculus*; *gambiae*; pe . . . <br> blastn: *melanogaster*; *drosophila*; isoform; full; insert; 85c-85c; bac; *gambiae*; str; pest; section; *anopheles*; length |
| ilh1c.pk004.e6.f | blastx: *drosophila*; *melanogaster*; *anopheles*; *gambiae*; pest; cuticle; str; *pseudoobscura*; a3a; tm-lcp; tm-a3a; larval; cuticular; tenebri . . . <br> blastn: *melanogaster*; *drosophila*; length; section; full; bac; 92e-92f |
| ilh1c.pk001.e23.f | blastx: *drosophila*; *melanogaster*; *pseudoobscura*; *anopheles*; *gambiae*; *buzzatii*; pest; str; *mellifera*; predicted; cuticle; *apis*; a3a; dbuz . . . <br> blastn: *musculus*; *mus*; bac; library; mouse; *r.norvegicus*; roswell; institute; hippocampus; product:hypothetical; female; containing; can . . . |
| ilh1c.pk010.f11.f | blastx: glycoprotein; endocuticle; structural; *drosophila*; *anopheles*; *gambiae*; *melanogaster*; *pseudoobscura*; pest; str; *mori*; *bombyx*; cut . . . <br> blastn: *melanogaster*; *drosophila*; cuticle; larval; lcp-14; *m.sexta*; constituent; asap; *sexta*; *gambiae*; *bombyx*; lcp17; *subalbatus*; *mori*; . . . |
| ilh1c.pk011.m15.f | blastx: *anopheles*; *gambiae*; pest; cuticle; str; *melanogaster*; *drosophila*; lm-acp; isoform; tm-lcp; larval; a1a; a3a; tm-a3a; tm-a1a; mel . . . <br> blastn: *anopheles*; *gambiae*; *melanogaster*; *drosophila*; pest; str; ccp84ab; cuticle; ccp84ad; ccp84ag; full; insert |
| ilh1c.pk005.d21.f | blastx: *branchiostoma*; region-containing; *floridae*; variable; chitin-binding <br> blastn: cultivar-group; *japonica*; *sativa*; *oryza*; predicted; mucin; insert; full; collagen; *norvegicus*; *discoideum*; alpha; *dictyostelium*; . . . |
| ilh1c.pk011.f4.f | blastx: *danio*; *rerio*; predicted; *melanogaster*; *anopheles*; *drosophila*; *gambiae*; chitinase; isoform; acidic; pest; str; *paralichthys*; oliv . . . <br> blastn: chitinase; predicted; *rerio*; *danio*; acidic; transcript; *taurus*; variant; *bos*; *sapiens*; b04; homo; chia; mammalian; *chitotriosida* . . . |
| ilh1c.pk004.a13.f | blastx: carboxylesterase; *gossypii*; esterase; *aphis*; carboxylic-ester; hydrolase; *persicae*; *myzus*; fe4; *lygus*; juvenile; *polyphemus*; ant . . . <br> blastn: carboxylesterase; *anisopteromalus*; *melanogaster*; *calandrae*; *drosophila*; esterase; *mellifera*; *apis*; *antheraea*; est; malathion-sus . . . |
| ilh1c.pk004.i18.f | blastx: esterase; *tribolium*; *castaneum*; *mellifera*; juvenile; carboxylic-ester; carboxylesterase; hormone; hydrolase; *apis*; *persicae*; myz . . . <br> blastn: carboxylesterase; esterase; *anisopteromalus*; *m.persicae*; *calandrae*; *anopheles*; *gambiae*; pest; est1; str; *mellifera*; desago; pred . . . |
| ilh1c.pk004.l22.f | blastx: *anopheles*; *gambiae*; *drosophila*; *melanogaster*; pest; str; *pseudoobscura*; hormone-inducible; juvenile <br> blastn: |
| ilh1c.pk005.k23.f | blastx: esterase; *tribolium*; *castaneum*; *melanogaster*; *anopheles*; *drosophila*; *gambiae*; carboxylesterase; pest; athalia; str; juvenile; ro . . . <br> blastn: |
| ilh1c.pk010.g16.f | blastx: *melanogaster*; *drosophila*; *anopheles*; *gambiae*; pest; str; jhi-26; juvenile; *yakuba*; *pseudoobscura*; hormone-inducible <br> blastn: |
| ilh1c.pk002.d16.f | blastx: vitellogenin; plautia; stali; *mellifera*; *apis*; *nipponica*; pimpla; *clavatus*; encarsia; *gambiae*; vitellogenin-1; vitellogenin-3; V . . . <br> blastn: vitellogenin; *plautia*; *aedes*; *aegypti*; *stali*; vg-b; *dictyostelium*; *discoideum*; vga1; vtg; athalia; *periplaneta*; formosa; *rosae*; . . . |
| ilh1c.pk001.f1.f | blastx: vitellogenin; *anopheles*; *gambiae*; pest; str; molitor; *encarsia*; *nigrofuscata*; toxorhynchites; graptopsaltria; quinquefasciatus; . . . <br> blastn: vitellogenin; *aedes*; vg-c; *aegypti*; polynesiensis; vitellogenin-c; graptopsaltria; *nigrofuscata* |
| ilh1c.pk005.f15.f | blastx: vitellogenin; plautia; stali; *anopheles*; vitellogenin-2; *periplaneta*; *gambiae*; *mellifera*; *americana*; *apis*; pest; str; *pimpla*; cl . . . <br> blastn: vitellogenin; *quinquefasciatus*; *dictyostelium*; *phragmatopoma*; *californica*; *discoideum*; variant; *pipiens*; cement; *oreochromis*; cu . . . |
| ilh1c.pk003.d10.f | blastx: translation; initiation; eukaryotic; gamma; structural; predicted; x-linked; *musculus*; *gallus*; unnamed; *leptinotarsa*; decemlinea . . . <br> blastn: translation; initiation; eukaryotic; structural; *musculus*; x-linked; product:eukaryotic; full-length; enriched; *mus*; library; in . . . |
| ilh1c.pk010.d2.f | blastx: *melanogaster*; *drosophila*; *anopheles*; *gambiae*; initiation; pest; str; translation; *mellifera*; *gallus*; *apis*; predicted; translatio . . . <br> blastn: |
| ilh1c.pk011.g22.f | blastx: elongation; translation; eukaryotic; beta; *anopheles*; *gambiae*; *sapiens*; synthetic; *rerio*; *danio*; pest; homo; str; construct; gal . . . <br> blastn: *anopheles*; *gambiae*; elongation; translation; eukaryotic; full-length; extremity; mosquito; beta; malaria; females; african; sing . . . |
| ilh1c.pk011.h12.f | blastx: voltage-dependent; channel; mitochondrial; *melanogaster*; *drosophila*; *anopheles*; porin; anion-selective; anion; *gambiae*; *gallus*; . . . <br> blastn: *anopheles*; *gambiae*; full-length; extremity; mosquito; malaria; females; african; 5-prime; single; adult; total; read; made; mito . . . |
| ilh1c.pk001.k13.f | blastx: mannose-6-phosphate; isomerase; phosphomannose; phosphohexomutase; *norvegicus*; *schizosaccharomyces*; *thaliana*; cultivar-group; n . . . <br> blastn: predicted; isomerase; *glabrata*; *candida*; bar1; related; other; *japonicum*; pmi40; inp51; vid28; *yarrowia*; *neurospora*; *mellifera*; . . . |

TABLE 2-continued

Summary of homology for the target nucleotides.

| Lygus target sequences: | Homology |
|---|---|
| ilh1c.pk001.k16.f | blastx: predicted; cytoplasmic; poly(a)-binding; polyadenylate; structure; *strongylocentrotus*; crystal; isoform; poly(a; x-ray; purpurat . . . <br> blastn: inducible; cytoplasmic; *sapiens*; *gallus*; poly(a; homo; form; finished; pabpc4; *aedes*; polya; asap; *aegypti*; predicted; human; tr . . . |
| ilh1c.pk001.l22.f | blastx: proteasome; non-atpase; *drosophila*; *musculus*; *melanogaster*; unnamed; isoform; macropain; 26s; *mus*; prosome; predicted; *danio*; re . . . <br> blastn: *anopheles*; *gambiae*; full-length; extremity; proteasome; non-atpase; mosquito; females; african; malaria; single; macropain; adul . . . |
| ilh1c.pk001.l4.f | blastx: <br> blastn: *sativa*; *oryza*; glycine-rich; *scapularis*; na-binding; *japonica*; *ixodes*; cultivar-group; *nipponbare*; *trospa*; cultivar; monsanto; . . . |
| ilh1c.pk001.m15.f | blastx: glutathione; s-transferase; *anopheles*; *drosophila*; *melanogaster*; *gambiae*; class-sigma; isoform; pest; allergen; str; gst; bla; s . . . <br> blastn: *melanogaster*; *drosophila*; glutathione; isoform; gsts1; *aegypti*; insert; aedes; full; extremity; glutathione-s-transferase; blatt . . . |
| ilh1c.pk001.m17.f | blastx: *drosophila*; *melanogaster*; isoform; *aegypti*; *aedes*; *pseudoobscura*; cg118; *apis*; *mellifera*; rna-binding; predicted <br> blastn: isoform; *melanogaster*; *drosophila*; vig; insert; predicted; full; mrnabp; *aedes*; asap; conserved; *ciona*; *aegypti*; *mellifera*; i29m . . . |
| ilh1c.pk001.n23.f | blastx: predicted; ankyrin; domain; repeat; *sapiens*; *musculus*; unnamed; isoform; homo; *dictyostelium*; *mus*; *discoideum*; *taurus*; *bos*; schi . . . <br> blastn: domain; *strongylocentrotus*; repeat; *purpuratus*; ankyrin; predicted;; |
| ilh1c.pk001.n6.f | blastx: *melanogaster*; *drosophila*; reticulum-type; sarco(endo)plasmic; isoform; atpase; predicted; calcium; *mellifera*; *anopheles*; *gambiae* . . . <br> blastn: sarco(endo)plasmic; reticulum-type; calcium; atpase; *melanogaster*; *mellifera*; predicted; *drosophila*; *xenopus*; ca-p60a; isoform; . . . |
| ilh1c.pk001.o17.f | blastx: *melanogaster*; *drosophila*; dyskerin; *musculus*; isoform; predicted; *gallus*; ribonucleoprotein; *mus*; *danio*; *rerio*; *anopheles*; nucle . . . <br> blastn: *melanogaster*; *drosophila*; nop60b; *lipolytica*; nucleolar; *yarrowia*; predicted; dyskerin; isoform; clib99; *purpuratus*; *danio*; ribo . . . |
| ilh1c.pk001.o4.f | blastx: *drosophila*; dehydrogenase; ubiquinone; *melanogaster*; subcomplex; nadh; beta; *anopheles*; *musculus*; unnamed; *gambiae*; predicted; 1 . . . <br> blastn: full-length; *nigroviridis*; dehydrogenase; tetraodon; ubiquinone; subcomplex; nadh; beta; asap; *musculus*; product:nadh; *danio*; re . . . |
| ilh1c.pk002.a11.f | blastx: *melanogaster*; *drosophila*; *anopheles*; *sapiens*; *gambiae*; interacting; homo; pest; str; dna-damage-inducible; gadd45gip1; papilloma . . . <br> blastn: |
| ilh1c.pk002.a24.f | blastx: voltage-dependent; channel; *drosophila*; *melanogaster*; mitochondrial; anion; isoform; porin; *sapiens*; *familiaris*; predicted; homo . . . <br> blastn: *nigroviridis*; voltage-dependent; full-length; *rerio*; *danio*; tetraodon; mitochondrial; channel; anion; *tropicalis*; *xenopus*; porin . . . |
| ilh1c.pk002.b12.f | blastx: *drosophila*; *melanogaster*; aminopeptidase-like; *anopheles*; *pseudoobscura*; *gambiae*; *bombyx*; leucyl; pest; *mori*; str; *simulans* <br> blastn: *tropicalis*; *xenopus*; aminopeptidase; leucine; *gambiae*; str; lap3-prov; finished; pest; *anopheles* |
| ilh1c.pk003.n7.f | blastx: kynurenine; aminotransferase; *drosophila*; *melanogaster*; aegypti; isoform; *aedes*; transaminase; aminotrasferase; *anopheles*; tropi . . . <br> blastn: *melanogaster*; *drosophila*; isoform; *anopheles*; *gambiae*; insert; full; single; fk0aaa5bf12; total; kynurenine; nuclear; *ciona*; ext . . . |
| ilh1c.pk003.p4.f | blastx: *drosophila*; *melanogaster*; tripeptidyl-peptidase; tripeptidyl; isoform; *pseudoobscura*; aminopeptidase; peptidase; *anopheles*; pred . . . <br> blastn: tripeptidyl; peptidase; *musculus*; product:tripeptidyl; *sapiens*; full-length; enriched; *mus*; library; homo; insert; predicted; ri . . . |
| ilh1c.pk004.c13.f | blastx: aminomethyltransferase; cleavage; *glycine*; system; *drosophila*; *melanogaster*; t-protein; structure; mitochondrial; crystal; *rerio* . . . <br> blastn: aminomethyltransferase; mitochondrial; predicted; *norvegicus*; cleavage; glycine; *rattus*; system; *debaryomyces*; gcvt; *hansenii*; c . . . |
| ilh1c.pk004.i5.f | blastx: amino-acid; predicted; synthesis; control; general; 1-like; *musculus*; gcn1; *sapiens*; homo; unnamed; *mus*; *canis*; *mellifera*; famil . . . <br> blastn: |
| ilh1c.pk001.d8.f | blastx: *drosophila*; *melanogaster*; *pseudoobscura*; isoform; *anopheles*; *gambiae*; pest; str; *simulans* <br> blastn: *melanogaster*; *drosophila*; aminopeptidase; *sapiens*; full-length; homo; full; human; length; leucine; fetal; 25-normalized; cs0df0 . . . |
| ilh1c.pk001.e10.f | blastx: e1a-stimulated; cellular; repressor; *sapiens*; unnamed; *musculus*; homo; *mus*; predicted; *anopheles*; *gambiae*; *danio*; *rerio*; *gallus*; . . . <br> blastn: product:hypothetical; aminoacyl-transfer; *musculus*; full-length; synthetases; enriched; containing; library; e1a-stimulated; ins . . . |
| ilh1c.pk001.i10.f | blastx: aminopeptidase; *musculus*; *melanogaster*; *drosophila*; unnamed; *mus*; *dictyostelium*; membrane-bound; *lycopersicon*; *discoideum*; escul . . . <br> blastn: aminopeptidase; *musculus*; membrane-bound; full-length; enriched; *mus*; library; insert; product:membrane-bound; riken; full; lyco . . . |
| ilh1c.pk010.p16.f | blastx: aminotransferase; phosphoserine; *musculus*; unnamed; *sapiens*; *mus*; isoform; homo; synthetic; construct; *mellifera*; *xenopus*; rattu . . . <br> blastn: product:phosphoserine; aminotransferase; full-length; *musculus*; *yersinia*; enriched; library; insert; *pestis*; riken; blastocyst; . . . |

TABLE 2-continued

Summary of homology for the target nucleotides.

| Lygus target sequences: | Homology |
|---|---|
| ilh1c.pk003.k14.f | blastx: carboxypeptidase; vitellogenic-like; *sapiens*; serine; homo; carboxypeptidase-like; predicted; cpvl; vitellogenic; *canis*; mellife . . .<br>blastn: full-length; 25-normalized; *sapiens*; placenta; carboxypeptidase; human; homo; cot; aegypti; aedes; troglodytes; vitellogenic; se . . . |
| ilh1c.pk004.a13.f | blastx: carboxylesterase; *gossypii*; esterase; *aphis*; carboxylic-ester; hydrolase; *persicae*; *myzus*; fe4; *lygus*; juvenile; *polyphemus*; ant . . .<br>blastn: carboxylesterase; *anisopteromalus*; *melanogaster*; *calandrae*; *drosophila*; esterase; *mellifera*; *apis*; *antheraea*; est; malathion-sus . . . |
| ilh1c.pk001.b20.f | blastx: *glycine*; decarboxylase; decarboxylating; dehydrogenase; cleavage; *melanogaster*; system; *drosophila*; *sapiens*; mitochondrial; homo . . .<br>blastn: *glycine*; decarboxylase; *melanogaster*; *drosophila*; decarboxylating; mitochondrial; dehydrogenase; cleavage; *musculus*; product:gly . . . |
| ilh1c.pk004.i18.f | blastx: esterase; *tribolium*; *castaneum*; *mellifera*; juvenile; carboxylic-ester; carboxylesterase; hormone; hydrolase; *apis*; *persicae*; myz . . .<br>blastn: carboxylesterase; esterase; *anisopteromalus*; *m.persicae*; *calandrae*; *anopheles*; *gambiae*; pest; est1; str; *mellifera*; desago; pred . . . |
| ilh1c.pk004.o2.f | blastx: carboxypeptidase; vitellogenic-like; *sapiens*; vitellogenic; serine; homo; carboxypeptidase-like; cpvl; predicted; *canis*; pygmaeu . . .<br>blastn: carboxypeptidase; *anopheles*; *gambiae*; vitellogenic; carboxypeptidase-like; full-length; vitellogenic-like; extremity; mosquito; . . . |
| ilh1c.pk005.m3.f | blastx: proteolipid; vacuolar; *drosophila*; synthase; *melanogaster*; *anopheles*; isoform; *gambiae*; kda; atp; pest; *mellifera*; str; c-subuni . . .<br>blastn: *anopheles*; *gambiae*; full-length; extremity; mosquito; malaria; african; 5-prime; females; single; total; adult; made; read; vacu . . . |
| ilh1c.pk002.o3.f | blastx: ubiquitin-specific; ubiquitin; protease; carboxyl-terminal; thiolesterase; herpesvirus; associated; n-terminal; hydrolase; usp7h . . .<br>blastn: ubiquitin-specific; protease; ubiquitin; predicted; specific; herpesvirus; associated; *musculus*; hausp; virus-associated; norveg . . . |
| ilh1c.pk003.h22.f | blastx: pyrophosphatase; *musculus*; dutp; deoxyuridine; unnamed; triphosphatase; dutpase; human; nucleotidohydrolase; *mus*; *norvegicus*; st . . .<br>blastn: *musculus*; full-length; enriched; *mus*; product:dutpase; triphosphatase; library; insert; riken; full; deoxyuridine; days; dutpase . . . |
| ilh1c.pk003.i6.f | blastx: inosine-uridine; nucleoside; hydrolase; preferring; cultivar-group; *japonica*; *sativa*; *xenopus*; *oryza*; *schizosaccharomyces*; *laevi* . . .<br>blastn: *staphylococcus*; *aureus*; subsp; *tropicalis*; *xenopus*; mw2; n315; mu50; finished; strain:mw2; mrsa252; mssa476; col |
| ilh1c.pk004.a13.f | blastx: carboxylesterase; *gossypii*; esterase; *aphis*; carboxylic-ester; hydrolase; *persicae*; *myzus*; fe4; *lygus*; juvenile; polyphe*mus*; ant . . .<br>blastn: carboxylesterase; *anisopteromalus*; *melanogaster*; *calandrae*; *drosophila*; esterase; *mellifera*; *apis*; *antheraea*; est; malathion-sus . . . |
| ilh1c.pk003.g17.f | blastx: *drosophila*; *melanogaster*; acetyltransferase; choline; *anopheles*; *gambiae*; isoform; *sapiens*; *danio*; *rerio*; predicted; structure; . . .<br>blastn: |
| ilh1c.pk009.k12.f | blastx: *drosophila*; initiation; *melanogaster*; translation; eukaryotic; predicted; *anopheles*; *gambiae*; taurus; pest; *danio*; *rerio*; str; b . . .<br>blastn: *melanogaster*; *drosophila*; translation; eukaryotic; initiation; *tropicalis*; *xenopus*; 110 kda; *rerio*; *danio*; *gambiae*; eif3s8-prov; . . . |
| ilh1c.pk009.f20.f | blastx: eif4g-related; *danio*; *rerio*; predicted; nat1b; isoform; *xenopus*; translation; initiation; eukaryotic; *tropicalis*; *gallus*; gamma; . . .<br>blastn: *melanogaster*; *drosophila*; eif4g-related; predicted; isoform; *xenopus*; *laevis*; nat1; translation; *mellifera*; 49e-49f; full; eukar . . . |
| ilh1c.pk008.o12.f | blastx: translationally; translationally-controlled; controlled; *drosophila*; tumor; *melanogaster*; *mellifera*; predicted; *anopheles*; tctp; . . .<br>blastn: *drosophila*; *melanogaster*; translationally; controlled; *anopheles*; *gambiae*; tumor; tctp; *lonomia*; *bombyx*; *xylostella*; african; in . . . |
| ilh1c.pk008.k5.f | blastx: elongation; *rhodopseudomonas*; *palustris*; translation; *bradyrhizobium*; *melanogaster*; gtp-binding; *drosophila*; tu:small; domain; m . . .<br>blastn: *melanogaster*; *drosophila*; elongation; insert; *rerio*; *danio*; full; *brevipalpis*; asap; *gambiae*; translation; *wigglesworthia*; marit . . . |
| ilh1c.pk008.c24.f | blastx: translation; eukaryotic; initiation; interacting; *sapiens*; *melanogaster*; *drosophila*; homo; predicted; *familiaris*; isoform; varia . . .<br>blastn: full-length; 25-normalized; *sapiens*; human; placenta; homo; cot; interacting; translation; eukaryotic; initiation; *danio*; *rerio*; . . . |
| ilh1c.pk008.b15.f | blastx: *melanogaster*; *musculus*; *drosophila*; predicted; unnamed; *anopheles*; translation; *mus*; *gambiae*; *sapiens*; pest; riken; *rerio*; *danio* . . .<br>blastn: *sapiens*; *melanogaster*; *drosophila*; homo; translation; *danio*; *rerio*; et16; fis; length; *taurus*; *bos*; spliced; alternatively; tran . . . |
| ilh1c.pk007.p11.f | blastx: translation; initiation; eukaryotic; *drosophila*; *melanogaster*; *anopheles*; *gambiae*; *bombyx*; eif-5a; pest; *spodoptera*; *danio*; reri . . .<br>blastn: initiation; translation; eukaryotic; *norvegicus*; *thaliana*; *bombyx*; eif5a; *mori*; *rerio*; *danio*; eif-5a; 5a-4; gsltsil10za11; thal . . . |

TABLE 2-continued

Summary of homology for the target nucleotides.

| Lygus target sequences: | Homology |
| --- | --- |
| ilh1c.pk003.d10.f | blastx: translation; initiation; eukaryotic; gamma; structural; predicted; x-linked; *musculus*; *gallus*; unnamed; *leptinotarsa*; decemlinea . . .<br>blastn: translation; initiation; eukaryotic; structural; *musculus*; x-linked; product: eukaryotic; full-length; enriched; *mus*; library; in . . .<br>blastn: domain; *strongylocentrotus*; repeat; *purpuratus*; ankyrin; predicted; *schistosoma*; *japonicum*<br>blastn: sarco(endo)plasmic; reticulum-type; calcium; atpase; *melanogaster*; *mellifera*; predicted; *drosophila*; *xenopus*; ca-p60a; isoform; . . . |
| ilh1c.pk002.d16.f | blastx: vitellogenin; plautia; stali; *mellifera*; *apis*; *nipponica*; *pimpla*; *clavatus*; *encarsia*; *gambiae*; vitellogenin-1; vitellogenin-3; v . . .<br>blastn: vitellogenin; plautia; aedes; aegypti; stali; vg-b; *dictyostelium*; *discoideum*; vga1; vtg; athalia; *periplaneta*; formosa; rosae; . . . |
| ilh1c.pk002.d9.f | blastx: coiled-coil-helix-coiled-coil-helix; containing; predicted; domain; *sapiens*; *musculus*; homo; chchd4; *anopheles*; *norvegicus*; gamb . . .<br>blastn: coiled-coil-helix-coiled-coil-helix; containing; predicted; domain; *gallus*; *norvegicus*; *rattus*; *rerio*; *danio*; chchd4; *musculus*; . . . |
| ilh1c.pk002.j6.f | blastx: transmembrane; predicted; *sapiens*; *tropicalis*; homo; *xenopus*; *musculus*; *gallus*; *norvegicus*; *mus*; *rattus*; *danio*; *canis*; *rerio*; te . . .<br>blastn: |
| ilh1c.pk002.k17.f | blastx: proteasome; *drosophila*; regulatory; *melanogaster*; isoform; *musculus*; non-atpase; 26s; unnamed; predicted; *mus*; *anopheles*; *gambia* . . .<br>blastn: proteasome; regulatory; *melanogaster*; *drosophila*; predicted; 26s; *anopheles*; transcript; non-atpase; *gambiae*; isoform; variant; . . . |
| ilh1c.pk002.k5.f | blastx: nucleoporin; *sapiens*; homo; predicted; unnamed; 54 kda; *familiaris*; p54; variant; isoform; kda; *canis*; *musculus*; macaca; *apis*; fa . . .<br>blastn: nucleoporin; product: nucleoporin; full-length; *musculus*; enriched; *norvegicus*; library; insert; riken; *rattus*; *mus*; full; macrop . . . |
| ilh1c.pk002.m21.f | blastx: rapamycin-insensitive; predicted; companion; *sapiens*; *musculus*; mtor; homo; insensitive; pianissimo; rapamycin; *mus*; rictor; gal . . .<br>blastn: |
| ilh1c.pk002.n11.f | blastx: *melanogaster*; *drosophila*; 6-phosphofructo-2-kinase; isoform; 2,6-bisphosphatase; fructose-2,6-biphosphatase; predicted; fructose . . .<br>blastn: *melanogaster*; *drosophila*; isoform; pfrx; fructose; long; full; form; insert; 6-phosphofructo; str; 2-kinase; pest; 2,6-bisphosph . . . |
| ilh1c.pk003.d10.f | blastx: translation; initiation; eukaryotic; gamma; structural; predicted; x-linked; *musculus*; *gallus*; unnamed; *leptinotarsa*; decemlinea . . .<br>blastn: translation; initiation; eukaryotic; structural; *musculus*; x-linked; product: eukaryotic; full-length; enriched; *mus*; library; in . . . |
| ilh1c.pk003.d17.f | blastx: mitochondrial; translocase; membrane; inner; predicted; import; *melanogaster*; *musculus*; *drosophila*; *anopheles*; isoform; tim9; ga . . .<br>blastn: *nigroviridis*; full-length; tetraodon; mitochondrial; translocase; membrane; *gallus*; tim9a; inner; *gambiae*; *purpuratus*; *danio*; fi . . . |
| ilh1c.pk003.h22.f | blastx: pyrophosphatase; *musculus*; dutp; deoxyuridine; unnamed; triphosphatase; dutpase; human; nucleotidohydrolase; *mus*; *norvegicus*; st . . .<br>blastn: *musculus*; full-length; enriched; *mus*; product: dutpase; triphosphatase; library; insert; riken; full; deoxyuridine; days; dutpase . . . |
| ilh1c.pk003.j5.f | blastx: benzodiazepine; receptor; peripheral-type; benzodiazapine; peripheral; *sapiens*; *musculus*; homo; construct; synthetic; unnamed; m . . .<br>blastn: |
| ilh1c.pk003.j7.f | blastx: finger; *melanogaster*; zinc; *drosophila*; *musculus*; *sapiens*; predicted; ozf; pygmaeus; homo; *mus*; *pongo*; unnamed; *taurus*; *bos*; imp . . .<br>blastn: *sapiens*; finger; zinc; homo; predicted; highly; *gallus*; *anopheles*; fis; *rerio*; *danio*; *gambiae*; pest; str; zscan2; 75a; variant; . . . |
| ilh1c.pk003.l11.f | blastx: transmembrane; inducible; *musculus*; hormone; growth; *gallus*; unnamed; *mus*; *norvegicus*; *anopheles*; pygmaeus; *xenopus*; *gambiae*; ra . . .<br>blastn: transmembrane; product: growth; *musculus*; inducible; full-length; hormone; enriched; library; insert; riken; *mus*; full; growth; o . . . |
| ilh1c.pk003.l18.f | blastx: ubiquitin; polyubiquitin; *musculus*; isoform; *familiaris*; *mus*; predicted; *sapiens*; *taurus*; *canis*; homo; *bos*; caballus; schistosom . . .<br>blastn: polyubiquitin; *norvegicus*; *rattus*; ubiquitin; *taeniopygia*; variant; *guttata*; 7-like; pub; *trifallax*; ubiquitins; ttu3; sterkiell . . . |
| ilh1c.pk003.o10.f | blastx: receptor-associated; finger; androgen; predicted; triad2; ring; *musculus*; caenorhabditis; hfb30; isoform; unnamed; *mus*; *taurus*; . . .<br>blastn: ubiquitin-conjugating; *rerio*; *danio*; ariadne; predicted |
| ilh1c.pk004.b8.f | blastx: *melanogaster*; *drosophila*; lethal(2)tumorous; isoform; imaginal; discs; tid56; mitochondrial; tumorous; l(2)tid; tid58; tid50; br . . .<br>blastn: *musculus*; full-length; subfamily; *anopheles*; product: dnaj; member; *gambiae*; *mus*; hsp40; enriched; adult; library; alternatively; . . . |
| ilh1c.pk004.d17.f | blastx: nucleolar; cerevisiae; assembly; polymerase; *laevis*; function; suppressor; ac40; srp40p; *purpuratus*; snornps; ribonucleoprotein; . . .<br>blastn: |
| ilh1c.pk004.e16.f | blastx: disrupted; disorder; *musculus*; *drosophila*; bipolar; predicted; *melanogaster*; unnamed; *mus*; *familiaris*; isoform; *canis*; asparagin . . .<br>blastn: *musculus*; disorder; disrupted; bipolar; full-length; *sapiens*; enriched; homo; library; *mus*; predicted; human; insert; asparagine . . . |

TABLE 2-continued

Summary of homology for the target nucleotides.

| Lygus target sequences: | Homology |
|---|---|
| ilh1c.pk004.g2.f | blastx: benzodiazepine; receptor; peripheral-type; *musculus*; mitochondrial; unnamed; *mus*; peripheral; isoquinoline-binding; pkbs; pbr; t . . .<br>blastn: |
| ilh1c.pk004.k13.f | blastx: cathepsin; proteinase; cysteine; l-like; *sapiens*; *scrofa*; homo; *heterodera*; *glutinosa*; *globodera*; *glycines*; *pallida*; sus; myxine . . .<br>blastn: cysteine; decemlineata; *leptinotarsa*; proteinase; intestain; digestive; cathepsin; *sapiens*; *h.americanus*; preproenzyme; homo; vi . . . |
| ilh1c.pk004.m4.f | blastx: unc-51-like; *sapiens*; kinase; predicted; *musculus*; homo; isoform; unnamed; *gallus*; *taurus*; *mus*; ulk3; *bos*; *xenopus*; *mellifera*; l . . .<br>blastn: *melanogaster*; *drosophila*; *musculus*; predicted; product: hypothetical; kinase; insert; full; full-length; unc-51-like; containing; . . . |
| ilh1c.pk005.a7.f | blastx: cathepsin; *caenorhabditis*; *rerio*; *danio*; *elegans*; procathepsin; *tuberaphis*; b-s; rat; *olivaceus*; *fundulus*; *heteroclitus*; paralic . . .<br>blastn: full-length; *sapiens*; homo; human; 25-normalized; placenta; construct; synthetic; cathepsin; cot; ctsb; jurkat; brain; cells; ce . . . |
| ilh1c.pk005.h9.f | blastx: nucleolar; snornp-associated; interacting; small; predicted; ribonucleoproptein-associated; 55-kda; *musculus*; *sapiens*; *rerio*; da . . .<br>blastn: |
| ilh1c.pk005.i1.f | blastx: *melanogaster*; *drosophila*; adenosine; deaminase; rna-specific; double-stranded; isoform; pre-mrna; editing; *purpuratus*; that; pre . . .<br>blastn: |
| ilh1c.pk005.i10.f | blastx: *taurus*; precystatin; *bos*; cystatin; hemorrhage; angiopathy; bovine; unnamed; cerebral; amyloid<br>blastn: |
| ilh1c.pk005.i12.f | blastx: polyphosphate; *anopheles*; multikinase; *drosophila*; inositol; *melanogaster*; *gambiae*; pest; *musculus*; str; predicted; *mus*; *canis*; . . .<br>blastn: *melanogaster*; *drosophila*; 21d-21e; insert; section; full; ipk2; bac |
| ilh1c.pk005.i15.f | blastx: cytochrome; *melanogaster*; *drosophila*; *periplaneta*; *fuliginosa*; *migratoria*; *dimidiata*; *triatoma*; *locusta*; *caretta*; *quadriocellata* . . .<br>blastn: mitochondrial; cytochrome; *blackburnia*; cytb; isolate; *gerris*; *insularis*; *gracilicornis*; jk041; jk042; jk045; *migratoria*; latiab . . . |
| ilh1c.pk005.i16.f | blastx: domain-containing; *sapiens*; dnaj; homo; novel; subfamily; *anopheles*; *norvegicus*; hsp40; predicted; *gambiae*; *gallus*; *rattus*; memb . . .<br>blastn: dnaj-1; *drosophila*; *nigroviridis*; full-length; tetraodon; predicted; prokaryotic; *norvegicus*; simulans; domain; *rerio*; *danio*; sh . . . |
| ilh1c.pk005.m3.f | blastx: proteolipid; vacuolar; *drosophila*; synthase; *melanogaster*; *anopheles*; isoform; *gambiae*; kda; atp; pest; mellifema; str; c-subuni . . .<br>blastn: *anopheles*; *gambiae*; full-length; extremity; mosquito; malaria; african; 5-prime; females; single; total; adult; made; read; vacu . . . |
| ilh1c.pk005.o17.f | blastx: cathepsin; *rerio*; *danio*; *virgifera*; b-like; protease; *ventricosus*; *branchiostoma*; *olivaceus*; *paralichthys*; parcxpwnx02; *lugens*; . . .<br>blastn: product: cathepsin; full-length; enriched; *musculus*; library; insert; riken; full; cathepsin; *mus*; macrophage; synthetic; constru . . . |
| ilh1c.pk006.c6.f | blastx: vesicle-associated; membrane; vamp-associated; protein-associated; predicted; *tropicalis*; *xenopus*; associated; *rerio*; *danio*; iso . . .<br>blastn: |
| ilh1c.pk006.f2.f | blastx: receptor-associated; finger; predicted; isoform; ring; *sapiens*; androgen; unnamed; homo; *xenopus*; *nigroviridis*; triad2; rnf4-pr . . .<br>blastn: |
| ilh1c.pk007.a8.f | blastx: membrane-associated; finger; *drosophila*; *melanogaster*; ring; *gallus*; *musculus*; c3hc4; predicted; *anopheles*; *gambiae*; *taurus*; mus . . .<br>blastn: *ciona*; full; insert; *intestinalis* |
| ilh1c.pk007.b21.f | blastx: phosphoprotein; golgi-localized; golgi; predicted; calcium-binding; *musculus*; isoform; *familiaris*; membrane; *mus*; *gallus*; anophe . . .<br>blastn: |
| ilh1c.pk007.g16.f | blastx: *burkholderia*; *pseudomallei*; membrane; outer; *mallei*; hep_hag; family; atcc; s13; exported; aut TABLE 2-continued Summary of homology for the target nucleotides.

| Lygus target sequences: | Homology |
|---|---|
| ilh1c.pk008.f16.f | blastx: carboxypeptidase; *melanogaster*; *drosophila*; *ochlerotatus*; *aedes*; *anopheles*; *gambiae*; aegypti; pest; str; fluid; polynesiensis; c . . . <br> blastn: carboxypeptidase; *bombyx*; fluid; mf-cpa; *mori*; molting; cpb-i; *ochlerotatus*; *triseriatus* |
| ilh1c.pk008.h14.f | blastx: signalosome; cop9; *musculus*; predicted; isoform; *mus*; photomorphogenic; complex; *xenopus*; constitutive; *norvegicus*; *norvegicus*; . . . <br> blastn: predicted; photomorphogenic; constitutive; *norvegicus*; *norvegicus*; *thaliana*; *rattus*; cop9; *mellifera*; cops8_predicted; apis |
| ilh1c.pk008.j3.f | blastx: receptor; benzodiazepine; benzodiazapine; peripheral; *musculus*; peripheral-type; unnamed; synthetic; construct; *mus*; *sapiens*; mi . . . <br> blastn: *anopheles*; *gambiae*; full-length; extremity; mosquito; african; malaria; females; single; total; adult; read; made; fk0aaa40cb05; . . . |
| ilh1c.pk008.k6.f | blastx: predicted; upstream; element; *musculus*; fuse; isoform; far; *anopheles*; *gambiae*; unnamed; *mus*; *taurus*; *rerio*; *danio*; pest; str; b . . . <br> blastn: *musculus*; regulatory; splicing; library; full-length; enriched; *mus*; product: kh-type; insert; kh-type; riken; *norvegicus*; full; . . . |
| ilh1c.pk009.d7.f | blastx: transcriptional; transcription; repressor; potential; isoform; *sapiens*; ccr4-not; complex; predicted; not4hp; homo; ccr4-associa . . . <br> blastn: *melanogaster*; *drosophila*; isoform; *mellifera*; predicted; *apis*; homo; not4-n; insert; not4-np; full; *sapiens* |
| ilh1c.pk009.f20.f | blastx: eif4g-related; *danio*; *rerio*; predicted; nat1b; isoform; *xenopus*; translation; initiation; eukaryotic; *tropicalis*; *gallus*; gamma; . . . <br> blastn: *melanogaster*; *drosophila*; eif4g-related; predicted; isoform; *xenopus*; *laevis*; nat1; translation; *mellifera*; 49e-49f; full; eukar . . . |
| ilh1c.pk010.f11.f | blastx: glycoprotein; endocuticle; structural; *drosophila*; *anopheles*; *gambiae*; *melanogaster*; *pseudoobscura*; pest; str; *mori*; *bombyx*; cut . . . <br> blastn: *melanogaster*; *drosophila*; cuticle; larval; lcp-14; *m.sexta*; constituent; asap; *sexta*; *gambiae*; *bombyx*; lcp17; *subalbatus*; *mori*; . . . |
| ilh1c.pk010.i24.f | blastx: receptor; benzodiazepine; benzodiazapine; peripheral; peripheral-type; *musculus*; *sapiens*; mitochondrial; *drosophila*; unnamed; co . . . <br> blastn: |
| ilh1c.pk010.m17.f | blastx: ntf2-related; *drosophila*; *melanogaster*; *anopheles*; export; *gambiae*; pest; predicted; *musculus*; str; nxt1; *mus*; apis; *canis*; mell . . . <br> blastn: ntf2-related; export; *sapiens*; *anopheles*; predicted; *gambiae*; ntf2-like; homo; pest; *strongylocentrotus*; str; nxt1; transcript; . . . |
| ilh1c.pk010.n4.f | blastx: receptor; delta; signal; translocon-associated; *sapiens*; construct; synthetic; homo; *rerio*; *danio*; *anopheles*; predicted; *gambiae* . . . <br> blastn: *sapiens*; receptor; synthetic; construct; delta; signal; homo; translocon-associated; 25-normalized; full-length; ssr4; placenta; . . . |
| ilh1c.pk011.a8.f | blastx: polyprotein; deformed; wing; *destructor*; sacbrood; nonstructural; *varroa*; kakugo; unnamed; *venturia*; rna-dependent; homo; sapien . . . <br> blastn: deformed; polyprotein; wing; isolate; nonstructural; fis; homo; *sapiens*; kakugo; *varroa*; *destructor* |
| ilh1c.pk011.d10.f | blastx: *drosophila*; *melanogaster*; death-associated; leucine-rich; containing; cytoplasmic; *caenorhabditis*; *anopheles*; leucine; repeat; g . . . <br> blastn: death-associated; leucine-rich; cytoplasmic; small; sclp; predicted; *sexta*; *gambiae*; str; manduca; *mellifera*; pest; *apis*; anophe . . . |
| ilh1c.pk011.e16.f | blastx: mediator; transcription; polymerase; *drosophila*; predicted; *musculus*; *melanogaster*; complex; *sapiens*; *anopheles*; *mus*; soh1; homo . . . <br> blastn: *nigroviridis*; full-length; tetraodon; *melanogaster*; *drosophila*; isoform; med31; full; insert |
| ilh1c.pk009.d7.f | blastx: transcriptional; transcription; repressor; potential; isoform; *sapiens*; ccr4-not; complex; predicted; not4hp; homo; ccr4-associa . . . <br> blastn: *melanogaster*; *drosophila*; isoform; *mellifera*; predicted; *apis*; homo; not4-n; insert; not4-np; full; *sapiens* |
| ilh1c.pk003.d10.f | blastx: translation; initiation; eukaryotic; gamma; structural; predicted; x-linked; *musculus*; *gallus*; unnamed; *leptinotarsa*; decemlinea . . . <br> blastn: translation; initiation; eukaryotic; structural; *musculus*; x-linked; product: eukaryotic; full-length; enriched; *mus*; library; in . . . |
| ilh1c.pk003.f22.f | blastx: transcription; upstream; predicted; nucleolar; *danio*; *rerio*; isoform; ubf-1; autoantigen; nor-90; ubtf; unnamed; human; polymera . . . <br> blastn: |
| ilh1c.pk004.e16.f | blastx: disrupted; disorder; *musculus*; *drosophila*; bipolar; predicted; *melanogaster*; unnamed; *mus*; *familiaris*; isoform; *canis*; asparagin . . . <br> blastn: *musculus*; disorder; disrupted; bipolar; full-length; *sapiens*; enriched; homo; library; *mus*; predicted; human; insert; *asparagine* . . . |
| ilh1c.pk004.m22.f | blastx: spinocerebellar; predicted; ataxin; ataxin-7; ataxia; *sapiens*; *familiaris*; *gallus*; *musculus*; isoform; homo; *canis*; *norvegicus*; r . . . <br> blastn: |
| ilh1c.pk005.l24.f | blastx: *melanogaster*; *drosophila*; isoform; *anopheles*; *gambiae*; caenorhabditis; pest; str; *elegans*; predicted; f-box; leucine-rich; lrr-r . . . <br> blastn: *melanogaster*; *drosophila*; isoform; full; bac; clones; asap; conserved; *mellifera*; *apis*; aegypti; predicted; *aedes*; 99b-99b; sect . . . |

TABLE 2-continued

Summary of homology for the target nucleotides.

| Lygus target sequences: | Homology |
|---|---|
| ilh1c.pk006.c15.f | blastx: *caenorhabditis*; calpain; *anopheles*; *elegans*; *gambiae*; family; *gallus*; calcium-activated; pest; str; isoform; *xenopus*; neutral; m . . .<br>blastn: calpain; *musculus*; ncl-4; *sapiens*; tract-specific; product: calpain; homo; *mus*; transcript; full-length; capn9; digestive; enrich . . . |
| ilh1c.pk001.f20.f | blastx: *caenorhabditis*; *elegans*; predicted; *schistosoma*; rna-directed; transcriptase; polymerase; containing; polyprotein; *rerio*; *danio*; . . .<br>blastn: *caenorhabditis*; zebrafish; linkage; *elegans*; group; ch211-12p12; ch211-260p11; dkey-9p20 |
| ilh1c.pk006.c6.f | blastx: vesicle-associated; membrane; vamp-associated; protein-associated; predicted; *tropicalis*; *xenopus*; associated; *rerio*; *danio*; iso . . .<br>blastn: |
| ilh1c.pk001.h3.f | blastx: *drosophila*; *melanogaster*; proteinase; *sarcophaga*; 26, 29 kda; homologue; predicted; *anopheles*; *gambiae*; *gallus*; *danio*; *rerio*; pest . . .<br>blastn: *anopheles*; *gambiae*; proteinase; *sarcophaga*; 26, 29 kda; *melanogaster*; full-length; *drosophila*; homologue; extremity; mosquito; afr . . . |
| ilh1c.pk007.c6.f | blastx: predicted; containing; armadillo; *sapiens*; repeat; homo; *strongylocentrotus*; *purpuratus*; *anopheles*; novel; *gambiae*; pest; str; n . . .<br>blastn: *musculus*; complex; cultivar-group; product: adaptor-related; *mus*; adaptor-related; *japonica*; beta; *sativa*; full-length; *oryza*; en . . . |
| ilh1c.pk007.m5.f | blastx: transcription; polypeptide; general; *sapiens*; *musculus*; 63 kda; homo; *gallus*; iiic; iiic-epsilon; tf3c-epsilon; *mus*; *anopheles*; t . . .<br>blastn: |
| ilh1c.pk008.c24.f | blastx: translation; eukaryotic; initiation; interacting; *sapiens*; *melanogaster*; *drosophila*; homo; predicted; *familiaris*; isoform; varia . . .<br>blastn: full-length; 25-normalized; *sapiens*; human; placenta; homo; cot; interacting; translation; eukaryotic; initiation; *danio*; *rerio*; . . . |
| ilh1c.pk008.d5.f | blastx: prostaglandin; prostaglandin-endoperoxide; synthase; synthase-2; cyclooxygenase-2; cox-2; *taurus*; *familiaris*; *tropicalis*; caball . . .<br>blastn: prostaglandin; synthase; *gallus*; *rerio*; predicted; *c.porcellus*; *danio*; cyclooxygenase-2; chicken |
| ilh1c.pk008.f17.f | blastx: cathepsin; proteinase; b-like; e.c.3.4.22.1; *schistosoma*; papain-like; *virgifera*; lysosomal; isotype; *mansoni*; *triatoma*; sm31; d . . .<br>blastn: cathepsin; *sapiens*; construct; synthetic; homo; 25-normalized; ctsb; full-length; human; *pygmaeus*; placenta; *pongo*; cot; cs0di02 . . . |
| ilh1c.pk008.g3.f | blastx: pyroglutamyl-peptidase; pyrrolidone-carboxylate; unnamed; *musculus*; 5-oxoprolyl-peptidase; *norvegicus*; peptidase; *xenopus*; sapie . . .<br>blastn: |
| ilh1c.pk002.o12.f | blastx: *anopheles*; *gambiae*; trypsin; pest; str; protease; trypsin-related; chymotrypsin; *aegypti*; *aedes*; chymotrypsin-like; ctenocephali . . .<br>blastn: |
| ilh1c.pk003.d10.f | blastx: translation; initiation; eukaryotic; gamma; structural; predicted; x-linked; *musculus*; *gallus*; unnamed; *leptinotarsa*; decemlinea . . .<br>blastn: translation; initiation; eukaryotic; structural; *musculus*; x-linked; product: eukaryotic; full-length; enriched; *mus*; library; in . . . |
| ilh1c.pk004.o2.f | blastx: carboxypeptidase; vitellogenic-like; *sapiens*; vitellogenic; serine; homo; carboxypeptidase-like; cpvl; predicted; *canis*; pygmaeu . . .<br>blastn: carboxypeptidase; *anopheles*; *gambiae*; vitellogenic; carboxypeptidase-like; full-length; vitellogenic-like; extremity; mosquito; . . . |

TABLE 3

Summary of Top Blast Hit

| sid | database | accession# | score |
|---|---|---|---|
| ilh1c.pk005.o10.f | gb | AAL28614.1 | 498 |
| ilh1c.pk004.e6.f | gb | EAA04403.2 | 161 |
| ilh1c.pk001.e23.f | gb | EAA04403.2 | 160 |
| ilh1c.pk010.f11.f | sp | Q7M4F2 | 359 |
| ilh1c.pk011.m15.f | sp | P83995 | 300 |
| ilh1c.pk005.d21.f | gb | AAN62848.1 | 104 |
| ilh1c.pk011.f4.f | gb | EAA06494.2 | 559 |
| ilh1c.pk004.a13.f | gb | AAT09370.1 | 634 |
| ilh1c.pk004.i18.f | gb | AAT09370.1 | 648 |
| ilh1c.pk004.l22.f | gb | EAA03540.3 | 275 |
| ilh1c.pk005.k23.f | gb | AAT09370.1 | 377 |
| ilh1c.pk010.g16.f | gb | EAA08488.2 | 148 |
| ilh1c.pk002.d16.f | dbj | BAA22791.1 | 567 |
| ilh1c.pk001.f1.f | dbj | BAA22791.1 | 321 |
| ilh1c.pk005.f15.f | gb | AAB72001.1 | 245 |
| ilh1c.pk003.d10.f | emb | CAF92618.1 | 196 |
| ilh1c.pk010.d2.f | gb | AAF56796.2 | 188 |
| ilh1c.pk010.d2.f | gb | AAM50998.1 | 188 |
| ilh1c.pk011.g22.f | ref | XP_625027.1 | 437 |
| ilh1c.pk011.h12.f | gb | AAT01080.1 | 744 |
| ilh1c.pk001.k13.f | ref | XP_623842.1 | 477 |
| ilh1c.pk001.k16.f | ref | XP_396057.2 | 508 |
| ilh1c.pk001.k16.f | ref | XP_623167.1 | 508 |
| ilh1c.pk001.l22.f | ref | XP_392692.2 | 673 |
| ilh1c.pk001.m15.f | gb | AAV31410.1 | 583 |
| ilh1c.pk001.m17.f | ref | XP_392925.2 | 390 |
| ilh1c.pk001.n23.f | ref | XP_790997.1 | 235 |
| ilh1c.pk001.n6.f | gb | AAD09820.1 | 384 |
| ilh1c.pk001.o17.f | gb | AAL90146.1 | 758 |
| ilh1c.pk001.o17.f | gb | AAX52682.1 | 758 |
| ilh1c.pk001.o4.f | gb | EAA04597.2 | 302 |
| ilh1c.pk001.o4.f | gb | EAL32669.1 | 302 |
| ilh1c.pk002.a11.f | gb | EAA05241.2 | 189 |
| ilh1c.pk002.a24.f | gb | AAT01080.1 | 436 |
| ilh1c.pk002.b12.f | gb | EAA01140.2 | 269 |
| ilh1c.pk003.n7.f | ref | NP_788640.1 | 760 |

TABLE 3-continued

Summary of Top Blast Hit

| sid | database | accession# | score |
|---|---|---|---|
| ilh1c.pk003.p4.f | ref | XP_395521.2 | 340 |
| ilh1c.pk004.c13.f | gb | EAL33114.1 | 538 |
| ilh1c.pk004.i5.f | ref | XP_392968.2 | 323 |
| ilh1c.pk001.d8.f | gb | EAA12913.3 | 565 |
| ilh1c.pk001.e10.f | ref | NP_001007306.1 | 255 |
| ilh1c.pk001.i10.f | ref | XP_635611.1 | 284 |
| ilh1c.pk010.p16.f | ref | XP_396126.2 | 278 |
| ilh1c.pk003.k14.f | ref | XP_854245.1 | 403 |
| ilh1c.pk004.a13.f | gb | AAT09370.1 | 634 |
| ilh1c.pk001.b20.f | gb | AAF54512.1 | 741 |
| ilh1c.pk004.i18.f | gb | AAT09370.1 | 648 |
| ilh1c.pk004.o2.f | gb | AAC41580.1 | 502 |
| ilh1c.pk004.o2.f | ref | XP_854245.1 | 502 |
| ilh1c.pk005.m3.f | emb | CAA46187.1 | 706 |
| ilh1c.pk005.m3.f | sp | P55277 | 706 |
| ilh1c.pk002.o3.f | ref | XP_392848.2 | 561 |
| ilh1c.pk003.h22.f | ref | XP_393899.1 | 331 |
| ilh1c.pk003.i6.f | gb | AAI08879.1 | 238 |
| ilh1c.pk004.a13.f | gb | AAT09370.1 | 634 |
| ilh1c.pk003.g17.f | gb | EAA14743.2 | 158 |
| ilh1c.pk009.k12.f | ref | XP_623580.1 | 583 |
| ilh1c.pk009.f20.f | ref | XP_394628.2 | 332 |
| ilh1c.pk008.o12.f | dbj | BAD52260.1 | 711 |
| ilh1c.pk008.k5.f | gb | EAA09467.2 | 366 |
| ilh1c.pk008.c24.f | ref | XP_624438.1 | 804 |
| ilh1c.pk008.b15.f | gb | EAA06364.2 | 466 |
| ilh1c.pk007.p11.f | gb | ABA54998.1 | 231 |
| ilh1c.pk003.d10.f | emb | CAF92618.1 | 196 |
| ilh1c.pk002.d16.f | dbj | BAA22791.1 | 567 |
| ilh1c.pk002.d9.f | gb | EAA44856.2 | 233 |
| ilh1c.pk002.j6.f | gb | AAY24048.1 | 120 |
| ilh1c.pk002.j6.f | ref | NP_938017.1 | 120 |
| ilh1c.pk002.k17.f | gb | EAA01750.2 | 528 |
| ilh1c.pk002.k5.f | dbj | BAA91735.1 | 239 |
| ilh1c.pk002.k5.f | dbj | BAD97072.1 | 239 |
| ilh1c.pk002.k5.f | dbj | BAE01389.1 | 239 |
| ilh1c.pk002.k5.f | gb | AAF67488.1 | 239 |
| ilh1c.pk002.k5.f | gb | AAH12559.1 | 239 |
| ilh1c.pk002.k5.f | ref | NP_059122.2 | 239 |
| ilh1c.pk002.m21.f | ref | XP_425021.1 | 404 |
| ilh1c.pk002.n11.f | gb | EAA00451.2 | 968 |
| ilh1c.pk003.d10.f | emb | CAF92618.1 | 196 |
| ilh1c.pk003.d17.f | gb | EAA06794.2 | 348 |
| ilh1c.pk003.h22.f | ref | XP_393899.1 | 331 |
| ilh1c.pk003.j5.f | gb | AAK31586.1 | 153 |
| ilh1c.pk003.j7.f | gb | AAY51599.1 | 268 |
| ilh1c.pk003.j7.f | ref | NP_650534.1 | 268 |
| ilh1c.pk003.l11.f | emb | CAG31191.1 | 245 |
| ilh1c.pk003.l18.f | ref | NP_066289.2 | 321 |
| ilh1c.pk003.o10.f | ref | XP_624683.1 | 196 |
| ilh1c.pk004.b8.f | ref | XP_394833.1 | 546 |
| ilh1c.pk004.d17.f | gb | AAA35091.1 | 115 |
| ilh1c.pk004.d17.f | gb | AAH84355.1 | 115 |
| ilh1c.pk004.d17.f | ref | NP_013018.1 | 115 |
| ilh1c.pk004.e16.f | ref | XP_397356.2 | 317 |
| ilh1c.pk004.g2.f | gb | EAL33487.1 | 94 |
| ilh1c.pk004.g2.f | ref | XP_531704.2 | 94 |
| ilh1c.pk004.k13.f | gb | AAY45870.1 | 381 |
| ilh1c.pk004.m4.f | ref | XP_396911.2 | 421 |
| ilh1c.pk005.a7.f | gb | AAB65345.1 | 257 |
| ilh1c.pk005.h9.f | ref | XP_787944.1 | 119 |
| ilh1c.pk005.i1.f | gb | EAL32477.1 | 120 |
| ilh1c.pk005.i10.f | pir | UDBO | 105 |
| ilh1c.pk005.i10.f | ref | NP_776454.1 | 105 |
| ilh1c.pk005.i12.f | gb | EAA03479.2 | 394 |
| ilh1c.pk005.i15.f | gb | AAG31619.1 | 827 |
| ilh1c.pk005.i16.f | ref | XP_395584.2 | 731 |
| ilh1c.pk005.m3.f | emb | CAA46187.1 | 706 |
| ilh1c.pk005.m3.f | sp | P55277 | 706 |
| ilh1c.pk005.o17.f | gb | AAQ83887.1 | 461 |
| ilh1c.pk006.c6.f | gb | EAA06671.2 | 201 |
| ilh1c.pk006.f2.f | emb | CAF96101.1 | 180 |
| ilh1c.pk007.a8.f | gb | EAL28755.1 | 343 |
| ilh1c.pk007.b21.f | ref | XP_422806.1 | 140 |
| ilh1c.pk007.g16.f | ref | YP_102734.1 | 129 |
| ilh1c.pk007.j24.f | gb | AAB72001.1 | 168 |
| ilh1c.pk007.o17.f | ref | NP_001015958.1 | 118 |
| ilh1c.pk007.o17.f | ref | NP_001030215.1 | 118 |
| ilh1c.pk007.p11.f | gb | ABA54998.1 | 231 |
| ilh1c.pk007.p13.f | dbj | BAA91976.1 | 337 |
| ilh1c.pk008.c24.f | ref | XP_624438.1 | 804 |
| ilh1c.pk008.fl6.f | sp | P04069 | 273 |
| ilh1c.pk008.h14.f | ref | XP_391971.1 | 401 |
| ilh1c.pk008.j3.f | ref | XP_397432.2 | 305 |
| ilh1c.pk008.k6.f | gb | AAH85379.1 | 222 |
| ilh1c.pk009.d7.f | ref | XP_392724.2 | 1062 |
| ilh1c.pk009.d7.f | ref | XP_623058.1 | 1062 |
| ilh1c.pk009.f20.f | ref | XP_394628.2 | 332 |
| ilh1c.pk010.f11.f | sp | Q7M4F2 | 359 |
| ilh1c.pk010.i24.f | ref | XP_397432.2 | 190 |
| ilh1c.pk010.m17.f | gb | EAA12371.3 | 392 |
| ilh1c.pk010.n4.f | ref | XP_624607.1 | 423 |
| ilh1c.pk011.a8.f | gb | AAP49008.1 | 433 |
| ilh1c.pk011.a8.f | gb | AAP49283.1 | 433 |
| ilh1c.pk011.d10.f | ref | XP_623853.1 | 358 |
| ilh1c.pk011.e16.f | ref | XP_393244.1 | 522 |
| ilh1c.pk009.d7.f | ref | XP_392724.2 | 1062 |
| ilh1c.pk009.d7.f | ref | XP_623058.1 | 1062 |
| ilh1c.pk003.d10.f | emb | CAF92618.1 | 196 |
| ilh1c.pk003.f22.f | emb | CAF92109.1 | 360 |
| ilh1c.pk004.e16.f | ref | XP_397356.2 | 317 |
| ilh1c.pk004.m22.f | ref | XP_541817.2 | 200 |
| ilh1c.pk004.m22.f | ref | XP_848286.1 | 200 |
| ilh1c.pk005.l24.f | gb | AAN71350.1 | 427 |
| ilh1c.pk005.l24.f | ref | NP_733291.1 | 427 |
| ilh1c.pk006.c15.f | gb | EAL38766.1 | 400 |
| ilh1c.pk001.f20.f | gb | AAB71256.1 | 392 |
| ilh1c.pk006.c6.f | gb | EAA06671.2 | 201 |
| ilh1c.pk001.h3.f | dbj | BAA86911.1 | 967 |
| ilh1c.pk007.c6.f | ref | XP_507719.1 | 126 |
| ilh1c.pk007.m5.f | ref | XP_342400.2 | 234 |
| ilh1c.pk008.c24.f | ref | XP_624438.1 | 804 |
| ilh1c.pk008.d5.f | ref | XP_422297.1 | 244 |
| ilh1c.pk008.f17.f | gb | AAT48984.1 | 386 |
| ilh1c.pk008.g3.f | emb | CAG00772.1 | 267 |
| ilh1c.pk008.g3.f | ref | XP_786904.1 | 267 |
| ilh1c.pk002.o12.f | gb | AAL93243.1 | 142 |
| ilh1c.pk003.d10.f | emb | CAF92618.1 | 196 |
| ilh1c.pk004.o2.f | gb | AAC41580.1 | 502 |
| ilh1c.pk004.o2.f | ref | XP_854245.1 | 502 |

TABLE 4

| est and position | Target Region of gene | Sense primer | Antisense primer | % CG | SEQ ID Target region/ sense/ antisense |
|---|---|---|---|---|---|
| ilh1c 43 .pk5. 26 o1.f 353 | AAGAGGTACAAATGTCTTTCCTG AAGTCAGTCCTACACGTGTCCTC AACAACGTTCGCCAGGATTTTTT | GAGGUACAAAUGUCUUUCC GUCAGUCCUACACGUGUCC CAACGUUCGCCAGGAUUUU | GGAAAGACAUUUGUACCUC GGACACGUGUAGGACUGAC AAAAUCCUGGCGAACGUUG | % CG = 39.1 % CG = 52.2 % CG = 39.1 | 22/23/24 25/26/27 28/29/30 |

TABLE 4-continued

| est and position | | | Target Region of gene | Sense primer | Antisense primer | % CG | SEQ ID Target region/ sense/ antisense |
|---|---|---|---|---|---|---|---|
| ilh1c | 16 | .pk4. | AAGACTGCTGACGGAATAACGAA | GACUGCUGACGGAAUAACG | CGUUAUUCCGUCAGCAGUC | % CG = 43.5 | 31/32/33 |
|  | 332 | e6.f | AACCCCGACGGCACCGTCGCTGA | CCCCGACGGCACCGUCGCU | AGCGACGGUGCCGUCGGGG | % CG = 69.6 | 34/35/36 |
|  | 56 |  | AAGATCTCCAAAGCTCGTGGAAT | GAUCUCCAAAGCUCGUGGA | UCCACGAGCUUUGGAGAUC | % CG = 43.5 | 37/38/39 |
| ilh1c | 49 | .pk1. | AAATTACCCGCGGAGGATACTCA | AUUACCCGCGGAGGAUACU | AGUAUCCUCCGCGGGUAAU | % CG = 47.8 | 40/41/42 |
|  | 256 | e23.f | AATTGTGGCTTCAGCTCCCGTAT | UUGUGGCUUCAGCUCCCGU | ACGGGAGCUGAAGCCACAA | % CG = 47.8 | 43/44/45 |
|  | 656 |  | AACTCTCTTGTANCCTCACCACA | CUCUCUUGUANCCUCACCA | UGGUGAGG.UACAAGAGAG | % CG = 43.5 | 46/47/48 |
| ilh1c | 37 | .pk1. | AAGTCTTTAAGGACGGATTTACG | GUCUUUAAGGACGGAUUUA | UAAAUCCGUCCUUAAAGAC | % CG = 39.1 | 49/50/51 |
|  | 24 | f11.f | AATGCGTGTTGGCTCATCTGTCA | UGCGUGUUGGCUCAUCUGU | ACAGAUGAGCCAACACGCA | % CG = 47.8 | 52/53/54 |
|  | 543 |  | AAGCTGGTGGTCGTCTGAAGGAT | GCUGGUGGUCGUCUGAAGG | CCUUCAGACGACCACCAGC | % CG = 52.2 | 55/56/57 |
|  | 613 |  | AACACTCGGATGAAATCACTGTG | CACUCGGAUGAAAUCACUG | CAGUGAUUUCAUCCGAGUG | % CG = 43.5 | 58/59/60 |
| ilh1c | 28 | .pk11. | AATCAGTATCACGCTCAGGATGT | UCAGUAUCACGCUCAGGAU | AUCCUGAGCGUGAUACUGA | % CG = 43.5 | 61/62/63 |
|  | 355 | m15.f | AACACCCATGAAGTCGCTGTCGC | CACCCAUGAAGUCGCUGUC | GACAGCGACUUCAUGGGUG | % CG = 56.5 | 64/65/66 |
|  | 57 |  | AAGATCTCCAAAGCTCGTGGAAT | GAUCUCCAAAGCUCGUGGA | UCCACGAGCUUUGGAGAUC | % CG = 43.5 | 67/68/69 |
| ilh1c | 94 | .pk5. | AACTACAAGTATCCTGTGGAGGG | CUACAAGUAUCCUGUGGAG | CUCCACAGGAUACUUGUAG | % CG = 47.8 | 70/71/72 |
|  | 219 | d21.f | AAATTGGAGTGTGACTGGTGCTG | AUUGGAGUGUGACUGGUGC | GCACCAGUCACACUCCAAU | % CG = 47.8 | 73/74/75 |
|  | 57 |  | AACATCAGACGCCCTCTACTGGA | CAUCAGACGCCCUCUACUG | CAGUAGAGGGCGUCUGAUG | % CG = 52.2 | 76/77/78 |
| ilh1c | 51 | .pk11. | AAACGGTTCTTTCCGAAACGACG | ACGGUUCUUUCCGAAACGA | UCGUUUCGGAAAGAACCGU | % CG = 47.8 | 79/80/81 |
|  | 225 | f4.f | AACCATCGTTCCTGGTGATGCAT | CCAUCGUUCCUGGUGAUGC | GCAUCACCAGGAACGAUGG | % CG = 47.8 | 82/83/84 |
|  | 545 |  | AAAGTCTTCAGAGAGGAAGCTGC | AGUCUUCAGAGAGGAAGCU | AGCUUCCUCUCUGAAGACU | % CG = 47.8 | 85/86/87 |
| ilh1c | 79 | .pk4. | AAGATGTTCCATGGAGAGGCACA | GAUGUUCCAUGGAGAGGCA | UGCCUCUCCAUGGAACAUC | % CG = 47.8 | 88/89/90 |
|  | 22 | l22.f | AAATAGGGCAACTTCACGGATTA | AUAGGGCAACUUCACGGAU | AUCCGUGAAGUUGCCCUAU | % CG = 39.1 | 91/92/93 |
|  | 469 |  | AAGAACCATTCGCCGTTATCACC | GAACCAUUCGCCGUUAUCA | UGAUAACGGCGAAUGGUUC | % CG = 47.8 | 94/95/96 |
|  | 651 |  | AAGCTGCACTGGGATTCATTCCT | GCUGCACUGGGAUUCAUUC | GAAUGAAUCCCAGUGCAGC | % CG = 47.8 | 97/98/99 |
| ilh1c | 88 | .pk3. | AATACAAAAGTCGCGTCTTCCGG | UACAAAAGUCGCGUCUUCC | GGAAGACGCGACUUUUGUA | % CG = 47.8 | 100/101/102 |
|  | 132 | d1.f | AAGATCTTTCGACTCTTGACGTG | GAUCUUUCGACUCUUGACG | CGUCAAGAGUCGAAAGAUC | % CG = 43.5 | 103/104/105 |
|  | 27 |  | AATATCGGTACTATTGGTCACGT | UAUCGGUACUAUUGGUCAC | GUGACCAAUAGUACCGAUA | % CG = 39.1 | 106/107/108 |
| ilh1c | 96 | .pk1. | AATTTCGACGTGGAAGTGTTAAG | UUUCGACGUGGAAGUGUUA | UAACACUUCCACGUCGAAA | % CG = 39.1 | 109/110/111 |
|  | 249 | d2.f | AATGTTGCATCTCGAAGGTGCAA | UGUUGCAUCUCGAAGGUGC | GCACCUUCGAGAUGCAACA | % CG = 43.5 | 112/113/114 |
|  | 422 |  | AACACTGGGTAAAGATGTAGGAC | CACUGGGUAAAGAUGUAGG | CCUACAUCUUUACCCAGUG | % CG = 43.5 | 115/116/117 |
| ilh1c | 29 | .pk11. | AACCCGGGTCTTTTCTGTAAAGA | CCCGGGUCUUUUCUGUAAA | UUUACAGAAAAGACCCGGG | % CG = 43.5 | 118/119/120 |
|  | 22 | h12.f | AAACCTCGAAACCAAAAACGTAG | ACCUCGAAACCAAAAACGU | ACGUUUUUGGUUUCGAGGU | % CG = 39.1 | 121/122/123 |
|  | 665 |  | AAGTTGGAAACTGGAGTCCAGAT | GUUGGAAACUGGAGUCCAG | CUGGACUCCAGUUUCCAAC | % CG = 43.5 | 124/125/126 |
| ilh1c | 72 | .pk2. | AAATCTTCTTCGGGACTATCCAT | AUCUUCUUCGGGACUAUCC | GGAUAGUCCCGAAGAAGAU | % CG = 39.1 | 127/128/129 |
|  | 23 | a24.f | AAAACCAGAACAGAAACCGGAGT | AACCAGAACAGAAACCGGA | UCCGGUUUCUGUUCUGGUU | % CG = 43.5 | 130/131/132 |
|  | 645 |  | AAGTGATGACCTTCTCTTTGGGA | GUGAUGACCUUCUCUUUGG | CCAAAGAGAAGGUCAUCAC | % CG = 43.5 | 133/134/135 |
| ilh1c | 9 | .pk9. | AACAGGACATCATATTTCGCAGG | CAGGACAUCAUAUUUCGCA | UGCGAAAUAUGAUGUCCUG | % CG = 43.5 | 136/137/138 |
|  | 21 | f2.f | AAAAAGCACTAGATGAGCCGAAG | AAAGCACUAGAUGAGCCGA | UCGGCUCAUCUAGUGCUUU | % CG = 43.5 | 139/140/141 |
|  | 43 |  | AAGTTCATCGGAGAGCTTTGCAA | GUUCAUCGGAGAGCUUUGC | GCAAAGCUCUCCGAUGAAC | % CG = 43.5 | 142/143/144 |
|  | 596 |  | AACTTTTTGATCGTATGGCGTCC | CUUUUUGAUCGUAUGGCGU | ACGCCAUACGAUCAAAAAG | % CG = 43.5 | 145/146/147 |
| ilh1c | 3 | .pk2. | AACTTTCCTNTTCCGCGTTGTTG | CUUUCCUNUUCCGCGUUGU | ACAACGCGGAA.AGGAAAG | % CG = 43.5 | 148/149/150 |
|  | 394 | d9.f | AAGAGAACGGAGATAACGAGGNA | GAGAACGGAGAUAACGAGG | CCUCGUUAUCUCCGUUCUC | % CG = 43.5 | 151/152/153 |
|  | 55 |  | AAAAAGGCTCCGACTGTTTGGNA | AAAGGCUCCGACUGUUUGG | CCAAACAGUCGGAGCCUUU | % CG = 43.5 | 154/155/156 |

TABLE 4-continued

| est and position | Target Region of gene | Sense primer | Antisense primer | % CG | SEQ ID Target region/ sense/ antisense |
|---|---|---|---|---|---|
| ilh1c  4 .pk3.j7.f | AAAAAGCTCCATACAGGTGAACG | AAAGCUCCAUACAGGUGAA | UUCACCUGUAUGGAGCUUU | % CG = 43.5 | 157/158/159 |
| 26 | AAAAACAAGCACAAAGACGGGTC | AAACAAGCACAAAGACGGG | CCCGUCUUUGUGCUUGUUU | % CG = 43.5 | 160/161/162 |
| 669 | AAGTATTTCAGTCTTCCTCTGCT | GUAUUUCAGUCUUCCUCUG | CAGAGGAAGACUGAAAUAC | % CG = 39.1 | 163/164/165 |
| ilh1c  36 .pk3.o1.f | AAGTCAGAATGTCGACTGAAAAG | GUCAGAAUGUCGACUGAAA | UUUCAGUCGACAUUCUGAC | % CG = 39.1 | 166/167/168 |
| 267 | AAGGAACGTGAGATGATCCTGTA | GGAACGUGAGAUGAUCCUG | CAGGAUCAUCUCACGUUCC | % CG = 43.5 | 169/170/171 |
| 525 | AACCCNACTTTCTTGTACAAAGT | CCCNACUUUCUUGUACAAA | UUUGUACAAGAAAGU.GGG | % CG = 34.8 | 172/173/174 |
| ilh1c  11 .pk4.b8.f | AAGTTTTTGCGGTGTCGGAATGT | GUUUUUGCGGUGUCGGAAU | AUUCCGACACCGCAAAAAC | % CG = 43.5 | 175/176/177 |
| 361 | AAAANNNNTCCGAACGCCGCCAA | AANNNNUCCGAACGCCGCC | GGCGGCGUUCGGA....UU | % CG = 43.5 | 178/179/180 |
| 668 | AAACTCACCTTCTCTCAAGCCGT | ACUCACCUUCUCUCAAGCC | GGCUUGAGAGAAGGUGAGU | % CG = 47.8 | 181/182/183 |
| ilh1c  56 .pk4.d17.f | AATTCAACGAGATAACCGAATGA | UUCAACGAGAUAACCGAAU | AUUCGGUUAUCUCGUUGAA | % CG = 34.8 | 184/185/186 |
| 295 | AAGTCTGTGTTGTCTGAAAGTAG | GUCUGUGUUGUCUGAAAGU | ACUUUCAGACAACACAGAC | % CG = 39.1 | 187/188/189 |
| 56 | AACTCCCAGTGTCGTCCTCAAGA | CUCCCAGUGUCGUCCUCAA | UUGAGGACGACACUGGGAG | % CG = 52.2 | 190/191/192 |
| 649 | AAGTTCCATCCAAAGCACCGCAG | GUUCCAUCCAAAGCACCGC | GCGGUGCUUUGGAUGGAAC | % CG = 52.2 | 193/194/195 |
| ilh1c  8 .pk4.k13.f | AAGGAAGTATCGCACCACATTCT | GGAAGUAUCGCACCACAUU | AAUGUGGUGCGAUACUUCC | % CG = 43.5 | 196/197/198 |
| 445 | AAATCAAGGACAATGTGGTAGCT | AUCAAGGACAAUGUGGUAG | CUACCACAUUGUCCUUGAU | % CG = 39.1 | 199/200/201 |
| 698 | AAAGTGAAGGTGAAGATTGCGAG | AGUGAAGGUGAAGAUUGCG | CGCAAUCUUCACCUUCACU | % CG = 43.5 | 202/203/204 |
| ilh1c  14 .pk11.a8.f | AAGATGTTGTGTTAGGTTTACCG | GAUGUUGUGUUAGGUUUAC | GUAAACCUAACACAACAUC | % CG = 39.1 | 205/206/207 |
| 394 | AACAAAGTCGATTCCACCTAGAG | CAAAGUCGAUUCCACCUAG | CUAGGUGGAAUCGACUUUG | % CG = 43.5 | 208/209/210 |
| 515 | AACTTTGGTCCTGGTTTGGATAG | CUUUGGUCCUGGUUUGGAU | AUCCAAACCAGGACCAAAG | % CG = 43.5 | 211/212/213 |
| ilh1c  42 .pk11.d1.f | AAGCTACAGGAATCCGGANAATT | GCUACAGGAAUCCGGANAA | UU.UCCGGAUUCCUGUAGC | % CG = 39.1 | 214/215/216 |
| 136 | AAGGCGTGTAATCTCTCAAGCAA | GGCGUGUAAUCUCUCAAGC | GCUUGAGAGAUUACACGCC | % CG = 43.5 | 217/218/219 |
| 182 | AATTCGCGGTCAACTTTATCTCT | UUCGCGGUCAACUUUAUCU | AGAUAAAGUUGACCGCGAA | % CG = 39.1 | 220/221/222 |

(Note: the sense RNA primer sequence and the antisense RNA primer sequences shown in table 4 were generated to have 2 thymine residues at the 3' end.)

Example 2

*Lygus hesperus* Assay Methodology

*Lygus hesperus* egg packs are received from the University of Missouri and placed in Fluon® AD-1 (AG Fluoropolymers)—treated containers in a 18° C. incubator, RH~40 to 60%, and no light. Eggs generally hatch after 6 days and then are transferred to a 25° incubator, RH~40 to 60%, 22 hours Day: 2 hours Night. Neonates are fed artificial diet (Bio-Serv F9644B) in parafilm packets. 1 day old $2^{nd}$ instar nymphs are used for bioassay.

Liquid samples (20 ul) are dispensed to 96 well microtiter plates (Falcon Assay Plate 353910) and mixed with 75 ul of artificial diet (Bio-Serv F9644B). Assays typically include 4 to 5 observations for each sample. The plate is then covered with slightly stretched parafilm. Several (3 to 8) 1 day old $2^{nd}$ instar nymphs are placed in each well of a 96 well filter plate (Millipore MABVN1250). The diet/sample plate is flipped on top of the nymph-infested filter plate so that the wells line up and the nymphs can feed on the diet/sample mixture through the parafilm. The filter plate and the diet plate are clamped together using rubber bands. The plates are placed in a 25° incubator, RH~40 to 60%, and no light, and the assay is scored after 4 days. Each well is scored individually and given a rating of either 0, 1, or 2 based on the following system:

0=Normal development—molting to third instar nymphs
1=Stunted growth—same size as 1 day old $2^{nd}$ in stars or slightly larger
2=Dead The score is based on the least affected nymph in the well. For example, if all but one nymph is dead, and that nymph is stunted, the well would be scored as a 1. If 4 nymphs are stunted and 2 are normal, the well would be scored as 0, Several repetitions are run using the same sample and dose. The well values for all observations are added together and a % effect is calculated using the following formula:

$$\frac{Rep1(\text{well value}) + Rep2(\text{well value}) + Rep3(\text{well value}) \ldots + RepN(\text{well value})}{(\text{Total number of reps } N)*(2)} \times 100 = \% \text{ effect}$$

Where N is the number of observations run for that sample and dose

Using the % effect numbers and the corresponding doses, an Effective Concentration (EC) 50 can be calculated using a probit analysis program (LdP Line).

Results:

62 synthetic dsRNA samples (Sigm-Genosys, The Woodlands, Tex.) were tested at the following concentrations: 35, 17.5, 8.25, and 4.125 ppm. Of the samples tested, 47 were inactive, while 15 demonstrated varying degrees of activity including stunting and mortality (highlighted in table 5).

TABLE 5

| Sample id | Targeted region | sense strand | antisense strand | SEQ ID NO |
|---|---|---|---|---|
| A1 | ilh1c.pk005.o10.f | AAGAGGTACAAATGTCTTTCCTG | GAGGUACAAAUGUCUUUCC | GGAAAGACAUUUGUACCUC | 223/224/225 |
| B1 | ilh1c.pk005.o10.f | AAGTCAGTCCTACACGTGTCCTC | GUCAGUCCUACACGUGUCC | GGACACGUGUAGGACUGAC | 226/227/228 |
| C1 | ilh1c.pk005.o10.f | AACAACGTTCGCCAGGATTTTTT | CAACGUUCGCCAGGAUUUU | AAAAUCCUGGCGAACGUUG | 229/230/231 |
| D1 | ilh1c.pk004.e6.f | AAGACTGCTGACGGAATAACGAA | GACUGCUGACGGAAUAACG | CGUUAUUCCGUCAGCAGUC | 232/233/234 |
| E1 | ilh1c.pk004.e6.f | AACCCCGACGGCACCGTCGCTGA | CCCCGACGGCACCGUCGCU | AGCGACGGUGCCGUCGGGG | 235/236/237 |
| F1 | ilh1c.pk004.e6.f | AAGATCTCCAAAGCTCGTGGAAT | GAUCUCCAAAGCUCGUGGA | UCCACGAGCUUUGGAGAUC | 238/239/240 |
| G1 | ilh1c.pk001.e23.f | AAATTACCCGCGGAGGATACTCA | AUUACCCGCGGAGGAUACU | AGUAUCCUCCGCGGGUAAU | 241/242/243 |
| H1 | ilh1c.pk001.e23.f | AATTGTGGCTTCAGCTCCCGTAT | UUGUGGCUUCAGCUCCCGU | ACGGGAGCUGAAGCCACAA | 244/245/246 |
| A2 | ilh1c.pk010.f11.f | AAGTCTTTAAGGACGGATTTACG | GUCUUUAAGGACGGAUUUA | UAAAUCCGUCCUUAAAGAC | 247/248/249 |
| B2 | ilh1c.pk010.f11.f | AATGCGTGTTGGCTCATCTGTCA | UGCGUGUUGGCUCAUCUGU | ACAGAUGAGCCAACACGCA | 250/251/252 |
| C2 | ilh1c.pk010.f11.f | AAGCTGGTGGTCGTCTGAAGGAT | GCUGGUGGUCGUCUGAAGG | CCUUCAGACGACCACCAGC | 253/254/255 |
| D2 | ilh1c.pk010.f11.f | AACACTCGGATGAAATCACTGTG | CACUCGGAUGAAAUCACUG | CAGUGAUUUCAUCCGAGUG | 256/257/258 |
| E2 | ilh1c.pk011.m15.f | AATCAGTATCACGCTCAGGATGT | UCAGUAUCACGCUCAGGAU | AUCCUGAGCGUGAUACUGA | 259/260/261 |
| F2 | ilh1c.pk011.m15.f | AACACCCATGAAGTCGCTGTCGC | CACCCAUGAAGUCGCUGUC | GACAGCGACUUCAUGGGUG | 262/263/264 |
| G2 | ilh1c.pk011.m15.f | AAGATCTCCAAAGCTCGTGGAAT | GAUCUCCAAAGCUCGUGGA | UCCACGAGCUUUGGAGAUC | 265/266/267 |
| H2 | ilh1c.pk005.d21.f | AACTACAAGTATCCTGTGGAGGG | CUACAAGUAUCCUGUGGAG | CUCCACAGGAUACUUGUAG | 268/269/270 |
| A3 | ilh1c.pk005.d21.f | AAATTGGAGTGTGACTGGTGCTG | AUUGGAGUGUGACUGGUGC | GCACCAGUCACACUCCAAU | 271/272/273 |
| B3 | ilh1c.pk005.d21.f | AACATCAGACGCCCTCTACTGGA | CAUCAGACGCCCUCUACUG | CAGUAGAGGGCGUCUGAUG | 274/275/276 |
| C3 | ilb1c.pk011.f4.f | AAACGGTTCTTTCCGAAACGACG | ACGGUUCUUUCCGAAACGA | UCGUUUCGGAAAGAACCGU | 277/278/279 |
| D3 | ilh1c.pk011.f4.f | AACCATCGTTCCTGGTGATGCAT | CCAUCGUUCCUGGUGAUGC | GCAUCACCAGGAACGAUGG | 280/281/282 |
| E3 | ilh1c.pk011.f4.f | AAAGTCTTCAGAGAGGAAGCTGC | AGUCUUCAGAGAGGAAGCU | AGCUUCCUCUCUGAAGACU | 283/284/285 |
| F3 | ilh1c.pk004.122.f | AAGATGTTCCATGGAGAGGCACA | GAUGUUCCAUGGAGAGGCA | UGCCUCUCCAUGGAACAUC | 286/287/288 |
| G3 | ilh1c.pk004.122.f | AAATAGGGCAACTTCACGGATTA | AUAGGGCAACUUCACGGAU | AUCCGUGAAGUUGCCCUAUd | 289/290/291 |
| H3 | ilh1c.pk004.122.f | AAGAACCATTCGCCGTTATCACC | GAACCAUUCGCCGUUAUCA | UGAUAACGGCGAAUGGUUC | 292/293/294 |
| A4 | ilh1c.pk004.122.f | AAGCTGCACTGGGATTCATTCCT | GCUGCACUGGGAUUCAUUC | GAAUGAAUCCCAGUGCAGC | 295/296/297 |
| B4 | ilh1c.pk003.d10.f | AATACAAAAGTCGCGTCTTCCGG | UACAAAAGUCGCGUCUUCC | GGAAGACGCGACUUUUGUA | 298/299/300 |
| C4 | ilh1c.pk003.d10.f | AAGATCTTTCGACTCTTGACGTG | GAUCUUUCGACUCUUGACG | CGUCAAGAGUCGAAAGAUC | 301/302/303 |
| D4 | ilh1c.pk003.d10.f | AATATCGGTACTATTGGTCACGT | UAUCGGUACUAUUGGUCAC | GUGACCAAUAGUACCGAUA | 304/305/306 |
| E4 | ilh1c.pk010.d2.f | AATTTCGACGTGGAAGTGTTAAG | UUUCGACGUGGAAGUGUUA | UAACACUUCCACGUCGAAA | 307/308/309 |
| F4 | ilh1c.pk010.d2.f | AATGTTGCATCTCGAAGGTGCAA | UGUUGCAUCUCGAAGGUGC | GCACCUUCGAGAUGCAACA | 310/311/312 |
| G4 | ilh1c.pk010.d2.f | AACACTGGGTAAAGATGTAGGAC | CACUGGGUAAAGAUGUAGG | CCUACAUCUUUACCCAGUG | 313/314/315 |

TABLE 5-continued

| Sample id | Targeted region | sense strand | antisense strand | SEQ ID NO |
|---|---|---|---|---|
| H4 | ilh1c.pk011.h12.f | AACCCGGGTCTTTTCTGTAAAGA | CCCGGGUCUUUUCUGUAAA | UUUACAGAAAAGACCCGGG | 316/317/318 |
| A5 | ilh1c.pk011.h12.f | AAACCTCGAAACCAAAAACGTAG | ACCUCGAAACCAAAAACGU | ACGUUUUGGUUUCGAGGU | 319/320/321 |
| B5 | ilh1c.pk011.b12.f | AAGTTGGAAACTGGAGTCCAGAT | GUUGGAAACUGGAGUCCAG | CUGGACUCCAGUUUCCAAC | 322/323/324 |
| C5 | ilh1c.pk002.a24.f | AAATCTTCTTCGGGACTATCCAT | AUCUUCUUCGGGACUAUCC | GGAUAGUCCCGAAGAAGAU | 325/326/327 |
| D5 | ilh1c.pk002.a24.f | AAAACCAGAACAGAAACCGGAGT | AACCAGAACAGAAACCGGA | UCCGGUUUCUGUUCUGGUU | 328/329/330 |
| E5 | ilh1c.pk002.a24.f | AAGTGATGACCTTCTCTTTGGGA | GUGAUGACCUUCUCUUUGG | CCAAAGAGAAGGUCAUCAC | 331/332/333 |
| F5 | ilh1c.pk009.f20.f | AACAGGACATCATATTTCGCAGG | CAGGACAUCAUAUUUCGCA | UGCGAAAUAUGAUGUCCUG | 334/335/336 |
| G5 | ilh1c.pk009.f20.f | AAAAAGCACTAGATGAGCCGAAG | AAAGCACUAGAUGAGCCGA | UCGGCUCAUCUAGUGCUUU | 337/338/339 |
| H5 | ilh1c.pk009.f20.f | AAGTTCATCGGAGAGCTTTGCAA | GUUCAUCGGAGAGCUUUGC | GCAAAGCUCUCCGAUGAAC | 340/341/342 |
| A6 | ilh1c.pk009.f20.f | AACTTTTTGATCGTATGGCGTCC | CUUUUUGAUCGUAUGGCGU | ACGCCAUACGAUCAAAAAG | 343/344/345 |
| B6 | ilh1c.pk002.d9.f | AAGAGAACGGAGATAACGAGGNA | GAGAACGGAGAUAACGAGG | CCUCGUUAUCUCCGUUCUC | 346/347/348 |
| C6 | ilh1c.pk002.d9.f | AAAAAGGCTCCGACTGTTTGGNA | AAAGGCUCCGACUGUUUGG | CCAAACAGUCGGAGCCUUU | 349/350/351 |
| D6 | ilh1c.pk003.j7.f | AAAAAGCTCCATACAGGTGAACG | AAAGCUCCAUACAGGUGAA | UUCACCUGUAUGGAGCUUU | 352/353/354 |
| E6 | ilh1c.pk003.j7.f | AAAAACAAGCACAAAGACGGGTC | AAACAAGCACAAAGACGGG | CCCGUCUUUGUGCUUGUUU | 355/356/357 |
| F6 | ilh1c.pk003.j7.f | AAGTATTTCAGTCTTCCTCTGCT | GUAUUUCAGUCUUCCUCUG | CAGAGGAAGACUGAAAUAC | 358/359/360 |
| G6 | ilh1c.pk003.o10.f | AAGTCAGAATGTCGACTGAAAAG | GUCAGAAUGUCGACUGAAA | UUUCAGUCGACAUUCUGAC | 361/362/363 |
| H6 | ilh1c.pk003.o10.f | AAGGAACGTGAGATGATCCTGTA | GGAACGUGAGAUGAUCCUG | CAGGAUCAUCUCACGUUCC | 364/365/366 |
| A7 | ilh1c.pk004.b8.f | AAGTTTTTGCGGTGTCGGAATGT | GUUUUUGCGGUGUCGGAAU | AUUCCGACACCGCAAAAACd | 367/368/369 |
| B7 | ilh1c.pk004.b8.f | AAACTCACCTTCTCTCAAGCCGT | ACUCACCUUCUCUCAAGCC | GGCUUGAGAGAAGGUGAGU | 370/371/372 |
| C7 | ilh1c.pk004.d17.f | AATTCAACGAGATAACCGAATGA | UUCAACGAGAUAACCGAAU | AUUCGGUUAUCUCGUUGAA | 373/374/375 |
| D7 | ilh1c.pk004.d17.f | AAGTCTGTGTTGTCTGAAAGTAG | GUCUGUGUUGUCUGAAAGU | ACUUUCAGACAACACAGAC | 376/377/378 |
| E7 | ilh1c.pk004.d17.f | AACTCCCAGTGTCGTCCTCAAGA | CUCCCAGUGUCGUCCUCAA | UUGAGGACGACACUGGGAG | 379/380/381 |
| F7 | ilh1c.pk004.d17.f | AAGTTCCATCCAAAGCACCGCAG | GUUCCAUCCAAAGCACCGC | GCGGUGCUUUGGAUGGAAC | 382/383/384 |
| G7 | ilh1c.pk004.k13.f | AAGGAAGTATCGCACCACATTCT | GGAAGUAUCGCACCACAUU | AAUGUGGUGCGAUACUUCC | 385/386/387 |
| H7 | ilh1c.pk004.k13.f | AAATCAAGGACAATGTGGTAGCT | AUCAAGGACAAUGUGGUAG | CUACCACAUUGUCCUUGAU | 388/389/390 |
| A8 | ilh1c.pk004.k13.f | AAAGTGAAGGTGAAGATTGCGAG | AGUGAAGGUGAAGAUUGCG | CGCAAUCUUCACCUUGACU | 391/392/393 |
| B8 | ilh1c.pk011.a8.f | AAGATGTTGTGTTAGGTTTACCG | GAUGUUGUGUUAGGUUUAC | GUAAACCUAACACAACAUC | 394/395/396 |
| C8 | ilh1c.pk011.a8.f | AACAAAGTCGATTCCACCTAGAG | CAAAGUCGAUUCCACCUAG | CUAGGUGGAAUCGACUUUG | 397/398/399 |
| D8 | ilh1c.pk011.a8.f | AACTTTGGTCCTGGTTTGGATAG | CUUUGGUCCUGGUUUGGAU | AUCCAAACCAGGACCAAAG | 400/401/402 |
| E8 | ilh1c.pk011.d10.f | AAGGCGTGTAATCTCTCAAGCAA | GGCGUGUAAUCUCUCAAGC | GCUUGAGAGAUUACACGCC | 403/404/405 |
| F8 | ilh1c.pk011.d10.f | AATTCGCGGTCAACTTTATCTCT | UUCGCGGUCAACUUUAUCU | AGAUAAAGUUGACCGCGAA | 406/407/408 |

(Note:
the sense RNA primer sequence and the antisense RNA primer sequences shown in table 5 were generated to have 2 thymine residues at the 3' end.)

TABLE 6

| | % Response (4 reps) | | | |
|---|---|---|---|---|
| Sample | 35 ppm | 17.5 ppm | 8.25 ppm | 4.125 ppm |
| A1 | 37.5 | 0 | 0 | 25 |
| B1 | 25 | 0 | 0 | 0 |
| C1 | 0 | 0 | 0 | 0 |
| D1 | 12.5 | 0 | 0 | 0 |
| E1 | 0 | 0 | 0 | 0 |
| F1 | 12.5 | 0 | 25 | 0 |
| G1 | 0 | 0 | 0 | 0 |
| H1 | 0 | 0 | 0 | 0 |
| A2 | 12.5 | 0 | 0 | 25 |
| B2 | 25 | 0 | 0 | 0 |

TABLE 6-continued

| Sample | % Response (4 reps) | | | |
|---|---|---|---|---|
| | 35 ppm | 17.5 ppm | 8.25 ppm | 4.125 ppm |
| C2 | 0 | 0 | 0 | 0 |
| D2 | 0 | 25 | 25 | 0 |
| E2 | 0 | 0 | 25 | 0 |
| F2 | 0 | 0 | 0 | 0 |
| G2 | 0 | 0 | 0 | 0 |
| H2 | 0 | 0 | 0 | 25 |
| A3 | 0 | 0 | 0 | 0 |
| B3 | 0 | 0 | 0 | 0 |
| C3 | 12.5 | 0 | 0 | 0 |
| D3 | 0 | 0 | 25 | 25 |
| E3 | 75 | 62.5 | 12.5 | 0 |
| F3 | 0 | 0 | 0 | 0 |
| G3 | 87.5 | 25 | 0 | 0 |
| H3 | 100 | 50 | 12.5 | 0 |
| A4 | 25 | 12.5 | 0 | 0 |
| B4 | 12.5 | 0 | 0 | 0 |
| C4 | 12.5 | 0 | 0 | 0 |
| D4 | 62.5 | 0 | 0 | 0 |
| E4 | 37.5 | 25 | 0 | 0 |
| F4 | 0 | 25 | 0 | 0 |
| G4 | 25 | 0 | 0 | 0 |
| H4 | 100 | 37.5 | 0 | 0 |
| A5 | 62.5 | 37.5 | 0 | 0 |
| B5 | 100 | 75 | 12.5 | 0 |
| C5 | 100 | 100 | 50 | 37.5 |
| D5 | 100 | 100 | 37.5 | 12.5 |
| E5 | 100 | 87.5 | 50 | 12.5 |
| F5 | 100 | 50 | 0 | 0 |
| G5 | 100 | 100 | 50 | 0 |
| H5 | 87.5 | 50 | 0 | 25 |
| A6 | 100 | 50 | 25 | 0 |
| B6 | 100 | 37.5 | 0 | 0 |
| C6 | 0 | 0 | 0 | 0 |
| D6 | 0 | 0 | 0 | 0 |
| E6 | 0 | 12.5 | 0 | 0 |
| F6 | 0 | 0 | 0 | 0 |
| G6 | 0 | 0 | 25 | 25 |
| H6 | 0 | 0 | 0 | 0 |
| A7 | 0 | 0 | 0 | 0 |
| B7 | 0 | 0 | 0 | 0 |
| C7 | 0 | 0 | 0 | 25 |
| D7 | 0 | 0 | 0 | 0 |
| E7 | 0 | 0 | 0 | 0 |
| F7 | 0 | 0 | 0 | 0 |
| G7 | 0 | 0 | 0 | 0 |
| H7 | 0 | 0 | 0 | 0 |
| A8 | 0 | 0 | 0 | 0 |
| B8 | 0 | 0 | 0 | 0 |
| C8 | 12.5 | 0 | 0 | 0 |
| D8 | 0 | 0 | 25 | 0 |
| E8 | 0 | 0 | 0 | 0 |
| F8 | 0 | 0 | 0 | 0 |

A confirmation test was run with the 14 most active samples. The activity was confirmed. See, Table 7.

TABLE 7

| | % Activity (5 reps) | | | |
|---|---|---|---|---|
| | 37.5 ppm | 17.5 ppm | 8.25 ppm | 4.125 ppm |
| 3E | 100 | 50 | 30 | 0 |
| 3G | 90 | 40 | 10 | 0 |
| 3H | 90 | 60 | 10 | 0 |
| 4H | 100 | 40 | 10 | 0 |
| 5A | 90 | 40 | 10 | 0 |
| 5B | 100 | 80 | 50 | 0 |
| 5C | 100 | 90 | 50 | 20 |
| 5D | 100 | 90 | 40 | 10 |
| 5E | 100 | 80 | 40 | 0 |
| 5F | 90 | 40 | 0 | 0 |
| 5G | 100 | 70 | 40 | 10 |

TABLE 7-continued

| | % Activity (5 reps) | | | |
|---|---|---|---|---|
| | 37.5 ppm | 17.5 ppm | 8.25 ppm | 4.125 ppm |
| 5H | 90 | 40 | 10 | 0 |
| 6A | 100 | 40 | 0 | 0 |
| 6B | 90 | 40 | 10 | 0 |

New samples were made of 7 of the most active samples. These were de-salted or were HPLC purified dsRNAs from the same vender (Sigma-Genosys, the Woodlands, Tex.). The samples tested were 5C, 5D, 5E, 5F, 5G, 5H, and 6A. Only one of the samples, 5C, showed activity at the doses tested, and only minor stunting was evident. See, Table 8. Similarly, the desalted primers also had limited activity.

TABLE 8

| | % Effect | |
|---|---|---|
| | HPLC | De-Salted |
| 35 ppm | 50 | 30 |
| 17.5 | 20 | 0 |
| 8.75 | 0 | 10 |
| 4.375 | 0 | 0 |

No Mortality, only minor stunting at 35 ppm

The samples were retested at a higher dose (70 ppm) and again, sample 5C was found to be the only sample active. See, Table 9. Mortality occurred with the two top doses (35 and 70 ppm).

TABLE 9

| | 5C % effect | |
|---|---|---|
| | HPLC purified | De-Salted |
| 70 ppm | 100 | 70 |
| 35 ppm | 70 | 30 |
| 17.5 ppm | 10 | 0 |
| 8.75 ppm | 0 | 0 |

Dosages were increased again for the HPLC-purified samples and activity became evident with all the samples tested. Mortality and stunting occurred at the top three doses. See, Table 10.

TABLE 10

| ppm | % Effected | | | | | | |
|---|---|---|---|---|---|---|---|
| | 5C | 5D | 5E | 5F | 5G | 5H | 6A |
| 100 | 100 | 75 | 75 | 75 | 100 | 87.5 | 37.5 |
| 50 | 50 | 62.5 | 37.5 | 25 | 50 | 25 | 25 |
| 25 | 12.5 | 12.5 | 12.5 | 12.5 | 12.5 | 12.5 | 12.5 |
| 12.5 | 0 | 0 | 12.5 | 0 | 0 | 0 | 0 |

Example 3

Transformation of Maize

Immature maize embryos from greenhouse donor plants are bombarded with a plasmid containing the a silencing element of the invention is operably linked to a maize Ubi1-5UTR-Ubi1 intron and the selectable marker gene PAT (Wohlleben et al. (1988) *Gene* 70:25-37), which confers resistance to the herbicide Bialaphos. In one embodiment, the construct comprises two identical 2 to 300 bp segments of a target gene in opposite orientations with an intron segment between them acting as a hairpin loop. In further embodiments, the construct is driven off of the dMMV promoter. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the silencing element of interest operably linked to a maize Ubi1-5UTR-Ubi1 intron is made. This plasmid DNA plus plasmid DNA containing a PAT selectable marker is precipitated onto 1.1 µm (average diameter) tungsten pellets using a $CaCl_2$ precipitation procedure as follows: 100 µl prepared tungsten particles in water; 10 µl (1 µg) DNA in Tris EDTA buffer (1 µg total DNA); 100 µl 2.5 M $CaCl_2$; and, 10 µl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

The sample plates are bombarded at level #4 in a particle gun. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for the appropriate marker.

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

To assay for insecticidal activity, a FAW feeding assay can be performed. Briefly, leaf discs from the transgenic plant are excised using a 1 cm cork borer or leaf punch. Six leaf discs are prepared for each plant. The leaves are placed in a 24 well microtiter plate on top of 500 ul of 0.8% agar. Each leaf disc is infested with 2 neonate Fall armyworm and the plate is then sealed with mylar. A small ventilation hole is made for each well and the plates are then stored in a 28 C growth chamber. The assay is scored for mortality, stunting, and leaf consumption at 96 hours.

Example 4

*Agrobacterium*-Mediated Transformation of Maize

For *Agrobacterium*-mediated transformation of maize with a silencing element of the invention, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the polynucleotide comprising the silencing element to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 5

Soybean Embryo Transformation

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the following examples by the method of particle gun bombardment (Klein et al. (1987) *Nature*, 327:70).
Soybean Embryogenic Suspension Culture Initiation Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed are cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.
Preparation of DNA for Bombardment Either an intact plasmid or a DNA plasmid fragment containing the silencing element, such as those described in Example 3, and the selectable marker gene are used for bombardment. Plasmid DNA for bombardment are routinely prepared and purified using the method described in the Promega Protocols and Applications Guide, Second Edition (page 106). Fragments of the plasmids carrying the silencing element of interest are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing silencing element of interest are cut from the agarose gel. DNA is purified from the agarose using the GELase digesting enzyme following the manufacturer's protocol.

A 50 µl aliquot of sterile distilled water containing 3 mg of gold particles (3 mg gold) is added to 5 µl of a 1 µg/µl DNA solution (either intact plasmid or DNA fragment prepared as described above), 50 µl 2.5M $CaCl_2$ and 20 µl of 0.1 M spermidine. The mixture is shaken 3 min on level 3 of a vortex shaker and spun for 10 sec in a bench microfuge. After a wash with 400 µl 100% ethanol the pellet is suspended by sonication in 40 µl of 100% ethanol. Five µl of DNA suspension is dispensed to each flying disk of the Biolistic PDS1000/HE instrument disk. Each 5 µl aliquot contains approximately 0.375 mg gold per bombardment (i.e. per disk).
Tissue Preparation and Bombardment with DNA Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.
Selection of Transformed Embryos Transformed embryos were selected either using hygromycin (when the hygromycin phosphotransferase, HPT, gene was used as the selectable marker) or chlorsulfuron (when the acetolactate synthase, ALS, gene was used as the selectable marker).
Hygromycin (HPT) Selection Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.
Chlorsulfuron (ALS) Selection Following bombardment, the tissue is divided between 2 flasks with fresh SB 196 media and cultured as described above. Six to seven days post-bombardment, the SB196 is exchanged with fresh SB 196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB 196 to generate new, clonally propagated, transformed embryogenic suspension cultures.
Regeneration of Soybean Somatic Embryos into Plants In order to obtain whole plants from embryogenic suspension cultures, the tissue must be regenerated.
Embryo Maturation Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for the appropriate marker or the ability of the plant, when ingested by *Lygus*, to control the *Lygus*.
Embryo Desiccation and Germination Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for proteins

| Media Recipes SB 196 - FN Lite liquid proliferation medium (per liter) - | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2SO4 | 0.463 gm |
| Asparagine | 1.0 gm |
| Sucrose (1%) | 10 gm |
| pH 5.8 | |

| FN Lite Stock Solutions | | | |
|---|---|---|---|
| Stock# | | 1000 ml | 500 ml |
| 1 | MS Fe EDTA 100x Stock | | |
| | Na$_2$EDTA* | 3.724 g | 1.862 g |
| | FeSO$_4$—7H$_2$O | 2.784 g | 1.392 g |
| 2 | MS Sulfate 100x stock | | |
| | MgSO$_4$—7H$_2$O | 37.0 g | 18.5 g |
| | MnSO$_4$—H$_2$O | 1.69 g | 0.845 g |
| | ZnSO$_4$—7H$_2$O | 0.86 g | 0.43 g |
| | CuSO$_4$—5H$_2$O | 0.0025 g | 0.00125 g |
| 3 | FN Lite Halides 100x Stock | | |
| | CaCl$_2$—2H$_2$O | 30.0 g | 15.0 g |
| | KI | 0.083 g | 0.0715 g |
| | CoCl$_2$—6H$_2$O | 0.0025 g | 0.00125 g |
| 4 | FN Lite P, B, Mo 100x Stock | | |
| | KH$_2$PO$_4$ | 18.5 g | 9.25 g |
| | H$_3$BO$_3$ | 0.62 g | 0.31 g |
| | Na$_2$MoO$_4$—2H$_2$O | 0.025 g | 0.0125 g |

*Add first, dissolve in dark bottle while stirring

SB1 solid medium (per liter) comprises: 1 pkg. MS salts (Gibco/BRL—Cat#11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat#11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL—Cat#11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/ sucrose (Gibco/BRL—Cat#21153-036); pH 5.7; and, 5 g TC agar.

2,4-D stock is obtained premade from Phytotech cat#D 295—concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A plant cell having stably incorporated into its genome a heterologous polynucleotide comprising a silencing element, wherein said silencing element when ingested by a pest from the *Lygus* genus, reduces expression level of a target sequence in said pest, and thereby controls the pest from the *Lygus* family, and said silencing element is selected from the group consisting of:

a) a polynucleotide comprising the sense and antisense sequence of the sequence set forth in SEQ ID NO:325;

b) a polynucleotide comprising the sense and antisense sequence of a sequence having at least 95% sequence identity to the sequence set forth in SEQ ID NO: 325;

c) a polynucleotide comprising the sequence set forth in SEQ ID NO: 326 and 327; and d) a polynucleotide comprising a nucleotide sequence having at least 95% sequence identity to SEQ ID NO: 326 and 327.

2. The plant cell of claim 1, wherein said pest comprises *Lygus hesperus*.

3. The plant cell of claim 1, wherein said silencing element comprises a hairpin RNA.

4. The plant cell of claim 1, wherein said silencing element is operably linked to a heterologous promoter.

5. The plant cell of claim 1, wherein said plant cell is from a monocot.

6. The plant cell of claim 5, wherein said monocot is maize, barley, millet, wheat or rice.

7. The plant cell of claim 1, wherein said plant cell is from a dicot.

8. The plant cell of claim 7, wherein said plant cell is soybean, canola, alfalfa, sunflower, safflower, tobacco, *Arabidopsis*, or cotton.

9. The plant cell of claim 1, wherein said plant cell has stably incorporated into its genome a second polynucleotide comprising a suppressor enhancer element comprising the target pest sequence or an active variant or fragment thereof, wherein the combined expression of the silencing element and the suppressor enhancer element increases the concentration of an inhibitory RNAi specific for the pest target sequence in said plant cell.

10. A plant or plant part comprising the plant cell of claim 1.

11. The plant or plant part of claim 10, wherein the combined expression of said silencing element and the suppressor enhancer element increases the concentration of an inhibitory RNA specific for the pest target sequence in the phloem of said plant or plant part.

12. A transgenic seed from the plant of claim 10.

13. A method for controlling *Lygus* comprising feeding to a *lygus* a composition comprising a silencing element, wherein said silencing element, when ingested by said *Lygus*, reduces expression level of a target *Lygus* sequence and thereby controls the *Lygus* and said silencing elements is selected from the group consisting of:
   a) a polynucleotide comprising the sense and antisense sequence of the sequence set forth in SEQ ID NO: 325;
   b) a polynucleotide comprising the sense and antisense sequence of a sequence having at least 95% sequence identity to the sequence set forth in SEQ ID NO: 325;
   c) a polynucleotide comprising the sequence set forth in SEQ ID NO: 326 and 327; and
   d) a polynucleotide comprising a nucleotide sequence having at least 95% sequence identity to SEQ ID NO: 326 and 327.

14. The method of claim 13, wherein said composition comprises a plant or plant part having stably incorporated into its genome a polynucleotide comprising said silencing element.

15. The method of claim 13, wherein said pest comprises *Lygus hesperus*.

16. The method of claim 13, wherein said silencing element comprises a hairpin RNA.

17. The method of claim 13, wherein said silencing element is operably linked to a heterologous promoter.

18. The method of claim 14, wherein said plant or plant part has stably incorporated into its genome a second polynucleotide comprising a suppressor enhancer element comprising the target pest sequence or an active variant or fragment thereof, wherein the combined expression of the silencing element and the suppressor enhancer element increases the concentration of an inhibitory RNAi specific for the pest target sequence in said plant.

19. The method claim 18, wherein the combined expression of said silencing element and the suppressor enhancer element increases the concentration of an inhibitory RNA specific for the pest target sequence in the phloem of said plant or plant part.

20. The method of claim 13, wherein said plant is a monocot.

21. The method of claim 20, wherein said monocot is maize, barley, millet, wheat or rice.

22. The method of claim 13, wherein said plant is a dicot.

23. The method of claim 22, wherein said plant is soybean, canola, alfalfa, sunflower, safflower, tobacco, *Arabidopsis*, or cotton.

* * * * *

SEQUENCE LISTING

```
<160> NUMBER OF SEQ ID NOS: 408

<210> SEQ ID NO 1
<211> LENGTH: 643
<212> TYPE: DNA
<213> ORGANISM: Lygus hesperus

<400> SEQUENCE: 1
gcgtcacttg cgactcgtgt ctgagcggca acttcaaggg aaagaggtac aaatgtcttt      60
cctgctacga ctacgatctg tgcaccaact gctacgagtg tggcctcatc acgggactcc     120
actcagcaga gcatcccatg cagtgcatca tcaccagaca tgacgtcgac ctgtacttcg     180
ggggagacat gaatggcgac ggaagtcagt cctacacgtg tcctcattgt ggtctaatgg     240
ggttcagttt gtcgctgttg atcgagcacg tgagcggtga gcatatcgcg ctgagcaacg     300
ctgaagtgat ttgccctgtt tgcgccgcca cgccagtcaa ccgaccgaac aacgttcgcc     360 aggattttt ggggcacctg acgctggagc atcgctaccc ctcgcgagag ctgaccgcct     420
tcttcgaaga gccctcgtcc cgacacatgc cgagtggcgt ccgccggatt ccaccgccac     480
cagggcgcag cgctgccggg cgtggacgcc gggtcgcacg ttcatttcgg ctcctcaggc     540
```

```
gctcttactg gactcacatc ctccagagaa agtccggatc ccatcgccga gttcttctct    600
cagctgtctg gagtcgctcg tcctcaaggt cctgggccga ttc                      643
```

<210> SEQ ID NO 2
<211> LENGTH: 575
<212> TYPE: DNA
<213> ORGANISM: Lygus hesperus
<220> FEATURE:
<221> NAME/KEY: misc_feature
<222> LOCATION: 81, 426
<223> OTHER INFORMATION: n = A,T,C or G

<400> SEQUENCE: 2

```
accccctgat cgccgggatc gttgccaatc agtatcacgc tcaggatgtg ctcggacagt     60
acacttacgg ctactccgga nccccatccg ctaaacaaga ggttaagact gctgacggaa    120
taacgagagg atcttactcg tacatcgatg gaaacgggtc tcgtacagag cgcttcttac    180
gttgctgacc ccgtcaacgg gttcagagtc cacgccacca acctgcccgt gggacctgac    240
gggtccgtcg ctgccgctcc cgtcgccagg ctcctcagcc ctttggccat cagccctgtg    300
atcaacctcc acggcgctgc tcccctcaac cccgacggca ccgtcgctga cacccatgaa    360
gtcgctgtcg ccaaggccgc tcacctcgct gccatcaacg aggctagggc tagaggcaag    420
aggtcngccc cgctcaaccc cgacggtacc gtcgctgaca cccccgaagt tgctgctgct    480
aagtgggctc atctcgctga gatctccaaa gctcgtggaa tccctctcgt atacgctccc    540
agatggtggg gacctggtgc tccattgaac gctga                               575
```

<210> SEQ ID NO 3
<211> LENGTH: 722
<212> TYPE: DNA
<213> ORGANISM: Lygus hesperus
<220> FEATURE:
<221> NAME/KEY: misc_feature
<222> LOCATION: 659, 686, 689, 695, 713, 720, 722
<223> OTHER INFORMATION: n = A,T,C or G

<400> SEQUENCE: 3

```
ctacgctggc ggcccctccg ccaaggaaga gatcaagacc gccgacggaa ttacccgcgg     60
aggatactca tacatcgacg ccaacggtat cgtccagagc gcctcttacg tgtcggatcc    120
cgtcaacgga ttccgagtag ccgccactaa cctccccgct ggacctgcag tcccagctgg    180
accttcagtg gttgctgctg ctccagctgt cgttgctgct cctgctccag ttttggctgc    240
tgcccctgct ccaattgtgg cttcagctcc cgtttgggct gctcaaccag ctgttgttgc    300
cgctccagct cctgtcgctg tcgccgaagg ccccgcagtg accgccacca acgtccagga    360
agttgctgcc gctgctgctg acgtccccgt tgctgctgat ctccccgaga tcatcgctgc    420
ccgctctctg cccaccgtgg ttgccaccag ggccgccatc gctcacccc ttgccgcaac     480 ctcctggtcc ggcatcgtcc accacctgaa gaagcgttcc cttgccgccg ctaccgtcgt    540
cactcccctt actagttacc ccggatctac cgctcccttg gttcacgctt ctcccgttat    600
tgcggctaca cctgttatct ccgctcactc gggtttgatc gccactgact ctcttgtanc    660
ctcaccacac ctcgttggtg cagtangtnc tgtcnagccc ctccacaccg cntcctcan    720 an                                                                    722
```

<210> SEQ ID NO 4
<211> LENGTH: 700
<212> TYPE: DNA
<213> ORGANISM: Lygus hesperus
<220> FEATURE:
<221> NAME/KEY: misc_feature
<222> LOCATION: 675, 700
<223> OTHER INFORMATION: n = A,T,C or G

<400> SEQUENCE: 4

```
cattcgggag acattgcaaa actggatgca tagggggaagt ctttaggacg gatttacggc    60
atacagtaca tgttactgta agacacggcg cgtgactgga cagcaagcag aatggaggag   120
ggacaagtgt accaatcatc cgaccaaacc aactacgttt acgatgaagt gtttcctgcg   180
ctacctgaat cagccaaccc ggcacctcac aacgacatca aatttgcaa caacaaaatg    240
cgtgttggct catctgtcat cactcaggtt ttccgagtgc cagcagacga gcgccgctac   300
gatcacaaca acagctttgg ggaaaaggaa tccgtgagga cctgctctgc catcatgaag   360
gaaactggag cagtcattga gatcgccacg agcaaggata tgtctctgac tttcttggtg   420
actggaaaga ccgactcagt gatggatgct cgaaggaaga tactgagcaa ttttcagacc   480
caagcttcat ccaagctctc tattccgaaa gagcatcaca ggtggatcct tggaaaagct   540
ggtggtcgtc tgaaggattt ggaaaaatca acagccacca aatctccgt ccctggcata    600
aatgaacact cggatgaaat cactgtgacg ggaactcgtg aagggatcga caaggccatc   660
catgaaatgc aagtnatttc ggacgaacaa tccaagaagn              700
```

<210> SEQ ID NO 5
<211> LENGTH: 576
<212> TYPE: DNA
<213> ORGANISM: Lygus hesperus
<220> FEATURE:
<221> NAME/KEY: misc_feature
<222> LOCATION: 82, 427
<223> OTHER INFORMATION: n = A,T,C or G

<400> SEQUENCE: 5

```
aaccccctga tcgccgggat cgttgccaat cagtatcacg ctcaggatgt gctcggacag    60
tacacttacg gctactccgg anccccatcc gctaaacaag aggttaagac tgctgacgga   120
ataacgagag gatcttactc gtacatcgat ggaaacgggt ctcgtacaga gcgcttctta   180
cgttgctgac cccgtcaacg ggttcagagt ccacgccacc aacctgcccg tgggacctga   240
cgggtccgtc gctgccgctc ccgtcgccag gctcctcagc cctttggcca tcagccctgt   300
gatcaacctc cacggcgctg ctcccctcaa ccccgacggc accgtcgctg acacccatga   360
agtcgctgtc gccaaggccg ctcacctcgc tgccatcaac gaggctaggg ctagaggcaa   420
gaggtcngcc ccgctcaacc ccgacggtac cgtcgctgac acccccgaag ttgctgctgc   480
taagtgggct catctcgctg agatctccaa agctcgtgga atccctctcg tatacgctcc   540
cagatggtgg ggacctggtg ctccattgaa cgctga                576
```

<210> SEQ ID NO 6
<211> LENGTH: 645
<212> TYPE: DNA
<213> ORGANISM: Lygus hesperus
<220> FEATURE:
<221> NAME/KEY: misc_feature
<222> LOCATION: 612
<223> OTHER INFORMATION: n = A,T,C or G

<400> SEQUENCE: 6

```
ccaacatgta tctctcagtt gttggattgg tgatggcttc cgctgctttc gtcagctgcg    60
agccatcgaa tttcgcgtgt actggcgagt cgaactacaa gtatcctgtg gagggctcgt   120
```

| | |
|---|---|
| gccacaacta ctaccagtgc gaaaagggct ccactacgcc ttcaattcga gactgctcgc | 180 |
| tgccgctgct tcgatttcgg gatttcgatc cagtcaaatt ggagtgtgac tggtgctggc | 240 |
| gggtagactg ttcagccaaa cccgcacccc caccgactcc atcgccgact ccggcgccaa | 300 |
| cttcaaggcc tactgctgcg ccgactactg gaccaacctc agcgcccact actggaccca | 360 |
| cagcggcgcc aacctcagcg cccactgctg caccaacctc agctcccact gctgctccaa | 420 |
| ctccagcgcc cactgcgccg ccaactccag cgcccactgc ggcgcaact ccagcgccca | 480 |
| ctgcagcacc aacctcagct cccactgctg ctccaactcc agcgcctact gctgctccaa | 540 |
| ctccagcgcc tactgctgcg ccaacatcag cgccctctac tggacccact gtcgccccaa | 600 |
| ctcgcaggcc anctcaagaa cccacaatgg caaaaaaatc ttcga | 645 |

<210> SEQ ID NO 7
<211> LENGTH: 699
<212> TYPE: DNA
<213> ORGANISM: Lygus hesperus
<220> FEATURE:
<221> NAME/KEY: misc_feature
<222> LOCATION: 699
<223> OTHER INFORMATION: n = A,T,C or G
<400> SEQUENCE: 7

| | |
|---|---|
| caaataagaa acatgaagat agtaccgttc ttagttcttc tacttgttca aacggttctt | 60 |
| tccgaaacga cgccggcttc aaacaatcgc cgtattgttt gctaccacac aagttggagt | 120 |
| gcgtatcgtg tcccagaggc aaaatttaca gcgaagaaca tcaacccgta cctttgcact | 180 |
| catttaatat attcgtttgc caatgtattg gtaaatgaag caaccatcgt tcctggtgat | 240 |
| gcatggcagg atattgataa ccatcagttc agagattttg ttgagttgaa aaccacattc | 300 |
| aacgaaaacc tgaaaacgtt actcgcaata ggaggctaca gagaagggtc gtcgaagttc | 360 |
| accctatcg cagccacccc cacgaaaagg gcagcgtttg ctcgcaacac gctcaagttt | 420 |
| ttgaaaactt acggttttga cgggctcaac atcgattggc agttccctaa cgatcagcat | 480 |
| agaaatggca gtgttgaaga ctataagaac tttgtgtatt tgctgcaaga tatcgacaaa | 540 |
| gtcttcagag aggaagctgc agcttccggg aaacctaaaa tgatgttgac catttccgtt | 600 |
| ccgggtaata cgctgctaat agaaagtggc tatgatctac caaatctagc gaagtatgta | 660 |
| gagttcatga acgtcctgag ctacgattac cactttgcn | 699 |

<210> SEQ ID NO 8
<211> LENGTH: 707
<212> TYPE: DNA
<213> ORGANISM: Lygus hesperus
<220> FEATURE:
<221> NAME/KEY: misc_feature
<222> LOCATION: 707
<223> OTHER INFORMATION: n = A,T,C or G
<400> SEQUENCE: 8

| | |
|---|---|
| tccagttctt taacgaggta accatgtaca agactatctt acctgagttg ggagccttgg | 60 |
| atttgggttt gtgcccgaag atgttccatg gagaggcaca taatggtaaa aatcctgaac | 120 |
| aagacatcgt ggttattgaa gatttgtgtc ctcaaggtta caaagtgccg gaaaagttgt | 180 |
| ttttggacgc tgatcactta gtgatggcca tgaaaaaaat agggcaactt cacggattat | 240 |
| cttataaaat gaaagtatcg tctccagaga ggttgttcga attgaggaat atgctgatcc | 300 |
| cgaaggtgat tgacgattcg aaaggtctca atgatgcttg tctggccagg ggtttcaaac | 360 |
| ccttggtgga gtcgagcccc agttacagtg tagtgaataa agtttacaag aaactcgtcg | 420 |

-continued

```
tagcggatgc cgtggatgtt gcctatagtt tacagaagcc tgaagaacca ttcgccgtta      480
tcacccacgg tgatttcaat ggtaataaca tattgtataa gtatgatgcc agtggaaatg      540
tagtggatat gaaaatgata gattttggtt tcgcttctta tttggatcct gctgttgaca      600
tagctttctt cctgtacatg aactcttctc ctgaaactag gaagctgcac tgggattcat      660
tcctgaatgc atactgggag ggagtcatct ctgttgctgg tgatccn                    707
```

<210> SEQ ID NO 9
<211> LENGTH: 275
<212> TYPE: DNA
<213> ORGANISM: Lygus hesperus
<220> FEATURE:
<221> NAME/KEY: misc_feature
<222> LOCATION: 243, 249, 251, 252, 273
<223> OTHER INFORMATION: n = A,T,C or G

<400> SEQUENCE: 9

```
cgtgtgctga tcattcgata tcccggaaac gtgtttactt tcctttattg tgcataaata       60
cacttccgtg gcggttcgcg atgtcgaata caaaagtcgc gtcttccggt caacctaagc      120
tctcctccca agatctttcg actcttgacg tgacggcgct tacccattg tcgccagaag      180 tcatcagtag acaagcgacc atcaatatcg gtactattgg tcacgtggca catgggaaag      240
tcnactgtng nngaaagctg tgtctggtgt tcnaa                                 275
```

<210> SEQ ID NO 10
<211> LENGTH: 642
<212> TYPE: DNA
<213> ORGANISM: Lygus hesperus
<220> FEATURE:
<221> NAME/KEY: misc_feature
<222> LOCATION: 615, 616
<223> OTHER INFORMATION: n = A,T,C or G

<400> SEQUENCE: 10

```
tttttggttt tcattgaaaa tttcgataat tttccaaagt tttattatgg ttcaaattca       60
aaatgttttc tactgatttt gattctcaca gtataatttc gacgtggaag tgttaagggc      120
tcagtgatcg atggcaggga aagcttttg ataactattg gtaagtccga gtttgtaaga      180
tgacctcttt tcaaaagtgt gtaggatttg gtcggatatt tcctttaggg attctcagaa      240
atcacaatgt tgcatctcga aggtgcattc acggctcttc cgttttgtac aaaaagagga      300
aaaccagaga ggagaggaag ttgcccaaag ctattgttta ctctcccaaa tcgaaatgga      360
aacaaggcga gcccgttgac gtgtggaagc gtatgacagt ggcggaggta gcaaatacac      420
tgggtaaaga tgtaggacac gttttagaag ttatgtcgtt cattgacaac acggaacagt      480
acagaaaaga ccgtgatgtc atcgacaact tcaaagttat agaagaaata gtgaaaagt      540 cgggtcatcg atgtaggatg gctagtaagc ctacagaaac tgaagaaaaa gttttaaag      600 atgttggacg aaganncctt cggattacgt tgatcccagg cc                        642
```

<210> SEQ ID NO 11
<211> LENGTH: 721
<212> TYPE: DNA
<213> ORGANISM: Lygus hesperus
<220> FEATURE:
<221> NAME/KEY: misc_feature
<222> LOCATION: 720
<223> OTHER INFORMATION: n = A,T,C or G

<400> SEQUENCE: 11

```
tgcccgagtg cgtgtttcgt caaatagaaa cccgggtctt ttctgtaaga attaaatcgc    60
aatggctcct cctttctacg ctgatctagg taagaacgcc cgcgatgtct tcggtaaagg   120
gtaccatttc ggactcctga agctcgacgt caagaccaag actaacacgg gcgtcgaatt   180
cagcatcggc ggcgttcaaa acctcgaaac caaaaacgta gtcggctctc tcgagaccaa   240
gtacaaattc aaggagtatg gcgttacttt cacggagaaa tggaacactg acaacgtact   300
ggccactgaa atcgccgttg ctgatttctg cgatggagca aaaatgtccc ttgacacctc   360
ttttatccct cacaagggtg ataagaccct gcgattgaag ggcgaattca agaatgacac   420
ctgcgccatg aaccttgaaa gcgacttcaa gtctggcgga cctctcgtcc gaggtggcgc   480
tgtcctcggc tacggaggct ggctatgtgg ttacgccacg gccttcgacg ttagcaagag   540
taaactcacc gaaaacaaag tcaccatggg attcatcaca aaagatttca tcttgaacac   600
cgttatcaat gacggaagag tcttctctgg ttccatctac cacaaagtta acagcaagtt   660
ggaaactgga gtccagatct cgtgggcctc tgataacaac agcaccgact tcggcatcgn   720
c                                                                   721

<210> SEQ ID NO 12
<211> LENGTH: 724
<212> TYPE: DNA
<213> ORGANISM: Lygus hesperus
<220> FEATURE:
<221> NAME/KEY: misc_feature
<222> LOCATION: 665, 723, 724
<223> OTHER INFORMATION: n = A,T,C or G

<400> SEQUENCE: 12
attctgcttg ggttttttat ttagttgaac agttttccgt ggactcttat gacgataact    60
tcctcattcc aaatcttctt cgggactatc catcatttta atcagaagta gaagccgact   120
attctaaaaa ccacctatgg ggcctccatt cttcgcggat ctcggtaaaa actcgagaga   180
catcttcaat aaaggttata atttcgggct gcttaagttg gacataaaaa ccagaacaga   240
aaccggagtt gagttcgaaa tcggtggagt ccagaacctt gagacgaaaa atgtagccgg   300
ctcgctcgag actaagtaca aattcaagga cttcgggatc agcttttcgg agaaatggaa   360
tacggataat gttcttcagc tagaagtagc tgctgctgat atctgcgaag gagtcaaaat   420
gtcctgcatg agtatcatga ctccttcttc agatgaggag aaaggtggca ctgacaaaat   480
tttgagattc aagagtgaat ataagaatgc tatcatggct gtgaacttgg agagcgattt   540
caaagctggt ggtccgacct tgggagtctc tggcgttttt ggattaggtg atggttgct    600
cggagctata gcggcattag atactgagac ttcgaaagtg atgaccttct ctttgggaat   660
gggantttta accaaagact tcatactaaa caccgctgtt atcaacaagg aacagactt    720
cann                                                                724

<210> SEQ ID NO 13
<211> LENGTH: 692
<212> TYPE: DNA
<213> ORGANISM: Lygus hesperus

<400> SEQUENCE: 13
cgaaagcaaa caggacatca tatttcgcag gaataaattg gaagatccca tcacacgaga    60
aagcaaaccg gacgtcatat ttcgcagggt gcgaggtatc ctcaacaagc tcactcctga   120
gaaattcgat aagctaagcg atgacctctt gaaagaagaa tttaattctg atgtcattct   180
caaaggcgtc attctattgg tgtttgaaaa agcactagat gagccgaagt acagtgctat   240
```

```
gtatgctcag ctctgccggc gactttgtga agagatccga agtgccgacc agcctgaacc    300
ctgccctttt cgccatttgc ttctgtccag ctgcaaagct cagtttgaga gccgttcgaa    360
gcacactagc agcaagcgga aatcgctcgg gaacataaag ttcatcggag agctttgcaa    420
acttggaatc cttcagcgcg acatcttgta caggtgtttg atccaacttc tcgaacacaa    480
gaccaagacg cctgacgaaa tggccgaaga tcttgagtgc gtctgtcaga tcctccgcac    540
ttgcggccac atcttggaca acgaggaagc tcagaagctg atgaatcaac ttttttgatcg    600 tatggcgtcc ctctccaaga acgtcaacct gccgatccgg atccgcttca tgctccgtga    660
cattatcgag ctccggaggg ataactgggt tc                                   692
```

```
<210> SEQ ID NO 14
<211> LENGTH: 572
<212> TYPE: DNA
<213> ORGANISM: Lygus hesperus
<220> FEATURE:
<221> NAME/KEY: misc_feature
<222> LOCATION: 12, 410, 564
<223> OTHER INFORMATION: n = A,T,C or G

<400> SEQUENCE: 14
ctaactttcc tnttccgcgt tgttgcgttc ctgtgaaatt tcactaaaat tgtgattatt      60
ttattgtact cagaactata cctacttcgt atttcgattt gaatacattc caagggcttt    120
cgcatgactc aaactttctt ctagaagtgg tttgttgcga cgtgttgagt tcaatagtgt    180
ggtattcaca accggtttcg cccattgggc catcaacgag tattttccag gtgatgatct    240
attgatatgg ggggcgtagc cgcttcaagt cctttgccag acgaagaacc ccgacctgaa    300
gctccaggca gcaggaaggc agacgaagta cctgctgaga gtggtcagaa ccccgcagga    360
caacctcacc cagatggcgc caaggaagaa gagaacggag ataacgaggn aaaggcctgg    420
ccttataaaa gccgatggat ctataaattg ggattgccca tgtttgggag ggatggcaca    480
tgggccctgt ggcgatgagt tcagagctgc tttctcctgt ttccactatt ccactgctga    540
acaaaaaggc tccgactgtt tggnaaccgt tc                                   572
```

```
<210> SEQ ID NO 15
<211> LENGTH: 730
<212> TYPE: DNA
<213> ORGANISM: Lygus hesperus
<220> FEATURE:
<221> NAME/KEY: misc_feature
<222> LOCATION: 332
<223> OTHER INFORMATION: n = A,T,C or G

<400> SEQUENCE: 15
cacaaaaagc tccatacagg tgaacgccct ttcaaatgcg cacactgcgt tcggactttc      60
agccggaaag agcacttagt acggcatgcc cactctcata caggacaaaa actcttcaac    120
tgcgacgtct gcgggaaaag cttcagtcgg aaagacaacg tacggaaaca ccggaaaacg    180
catgaaacga caggtccgta ctcttgcgag ttctgcggta tgcagttcaa cgttcggccg    240
tactatataa tgcacaaaaa caagcacaaa gacgggtcgt gcgtccttga agtgaagaag    300
gttgatgttg aggagtctat cacgtacgaa gntcaggaag agtctccaga tgttcattcg    360
aacgaatcca attccttcca acaggtaaca tctagcacat ccacttcaat actggaaaaa    420
gcgttgacgc aagaaggctg aactttggac ttccttgaatt aacttaggc caaactatta    480 cagagttgac aagtatggag tgtgctcaga ggattagttg gtggaagtaa ctagtccaga    540
```

```
agctattcag aattaagaac tagaattgaa tgcaacagca atcagtttgc cctttcagtt      600
tgtggtttgt ttttctgttg gaaactatct ctcgggcatg aataaggaga atgtgtacca      660
agtatttcag tcttcctctg ctctgtgatg taactctgtg cttcttttcct atactcgcgt     720 tggtaatcaa                                                            730
```

```
<210> SEQ ID NO 16
<211> LENGTH: 568
<212> TYPE: DNA
<213> ORGANISM: Lygus hesperus
<220> FEATURE:
<221> NAME/KEY: misc_feature
<222> LOCATION: 165, 166, 523
<223> OTHER INFORMATION: n = A,T,C or G

<400> SEQUENCE: 16
aagaattgta atcaatatc aaaatggaga tgatgaagtc agatgtcgac tgaaaagaat       60
gtttggattc caagagatcc aaaagctcat taaatataac gtaaatactg tgctgtccat     120
ggactggctt gaccgtaatg ccaaaaactg tccgaaatga aacgnnccca ttcagaaaat     180
cagtggatgt aaccatatgg tatgctggaa atgcaaaaca tcttttttgct ggcactgcct    240 atgctttacg tgcataggat agtaaggacg tgagatgatc ctgtagttac agctctcttg    300
ccactgacta cctagaaata tcgcactagt catagtcagc caccctcctc tacctcgcca     360
ttatctcatt tgggctgtga caaacacaaa cctcgtgtat atctcgtata cattactatg    420
taccttgttt gcgctgtgac atctcaggaa cccttgata tgaaaattta agtggtaaaa     480 aaacttttttt acgattccga aaaaaaaaaa aaaaaaaaac ccnactttct tgtacaaagt   540
tggcattata agaaagcatt gcttatca                                        568
```

```
<210> SEQ ID NO 17
<211> LENGTH: 714
<212> TYPE: DNA
<213> ORGANISM: Lygus hesperus
<220> FEATURE:
<221> NAME/KEY: misc_feature
<222> LOCATION: 360, 361, 362, 363
<223> OTHER INFORMATION: n = A,T,C or G

<400> SEQUENCE: 17
gcctctcttc aagttttttgc ggtgtcggaa tgtcaaatta ataattgtt ccgatcaaat      60 taatatgtct agcatacgat ttcttagaaa attcagtgga tttagaatca gtggttctct    120
agtagtgggg cagtgtggtg cgcagaaaat ttgcagctta ggtcatttga aatctcaaga   180
gaactctagt ttactaagat ttaccggtgt tagtacgaga aatttccatt tgggagtgcc    240
atctctcgcc aagaaagact actacgagat cttgggcatc tctagaaacg cgtcggtcaa    300
ggaagtgaaa aaagcgtact atcagctggc caagaaatac catccagaca cgaataaaan   360
nnntccgaac gccgccaaga agtttcaaga agtatcagaa gcctatgagg tactgagtga    420
cgacaccaag aggaaacaat atgatcaatg gggtacgacg tcggagcaga tgggccgaga   480
aggtgctggt acaggtccag gtaacatggg cggcttcaac tggcagtacc gggcttccgt   540
ggaccctcag gagctcttca ggaagatctt tggagacgct gcaggcggat tttccaccgg    600
attcgacgat ttcgctgagt ctagattcgg tcacggtgct gccgaagaaa ttctaatgaa    660 actcacctttc tctcaagccg tgcggggagt gagcaaagaa atatacgtta atgt          714
```

```
<210> SEQ ID NO 18
<211> LENGTH: 716
```

```
<212> TYPE: DNA
<213> ORGANISM: Lygus hesperus
<220> FEATURE:
<221> NAME/KEY: misc_feature
<222> LOCATION: 10, 614, 708
<223> OTHER INFORMATION: n = A,T,C or G

<400> SEQUENCE: 18
gatgatcacn tttacggcta atactcgtag atctccagtt tcgatacaaa tttgaattca      60
acgagataac cgaatgaaat gacttggaaa tcagcttaaa agcagtgaac tcagcggtag     120
aggggaaaat gtctcactcc gactcaagaa cagggaaaac ctccagaagt acgaatgagt     180
cgaaatcagg agcctcgggg cgacagaaaa cttcaagaac tgagccgaaa accccgaaaa     240
ctgagtcaaa aacctcgaag tcagcgtcga aaacctcgaa gtcagaaggg aagtctgtgt     300
tgtctgaaag tagagataaa agtaataaat tttcaaaaag cgaatctgag tcgtatcgca     360
agtccgatgc gagggacag cgggacgagg caccaggacc gtcagacagc agaacaggaa      420
aagacgtcac tggggatagg aaaactaaga aacagaaaag tgagaaaggg gtcgacggat     480
ctactggaga atcgaagaaa ctcccagtgt cgtcctcaag aacgtcggaa gcgccgcgga     540
acatccgaga tctcttgagg aggatcaacg aggagaacga atctcagcca acaccttctt     600
ctcgtctgaa agancccaag ccggagagga cgaagagtaa agttccatcc aaagcaccgc     660
aggcgagtat tccagatagg gacgtggtac gagcaaaagc tgcggaancg gccttg        716

<210> SEQ ID NO 19
<211> LENGTH: 718
<212> TYPE: DNA
<213> ORGANISM: Lygus hesperus
<220> FEATURE:
<221> NAME/KEY: misc_feature
<222> LOCATION: 717, 718
<223> OTHER INFORMATION: n = A,T,C or G

<400> SEQUENCE: 19
gttcaccaag gaagtatcgc accacattct ctgccaaact acagcaggat cccaaaccac      60
cggaatgaac accattttgg ctctcgcaag tctgttgggc tgctgtctgg cggcgtccgt     120
tccggattcg aagtgggatt cttcaaggc caaatacgga aaaacgtacg acgacccaaa      180
agtcgatagt gagagacgta acaactacgg aaaaacgcta gagatgatca aggctcacaa     240
cgcactctat ggacagggcc gggtgtccta ctacctggca gagaaccatc ttgcagactt     300
gtcgtccagt gaacgaatga agttaagagg attcagaaaa tccgaaagtc aatcgggcgg     360
cagaatccac cagcacactg gattgggccg acccgattcc gtcgattggc gaaacaaaag     420
cgttgtgacc agcgtcaaaa atcaaggaca atgtggtagc tgctgggctt tcagtgcgac     480
tgcagcagtg gaatcgcaat acgctatcaa aaccgggcaa ttagtggatc tcagcgagca     540
gcaggtagtg gactgtgacc gtaatggtca cgcttgcaag tatggtgaca accttgacgc     600
gttagggtat atcgaggaag aaggtcagga gcttctttcc tcttatccct acattgctga     660
gccagagact tgtcaatacg cagcagataa agtgaaggtg aagattgcga gtttccnn    718

<210> SEQ ID NO 20
<211> LENGTH: 638
<212> TYPE: DNA
<213> ORGANISM: Lygus hesperus
<220> FEATURE:
<221> NAME/KEY: misc_feature
<222> LOCATION: 629
<223> OTHER INFORMATION: n = A,T,C or G
```

<400> SEQUENCE: 20

```
gtcttaagtg atgaagatgt tgtgttaggt ttaccgggcg tgccaggata ccatgctatg    60
gaaatggcaa cgtctgaagg ttttcctttc acagcaagtc gaccacaagg aagttccaat   120
aagcggtggt tgtttaacat caatgagaat gccgagaaga gatccttaat cgccatggac   180
cccttattgg tgaaagtgtt agaatcgaag agggttcaga gagatcgagg gttgattccg   240
tgtaccgttt ttgtagactg cttgaaggat tcacgaatag cgaatgaatc ttacctcaca   300
cccggtaaga ctaggatctt ctctatctca ccggttgact ttacgattga gtttcggaag   360
tatttccttg atatcctagc ggcgcaacaa caaagtcgat tccacctaga gcatatggta   420
ggtatgaatg ttcattcgct tgagtggact ttactagccc gccgtatcca atctgtgggt   480
tctgcagtga tctgtggtga ttactcgaac tttggtcctg gtttggatag cgaagttgtt   540
gcagctgttg gggacgtttg ggctgattgg tatgagtttt acgagaccgc tcagggcgtc   600
tcggaagagg agagaaagcg acgccgccna agtaagaa                           638
```

<210> SEQ ID NO 21
<211> LENGTH: 260
<212> TYPE: DNA
<213> ORGANISM: Lygus hesperus
<220> FEATURE:
<221> NAME/KEY: misc_feature
<222> LOCATION: 59
<223> OTHER INFORMATION: n = A,T,C or G

<400> SEQUENCE: 21

```
catggcgtac ggtgtaacaa gagtcgtgtt ccgctgcgag gaagctcagg aatccggana    60
attggatctg tcggaatgtc aactcatgca ggtgccggac gcggtctacc acttgatgag   120
gcacacggaa ctgaaggcgt gtaatctctc aagcaacgtc atcaccaaaa ttcccccgaa   180
attcgcggtc aacttttctc tcattacaga gctgaacctg gcgcacaacc agatgagcaa   240
actcccggac gagctcgccg                                               260
```

<210> SEQ ID NO 22
<211> LENGTH: 23
<212> TYPE: DNA
<213> ORGANISM: Lygus hesperus

<400> SEQUENCE: 22

```
aagaggtaca aatgtctttc ctg                                            23
```

<210> SEQ ID NO 23
<211> LENGTH: 19
<212> TYPE: RNA
<213> ORGANISM: Artificial Sequence
<220> FEATURE:
<223> OTHER INFORMATION: primer

<400> SEQUENCE: 23

```
gagguacaaa ugucuuucc                                                 19
```

<210> SEQ ID NO 24
<211> LENGTH: 19
<212> TYPE: RNA
<213> ORGANISM: Artificial Sequence
<220> FEATURE:
<223> OTHER INFORMATION: primer

<400> SEQUENCE: 24

```
ggaaagacau uuguaccuc                                                 19
```

```
<210> SEQ ID NO 25
<211> LENGTH: 23
<212> TYPE: DNA
<213> ORGANISM: Lygus hesperus

<400> SEQUENCE: 25
aagtcagtcc tacacgtgtc ctc                                              23

<210> SEQ ID NO 26
<211> LENGTH: 19
<212> TYPE: RNA
<213> ORGANISM: Artificial Sequence
<220> FEATURE:
<223> OTHER INFORMATION: primer

<400> SEQUENCE: 26
gucaguccua cacgugucc                                                   19

<210> SEQ ID NO 27
<211> LENGTH: 19
<212> TYPE: RNA
<213> ORGANISM: Artificial Sequence
<220> FEATURE:
<223> OTHER INFORMATION: primer

<400> SEQUENCE: 27
ggacacgugu aggacugac                                                   19

<210> SEQ ID NO 28
<211> LENGTH: 22
<212> TYPE: DNA
<213> ORGANISM: Lygus hesperus

<400> SEQUENCE: 28
aacaacgttc gccaggattt tt                                               22

<210> SEQ ID NO 29
<211> LENGTH: 19
<212> TYPE: RNA
<213> ORGANISM: Artificial Sequence
<220> FEATURE:
<223> OTHER INFORMATION: primer

<400> SEQUENCE: 29
caacguucgc caggauuuu                                                   19

<210> SEQ ID NO 30
<211> LENGTH: 19
<212> TYPE: RNA
<213> ORGANISM: Artificial Sequence
<220> FEATURE:
<223> OTHER INFORMATION: primer

<400> SEQUENCE: 30
aaaauccugg cgaacguug                                                   19

<210> SEQ ID NO 31
<211> LENGTH: 23
<212> TYPE: DNA
<213> ORGANISM: Lygus hesperus

<400> SEQUENCE: 31
aagactgctg acggaataac gaa                                              23
```

```
<210> SEQ ID NO 32
<211> LENGTH: 19
<212> TYPE: RNA
<213> ORGANISM: Artificial Sequence
<220> FEATURE:
<223> OTHER INFORMATION: primer

<400> SEQUENCE: 32
gacugcugac ggaauaacg                                              19

<210> SEQ ID NO 33
<211> LENGTH: 19
<212> TYPE: RNA
<213> ORGANISM: Artificial Sequence
<220> FEATURE:
<223> OTHER INFORMATION: primer

<400> SEQUENCE: 33
cguuauuccg ucagcaguc                                              19

<210> SEQ ID NO 34
<211> LENGTH: 23
<212> TYPE: DNA
<213> ORGANISM: Lygus hesperus

<400> SEQUENCE: 34
aaccccgacg gcaccgtcgc tga                                         23

<210> SEQ ID NO 35
<211> LENGTH: 19
<212> TYPE: RNA
<213> ORGANISM: Artificial Sequence
<220> FEATURE:
<223> OTHER INFORMATION: primer

<400> SEQUENCE: 35
ccccgacggc accgucgcu                                              19

<210> SEQ ID NO 36
<211> LENGTH: 19
<212> TYPE: RNA
<213> ORGANISM: Artificial Sequence
<220> FEATURE:
<223> OTHER INFORMATION: primer

<400> SEQUENCE: 36
agcgacggug ccgucgggg                                              19

<210> SEQ ID NO 37
<211> LENGTH: 23
<212> TYPE: DNA
<213> ORGANISM: Lygus hesperus

<400> SEQUENCE: 37
aagatctcca aagctcgtgg aat                                         23

<210> SEQ ID NO 38
<211> LENGTH: 19
<212> TYPE: RNA
<213> ORGANISM: Artificial Sequence
<220> FEATURE:
<223> OTHER INFORMATION: primer

<400> SEQUENCE: 38
gaucuccaaa gcucgugga                                              19
```

```
<210> SEQ ID NO 39
<211> LENGTH: 19
<212> TYPE: RNA
<213> ORGANISM: Artificial Sequence
<220> FEATURE:
<223> OTHER INFORMATION: primer

<400> SEQUENCE: 39
uccacgagcu uuggagauc                                               19

<210> SEQ ID NO 40
<211> LENGTH: 23
<212> TYPE: DNA
<213> ORGANISM: Lygus hesperus

<400> SEQUENCE: 40
aaattacccg cggaggatac tca                                          23

<210> SEQ ID NO 41
<211> LENGTH: 19
<212> TYPE: RNA
<213> ORGANISM: Artificial Sequence
<220> FEATURE:
<223> OTHER INFORMATION: primer

<400> SEQUENCE: 41
auuacccgcg gaggauacu                                               19

<210> SEQ ID NO 42
<211> LENGTH: 19
<212> TYPE: RNA
<213> ORGANISM: Artificial Sequence
<220> FEATURE:
<223> OTHER INFORMATION: primer

<400> SEQUENCE: 42
aguauccucc gcggguaau                                               19

<210> SEQ ID NO 43
<211> LENGTH: 23
<212> TYPE: DNA
<213> ORGANISM: Lygus hesperus

<400> SEQUENCE: 43
aattgtggct tcagctcccg tat                                          23

<210> SEQ ID NO 44
<211> LENGTH: 19
<212> TYPE: RNA
<213> ORGANISM: Artificial Sequence
<220> FEATURE:
<223> OTHER INFORMATION: primer

<400> SEQUENCE: 44
uuguggcuuc agcucccgu                                               19

<210> SEQ ID NO 45
<211> LENGTH: 19
<212> TYPE: RNA
<213> ORGANISM: Artificial Sequence
<220> FEATURE:
<223> OTHER INFORMATION: primer

<400> SEQUENCE: 45
```
acgggagcug aagccacaa                                                    19

<210> SEQ ID NO 46
<211> LENGTH: 23
<212> TYPE: DNA
<213> ORGANISM: Lygus hesperus
<220> FEATURE:
<221> NAME/KEY: misc_feature
<222> LOCATION: 13
<223> OTHER INFORMATION: n = A,T,C or G

<400> SEQUENCE: 46
aactctcttg tancctcacc aca                                               23

<210> SEQ ID NO 47
<211> LENGTH: 19
<212> TYPE: RNA
<213> ORGANISM: Artificial Sequence
<220> FEATURE:
<223> OTHER INFORMATION: primer
<220> FEATURE:
<221> NAME/KEY: misc_feature
<222> LOCATION: 11
<223> OTHER INFORMATION: n = A,T,C or G

<400> SEQUENCE: 47
cucucuugua nccucacca                                                    19

<210> SEQ ID NO 48
<211> LENGTH: 16
<212> TYPE: RNA
<213> ORGANISM: Artificial Sequence
<220> FEATURE:
<223> OTHER INFORMATION: primer

<400> SEQUENCE: 48
uggugaggca agagag                                                       16

<210> SEQ ID NO 49
<211> LENGTH: 23
<212> TYPE: DNA
<213> ORGANISM: Lygus hesperus

<400> SEQUENCE: 49
aagtctttaa ggacggattt acg                                               23

<210> SEQ ID NO 50
<211> LENGTH: 19
<212> TYPE: RNA
<213> ORGANISM: Artificial Sequence
<220> FEATURE:
<223> OTHER INFORMATION: primer

<400> SEQUENCE: 50
gucuuuaagg acggauuua                                                    19

<210> SEQ ID NO 51
<211> LENGTH: 19
<212> TYPE: RNA
<213> ORGANISM: Artificial Sequence
<220> FEATURE:
<223> OTHER INFORMATION: primer

<400> SEQUENCE: 51
uaaauccguc cuuaaagac                                                    19

```
<210> SEQ ID NO 52
<211> LENGTH: 23
<212> TYPE: DNA
<213> ORGANISM: Lygus hesperus

<400> SEQUENCE: 52
aatgcgtgtt ggctcatctg tca                                          23

<210> SEQ ID NO 53
<211> LENGTH: 19
<212> TYPE: RNA
<213> ORGANISM: Artificial Sequence
<220> FEATURE:
<223> OTHER INFORMATION: primer

<400> SEQUENCE: 53
ugcguguugg cucaucugu                                               19

<210> SEQ ID NO 54
<211> LENGTH: 19
<212> TYPE: RNA
<213> ORGANISM: Artificial Sequence
<220> FEATURE:
<223> OTHER INFORMATION: primer

<400> SEQUENCE: 54
acagaugagc caacacgca                                               19

<210> SEQ ID NO 55
<211> LENGTH: 23
<212> TYPE: DNA
<213> ORGANISM: Lygus hesperus

<400> SEQUENCE: 55
aagctggtgg tcgtctgaag gat                                          23

<210> SEQ ID NO 56
<211> LENGTH: 19
<212> TYPE: RNA
<213> ORGANISM: Artificial Sequence
<220> FEATURE:
<223> OTHER INFORMATION: primer

<400> SEQUENCE: 56
gcugguggus gucugaagg                                               19
```

(Note: SEQ ID NO 56 sequence reads: gcuggugguc gucugaagg)

```
<210> SEQ ID NO 57
<211> LENGTH: 19
<212> TYPE: RNA
<213> ORGANISM: Artificial Sequence
<220> FEATURE:
<223> OTHER INFORMATION: primer

<400> SEQUENCE: 57
ccuucagacg accaccagc                                               19

<210> SEQ ID NO 58
<211> LENGTH: 23
<212> TYPE: DNA
<213> ORGANISM: Lygus hesperus

<400> SEQUENCE: 58
aacactcgga tgaaatcact gtg                                          23

<210> SEQ ID NO 59
```

```
<211> LENGTH: 19
<212> TYPE: RNA
<213> ORGANISM: Artificial Sequence
<220> FEATURE:
<223> OTHER INFORMATION: primer

<400> SEQUENCE: 59
cacucggaug aaaucacug                                              19

<210> SEQ ID NO 60
<211> LENGTH: 19
<212> TYPE: RNA
<213> ORGANISM: Artificial Sequence
<220> FEATURE:
<223> OTHER INFORMATION: primer

<400> SEQUENCE: 60
cagugauuuc auccgagug                                              19

<210> SEQ ID NO 61
<211> LENGTH: 23
<212> TYPE: DNA
<213> ORGANISM: Lygus hesperus

<400> SEQUENCE: 61
aatcagtatc acgctcagga tgt                                         23

<210> SEQ ID NO 62
<211> LENGTH: 19
<212> TYPE: RNA
<213> ORGANISM: Artificial Sequence
<220> FEATURE:
<223> OTHER INFORMATION: primer

<400> SEQUENCE: 62
ucaguaucac gcucaggau                                              19

<210> SEQ ID NO 63
<211> LENGTH: 19
<212> TYPE: RNA
<213> ORGANISM: Artificial Sequence
<220> FEATURE:
<223> OTHER INFORMATION: primer

<400> SEQUENCE: 63
auccugagcg ugauacuga                                              19

<210> SEQ ID NO 64
<211> LENGTH: 23
<212> TYPE: DNA
<213> ORGANISM: Lygus hesperus

<400> SEQUENCE: 64
aacacccatg aagtcgctgt cgc                                         23

<210> SEQ ID NO 65
<211> LENGTH: 19
<212> TYPE: RNA
<213> ORGANISM: Artificial Sequence
<220> FEATURE:
<223> OTHER INFORMATION: primer

<400> SEQUENCE: 65
cacccaugaa gucgcuguc                                              19
```

```
<210> SEQ ID NO 66
<211> LENGTH: 19
<212> TYPE: RNA
<213> ORGANISM: Artificial Sequence
<220> FEATURE:
<223> OTHER INFORMATION: primer

<400> SEQUENCE: 66
gacagcgacu ucaugggug                                                    19

<210> SEQ ID NO 67
<211> LENGTH: 23
<212> TYPE: DNA
<213> ORGANISM: Lygus hesperus

<400> SEQUENCE: 67
aagatctcca aagctcgtgg aat                                               23

<210> SEQ ID NO 68
<211> LENGTH: 19
<212> TYPE: RNA
<213> ORGANISM: Artificial Sequence
<220> FEATURE:
<223> OTHER INFORMATION: primer

<400> SEQUENCE: 68
gaucuccaaa gcucgugga                                                    19

<210> SEQ ID NO 69
<211> LENGTH: 19
<212> TYPE: RNA
<213> ORGANISM: Artificial Sequence
<220> FEATURE:
<223> OTHER INFORMATION: primer

<400> SEQUENCE: 69
uccacgagcu uuggagauc                                                    19

<210> SEQ ID NO 70
<211> LENGTH: 23
<212> TYPE: DNA
<213> ORGANISM: Lygus hesperus

<400> SEQUENCE: 70
aactacaagt atcctgtgga ggg                                               23

<210> SEQ ID NO 71
<211> LENGTH: 19
<212> TYPE: RNA
<213> ORGANISM: Artificial Sequence
<220> FEATURE:
<223> OTHER INFORMATION: primer

<400> SEQUENCE: 71
cuacaaguau ccuguggag                                                    19

<210> SEQ ID NO 72
<211> LENGTH: 19
<212> TYPE: RNA
<213> ORGANISM: Artificial Sequence
<220> FEATURE:
<223> OTHER INFORMATION: primer

<400> SEQUENCE: 72
cuccacagga uacuuguag                                                    19
```

<210> SEQ ID NO 73
<211> LENGTH: 23
<212> TYPE: DNA
<213> ORGANISM: Lygus hesperus

<400> SEQUENCE: 73
aaattggagt gtgactggtg ctg                                                23

<210> SEQ ID NO 74
<211> LENGTH: 19
<212> TYPE: RNA
<213> ORGANISM: Artificial Sequence
<220> FEATURE:
<223> OTHER INFORMATION: primer

<400> SEQUENCE: 74
auuggagugu gacuggugc                                                    19

<210> SEQ ID NO 75
<211> LENGTH: 19
<212> TYPE: RNA
<213> ORGANISM: Artificial Sequence
<220> FEATURE:
<223> OTHER INFORMATION: primer

<400> SEQUENCE: 75
gcaccaguca cacuccaau                                                    19

<210> SEQ ID NO 76
<211> LENGTH: 23
<212> TYPE: DNA
<213> ORGANISM: Lygus hesperus

<400> SEQUENCE: 76
aacatcagac gccctctact gga                                                23

<210> SEQ ID NO 77
<211> LENGTH: 19
<212> TYPE: RNA
<213> ORGANISM: Artificial Sequence
<220> FEATURE:
<223> OTHER INFORMATION: primer

<400> SEQUENCE: 77
caucagacgc ccucuacug                                                    19

<210> SEQ ID NO 78
<211> LENGTH: 19
<212> TYPE: RNA
<213> ORGANISM: Artificial Sequence
<220> FEATURE:
<223> OTHER INFORMATION: primer

<400> SEQUENCE: 78
caguagaggg cgucugaug                                                    19

<210> SEQ ID NO 79
<211> LENGTH: 23
<212> TYPE: DNA
<213> ORGANISM: Lygus hesperus

<400> SEQUENCE: 79
aaacggttct ttccgaaacg acg                                                23

```
<210> SEQ ID NO 80
<211> LENGTH: 19
<212> TYPE: RNA
<213> ORGANISM: Artificial Sequence
<220> FEATURE:
<223> OTHER INFORMATION: primer

<400> SEQUENCE: 80
acgguucuuu ccgaaacga                                              19

<210> SEQ ID NO 81
<211> LENGTH: 19
<212> TYPE: RNA
<213> ORGANISM: Artificial Sequence
<220> FEATURE:
<223> OTHER INFORMATION: primer

<400> SEQUENCE: 81
ucguuucgga aagaaccgu                                              19

<210> SEQ ID NO 82
<211> LENGTH: 23
<212> TYPE: DNA
<213> ORGANISM: Lygus hesperus

<400> SEQUENCE: 82
aaccatcgtt cctggtgatg cat                                         23

<210> SEQ ID NO 83
<211> LENGTH: 19
<212> TYPE: RNA
<213> ORGANISM: Artificial Sequence
<220> FEATURE:
<223> OTHER INFORMATION: primer

<400> SEQUENCE: 83
ccaucguucc uggugaugc                                              19

<210> SEQ ID NO 84
<211> LENGTH: 19
<212> TYPE: RNA
<213> ORGANISM: Artificial Sequence
<220> FEATURE:
<223> OTHER INFORMATION: primer

<400> SEQUENCE: 84
gcaucaccag gaacgaugg                                              19

<210> SEQ ID NO 85
<211> LENGTH: 23
<212> TYPE: DNA
<213> ORGANISM: Lygus hesperus

<400> SEQUENCE: 85
aaagtcttca gagaggaagc tgc                                         23

<210> SEQ ID NO 86
<211> LENGTH: 19
<212> TYPE: RNA
<213> ORGANISM: Artificial Sequence
<220> FEATURE:
<223> OTHER INFORMATION: primer

<400> SEQUENCE: 86
agucuucaga gaggaagcu                                              19
```

```
<210> SEQ ID NO 87
<211> LENGTH: 19
<212> TYPE: RNA
<213> ORGANISM: Artificial Sequence
<220> FEATURE:
<223> OTHER INFORMATION: primer

<400> SEQUENCE: 87
agcuuccucu cugaagacu                                                19

<210> SEQ ID NO 88
<211> LENGTH: 23
<212> TYPE: DNA
<213> ORGANISM: Lygus hesperus

<400> SEQUENCE: 88
aagatgttcc atggagaggc aca                                           23

<210> SEQ ID NO 89
<211> LENGTH: 19
<212> TYPE: RNA
<213> ORGANISM: Artificial Sequence
<220> FEATURE:
<223> OTHER INFORMATION: primer

<400> SEQUENCE: 89
gauguuccau ggagaggca                                                19

<210> SEQ ID NO 90
<211> LENGTH: 19
<212> TYPE: RNA
<213> ORGANISM: Artificial Sequence
<220> FEATURE:
<223> OTHER INFORMATION: primer

<400> SEQUENCE: 90
ugccucucca uggaacauc                                                19

<210> SEQ ID NO 91
<211> LENGTH: 23
<212> TYPE: DNA
<213> ORGANISM: Lygus hesperus

<400> SEQUENCE: 91
aaatagggca acttcacgga tta                                           23

<210> SEQ ID NO 92
<211> LENGTH: 19
<212> TYPE: RNA
<213> ORGANISM: Artificial Sequence
<220> FEATURE:
<223> OTHER INFORMATION: primer

<400> SEQUENCE: 92
auagggcaac uucacggau                                                19

<210> SEQ ID NO 93
<211> LENGTH: 19
<212> TYPE: RNA
<213> ORGANISM: Artificial Sequence
<220> FEATURE:
<223> OTHER INFORMATION: primer

<400> SEQUENCE: 93
auccgugaag uugcccuau                                                19
```

<210> SEQ ID NO 94
<211> LENGTH: 23
<212> TYPE: DNA
<213> ORGANISM: Lygus hesperus

<400> SEQUENCE: 94
aagaaccatt cgccgttatc acc                                              23

<210> SEQ ID NO 95
<211> LENGTH: 19
<212> TYPE: RNA
<213> ORGANISM: Artificial Sequence
<220> FEATURE:
<223> OTHER INFORMATION: primer

<400> SEQUENCE: 95
gaaccauucg ccguuauca                                                   19

<210> SEQ ID NO 96
<211> LENGTH: 19
<212> TYPE: RNA
<213> ORGANISM: Artificial Sequence
<220> FEATURE:
<223> OTHER INFORMATION: primer

<400> SEQUENCE: 96
ugauaacggc gaaugguuc                                                   19

<210> SEQ ID NO 97
<211> LENGTH: 23
<212> TYPE: DNA
<213> ORGANISM: Lygus hesperus

<400> SEQUENCE: 97
aagctgcact gggattcatt cct                                              23

<210> SEQ ID NO 98
<211> LENGTH: 19
<212> TYPE: RNA
<213> ORGANISM: Artificial Sequence
<220> FEATURE:
<223> OTHER INFORMATION: primer

<400> SEQUENCE: 98
gcugcacugg gauucauuc                                                   19

<210> SEQ ID NO 99
<211> LENGTH: 19
<212> TYPE: RNA
<213> ORGANISM: Artificial Sequence
<220> FEATURE:
<223> OTHER INFORMATION: primer

<400> SEQUENCE: 99
gaaugaaucc cagugcagc                                                   19

<210> SEQ ID NO 100
<211> LENGTH: 23
<212> TYPE: DNA
<213> ORGANISM: Lygus hesperus

<400> SEQUENCE: 100
aatacaaaag tcgcgtcttc cgg                                              23

```
<210> SEQ ID NO 101
<211> LENGTH: 19
<212> TYPE: RNA
<213> ORGANISM: Artificial Sequence
<220> FEATURE:
<223> OTHER INFORMATION: primer

<400> SEQUENCE: 101
uacaaaaguc gcgucuucc                                                 19

<210> SEQ ID NO 102
<211> LENGTH: 19
<212> TYPE: RNA
<213> ORGANISM: Artificial Sequence
<220> FEATURE:
<223> OTHER INFORMATION: primer

<400> SEQUENCE: 102
ggaagacgcg acuuuugua                                                 19

<210> SEQ ID NO 103
<211> LENGTH: 23
<212> TYPE: DNA
<213> ORGANISM: Lygus hesperus

<400> SEQUENCE: 103
aagatctttc gactcttgac gtg                                            23

<210> SEQ ID NO 104
<211> LENGTH: 19
<212> TYPE: RNA
<213> ORGANISM: Artificial Sequence
<220> FEATURE:
<223> OTHER INFORMATION: primer

<400> SEQUENCE: 104
gaucuuucga cucuugacg                                                 19

<210> SEQ ID NO 105
<211> LENGTH: 19
<212> TYPE: RNA
<213> ORGANISM: Artificial Sequence
<220> FEATURE:
<223> OTHER INFORMATION: primer

<400> SEQUENCE: 105
cgucaagagu cgaaagauc                                                 19

<210> SEQ ID NO 106
<211> LENGTH: 23
<212> TYPE: DNA
<213> ORGANISM: Lygus hesperus

<400> SEQUENCE: 106
aatatcggta ctattggtca cgt                                            23

<210> SEQ ID NO 107
<211> LENGTH: 19
<212> TYPE: RNA
<213> ORGANISM: Artificial Sequence
<220> FEATURE:
<223> OTHER INFORMATION: primer

<400> SEQUENCE: 107
uaucgguacu auuggucac                                                 19
```

```
<210> SEQ ID NO 108
<211> LENGTH: 19
<212> TYPE: RNA
<213> ORGANISM: Artificial Sequence
<220> FEATURE:
<223> OTHER INFORMATION: primer

<400> SEQUENCE: 108
gugaccaaua guaccgaua                                                19

<210> SEQ ID NO 109
<211> LENGTH: 23
<212> TYPE: DNA
<213> ORGANISM: Lygus hesperus

<400> SEQUENCE: 109
aatttcgacg tggaagtgtt aag                                           23

<210> SEQ ID NO 110
<211> LENGTH: 19
<212> TYPE: RNA
<213> ORGANISM: Artificial Sequence
<220> FEATURE:
<223> OTHER INFORMATION: primer

<400> SEQUENCE: 110
uuucgacgug aaguguua                                                 19

<210> SEQ ID NO 111
<211> LENGTH: 19
<212> TYPE: RNA
<213> ORGANISM: Artificial Sequence
<220> FEATURE:
<223> OTHER INFORMATION: primer

<400> SEQUENCE: 111
uaacacuucc acgucgaaa                                                19

<210> SEQ ID NO 112
<211> LENGTH: 23
<212> TYPE: DNA
<213> ORGANISM: Lygus hesperus

<400> SEQUENCE: 112
aatgttgcat ctcgaaggtg caa                                           23

<210> SEQ ID NO 113
<211> LENGTH: 19
<212> TYPE: RNA
<213> ORGANISM: Artificial Sequence
<220> FEATURE:
<223> OTHER INFORMATION: primer

<400> SEQUENCE: 113
uguugcaucu cgaaggugc                                                19

<210> SEQ ID NO 114
<211> LENGTH: 19
<212> TYPE: RNA
<213> ORGANISM: Artificial Sequence
<220> FEATURE:
<223> OTHER INFORMATION: primer

<400> SEQUENCE: 114
```
gcaccuucga gaugcaaca                                                    19

<210> SEQ ID NO 115
<211> LENGTH: 23
<212> TYPE: DNA
<213> ORGANISM: Lygus hesperus

<400> SEQUENCE: 115
aacactgggt aaagatgtag gac                                               23

<210> SEQ ID NO 116
<211> LENGTH: 19
<212> TYPE: RNA
<213> ORGANISM: Artificial Sequence
<220> FEATURE:
<223> OTHER INFORMATION: primer

<400> SEQUENCE: 116
cacuggguaa agauguagg                                                    19

<210> SEQ ID NO 117
<211> LENGTH: 19
<212> TYPE: RNA
<213> ORGANISM: Artificial Sequence
<220> FEATURE:
<223> OTHER INFORMATION: primer

<400> SEQUENCE: 117
ccuacaucuu uacccagug                                                    19

<210> SEQ ID NO 118
<211> LENGTH: 23
<212> TYPE: DNA
<213> ORGANISM: Lygus hesperus

<400> SEQUENCE: 118
aacccgggtc ttttctgtaa aga                                               23

<210> SEQ ID NO 119
<211> LENGTH: 19
<212> TYPE: RNA
<213> ORGANISM: Artificial Sequence
<220> FEATURE:
<223> OTHER INFORMATION: primer

<400> SEQUENCE: 119
cccgggucuu uucuguaaa                                                    19

<210> SEQ ID NO 120
<211> LENGTH: 19
<212> TYPE: RNA
<213> ORGANISM: Artificial Sequence
<220> FEATURE:
<223> OTHER INFORMATION: primer

<400> SEQUENCE: 120
uuuacagaaa agacccggg                                                    19

<210> SEQ ID NO 121
<211> LENGTH: 23
<212> TYPE: DNA
<213> ORGANISM: Lygus hesperus

<400> SEQUENCE: 121
aaacctcgaa accaaaaacg tag                                               23

<210> SEQ ID NO 122
<211> LENGTH: 19
<212> TYPE: RNA
<213> ORGANISM: Artificial Sequence
<220> FEATURE:
<223> OTHER INFORMATION: primer

<400> SEQUENCE: 122
accucgaaac caaaaacgu                                              19

<210> SEQ ID NO 123
<211> LENGTH: 19
<212> TYPE: RNA
<213> ORGANISM: Artificial Sequence
<220> FEATURE:
<223> OTHER INFORMATION: primer

<400> SEQUENCE: 123
acguuuuugg uuucgaggu                                              19

<210> SEQ ID NO 124
<211> LENGTH: 23
<212> TYPE: DNA
<213> ORGANISM: Lygus hesperus

<400> SEQUENCE: 124
aagttggaaa ctggagtcca gat                                         23

<210> SEQ ID NO 125
<211> LENGTH: 19
<212> TYPE: RNA
<213> ORGANISM: Artificial Sequence
<220> FEATURE:
<223> OTHER INFORMATION: primer

<400> SEQUENCE: 125
guuggaaacu ggaguccag                                              19

<210> SEQ ID NO 126
<211> LENGTH: 19
<212> TYPE: RNA
<213> ORGANISM: Artificial Sequence
<220> FEATURE:
<223> OTHER INFORMATION: primer

<400> SEQUENCE: 126
cuggacucca guuuccaac                                              19

<210> SEQ ID NO 127
<211> LENGTH: 23
<212> TYPE: DNA
<213> ORGANISM: Lygus hesperus

<400> SEQUENCE: 127
aaatcttctt cgggactatc cat                                         23

<210> SEQ ID NO 128
<211> LENGTH: 19
<212> TYPE: RNA
<213> ORGANISM: Artificial Sequence
<220> FEATURE:
<223> OTHER INFORMATION: primer

<400> SEQUENCE: 128

```
aucuucuucg ggacuaucc                                           19

<210> SEQ ID NO 129
<211> LENGTH: 19
<212> TYPE: RNA
<213> ORGANISM: Artificial Sequence
<220> FEATURE:
<223> OTHER INFORMATION: primer

<400> SEQUENCE: 129
ggauaguccc gaagaagau                                           19

<210> SEQ ID NO 130
<211> LENGTH: 23
<212> TYPE: DNA
<213> ORGANISM: Lygus hesperus

<400> SEQUENCE: 130
aaaaccagaa cagaaaccgg agt                                      23

<210> SEQ ID NO 131
<211> LENGTH: 19
<212> TYPE: RNA
<213> ORGANISM: Artificial Sequence
<220> FEATURE:
<223> OTHER INFORMATION: primer

<400> SEQUENCE: 131
aaccagaaca gaaaccgga                                           19

<210> SEQ ID NO 132
<211> LENGTH: 19
<212> TYPE: RNA
<213> ORGANISM: Artificial Sequence
<220> FEATURE:
<223> OTHER INFORMATION: primer

<400> SEQUENCE: 132
uccgguuucu guucugguu                                           19

<210> SEQ ID NO 133
<211> LENGTH: 23
<212> TYPE: DNA
<213> ORGANISM: Lygus hesperus

<400> SEQUENCE: 133
aagtgatgac cttctctttg gga                                      23

<210> SEQ ID NO 134
<211> LENGTH: 19
<212> TYPE: RNA
<213> ORGANISM: Artificial Sequence
<220> FEATURE:
<223> OTHER INFORMATION: primer

<400> SEQUENCE: 134
gugaugaccu ucucuuugg                                           19

<210> SEQ ID NO 135
<211> LENGTH: 19
<212> TYPE: RNA
<213> ORGANISM: Artificial Sequence
<220> FEATURE:
<223> OTHER INFORMATION: primer

<400> SEQUENCE: 135
```

-continued

```
ccaaagagaa ggucaucac                                                19
```

<210> SEQ ID NO 136
<211> LENGTH: 23
<212> TYPE: DNA
<213> ORGANISM: Lygus hesperus

<400> SEQUENCE: 136

```
aacaggacat catatttcgc agg                                           23
```

<210> SEQ ID NO 137
<211> LENGTH: 19
<212> TYPE: RNA
<213> ORGANISM: Artificial Sequence
<220> FEATURE:
<223> OTHER INFORMATION: primer

<400> SEQUENCE: 137

```
caggacauca uauuucgca                                                19
```

<210> SEQ ID NO 138
<211> LENGTH: 19
<212> TYPE: RNA
<213> ORGANISM: Artificial Sequence
<220> FEATURE:
<223> OTHER INFORMATION: primer

<400> SEQUENCE: 138

```
ugcgaaauau gauguccug                                                19
```

<210> SEQ ID NO 139
<211> LENGTH: 23
<212> TYPE: DNA
<213> ORGANISM: Lygus hesperus

<400> SEQUENCE: 139

```
aaaaagcact agatgagccg aag                                           23
```

<210> SEQ ID NO 140
<211> LENGTH: 19
<212> TYPE: RNA
<213> ORGANISM: Artificial Sequence
<220> FEATURE:
<223> OTHER INFORMATION: primer

<400> SEQUENCE: 140

```
aaagcacuag augagccga                                                19
```

<210> SEQ ID NO 141
<211> LENGTH: 19
<212> TYPE: RNA
<213> ORGANISM: Artificial Sequence
<220> FEATURE:
<223> OTHER INFORMATION: primer

<400> SEQUENCE: 141

```
ucggcucauc uagugcuuu                                                19
```

<210> SEQ ID NO 142
<211> LENGTH: 23
<212> TYPE: DNA
<213> ORGANISM: Lygus hesperus

<400> SEQUENCE: 142
aagttcatcg gagagctttg caa                                          23

<210> SEQ ID NO 143
<211> LENGTH: 19
<212> TYPE: RNA
<213> ORGANISM: Artificial Sequence
<220> FEATURE:
<223> OTHER INFORMATION: primer

<400> SEQUENCE: 143
guucaucgga gagcuuugc                                               19

<210> SEQ ID NO 144
<211> LENGTH: 19
<212> TYPE: RNA
<213> ORGANISM: Artificial Sequence
<220> FEATURE:
<223> OTHER INFORMATION: primer

<400> SEQUENCE: 144
gcaaagcucu ccgaugaac                                               19

<210> SEQ ID NO 145
<211> LENGTH: 23
<212> TYPE: DNA
<213> ORGANISM: Lygus hesperus

<400> SEQUENCE: 145
aactttttga tcgtatggcg tcc                                          23

<210> SEQ ID NO 146
<211> LENGTH: 19
<212> TYPE: RNA
<213> ORGANISM: Artificial Sequence
<220> FEATURE:
<223> OTHER INFORMATION: primer

<400> SEQUENCE: 146
cuuuuugauc guauggcgu                                               19

<210> SEQ ID NO 147
<211> LENGTH: 19
<212> TYPE: RNA
<213> ORGANISM: Artificial Sequence
<220> FEATURE:
<223> OTHER INFORMATION: primer

<400> SEQUENCE: 147
acgccauacg aucaaaaag                                               19

<210> SEQ ID NO 148
<211> LENGTH: 23
<212> TYPE: DNA
<213> ORGANISM: Lygus hesperus
<220> FEATURE:
<221> NAME/KEY: misc_feature
<222> LOCATION: 10
<223> OTHER INFORMATION: n = A,T,C or G

<400> SEQUENCE: 148
aactttcctn ttccgcgttg ttg                                          23

<210> SEQ ID NO 149
<211> LENGTH: 19
<212> TYPE: RNA
<213> ORGANISM: Artificial Sequence -continued

```
<220> FEATURE:
<223> OTHER INFORMATION: primer
<220> FEATURE:
<221> NAME/KEY: misc_feature
<222> LOCATION: 8
<223> OTHER INFORMATION: n = A,T,C or G

<400> SEQUENCE: 149 cuuccunuu ccgcguugu                                                    19

<210> SEQ ID NO 150
<211> LENGTH: 16
<212> TYPE: RNA
<213> ORGANISM: Artificial Sequence
<220> FEATURE:
<223> OTHER INFORMATION: primer

<400> SEQUENCE: 150
acaacgcgga agaaag                                                      16

<210> SEQ ID NO 151
<211> LENGTH: 23
<212> TYPE: DNA
<213> ORGANISM: Lygus hesperus
<220> FEATURE:
<221> NAME/KEY: misc_feature
<222> LOCATION: 22
<223> OTHER INFORMATION: n = A,T,C or G

<400> SEQUENCE: 151
aagagaacgg agataacgag gna                                              23

<210> SEQ ID NO 152
<211> LENGTH: 19
<212> TYPE: RNA
<213> ORGANISM: Artificial Sequence
<220> FEATURE:
<223> OTHER INFORMATION: primer

<400> SEQUENCE: 152
gagaacggag auaacgagg                                                   19

<210> SEQ ID NO 153
<211> LENGTH: 19
<212> TYPE: RNA
<213> ORGANISM: Artificial Sequence
<220> FEATURE:
<223> OTHER INFORMATION: primer

<400> SEQUENCE: 153
ccucguuauc uccguucuc                                                   19

<210> SEQ ID NO 154
<211> LENGTH: 23
<212> TYPE: DNA
<213> ORGANISM: Lygus hesperus
<220> FEATURE:
<221> NAME/KEY: misc_feature
<222> LOCATION: 22
<223> OTHER INFORMATION: n = A,T,C or G

<400> SEQUENCE: 154
aaaaaggctc cgactgtttg gna                                              23

<210> SEQ ID NO 155
<211> LENGTH: 19
<212> TYPE: RNA
```

```
<213> ORGANISM: Artificial Sequence
<220> FEATURE:
<223> OTHER INFORMATION: primer

<400> SEQUENCE: 155
aaaggcuccg acuguuugg                                                  19

<210> SEQ ID NO 156
<211> LENGTH: 19
<212> TYPE: RNA
<213> ORGANISM: Artificial Sequence
<220> FEATURE:
<223> OTHER INFORMATION: primer

<400> SEQUENCE: 156
ccaaacaguc ggagccuuu                                                  19

<210> SEQ ID NO 157
<211> LENGTH: 23
<212> TYPE: DNA
<213> ORGANISM: Lygus hesperus

<400> SEQUENCE: 157
aaaaagctcc atacaggtga acg                                             23

<210> SEQ ID NO 158
<211> LENGTH: 19
<212> TYPE: RNA
<213> ORGANISM: Artificial Sequence
<220> FEATURE:
<223> OTHER INFORMATION: primer

<400> SEQUENCE: 158
aaagcuccau acaggugaa                                                  19

<210> SEQ ID NO 159
<211> LENGTH: 19
<212> TYPE: RNA
<213> ORGANISM: Artificial Sequence
<220> FEATURE:
<223> OTHER INFORMATION: primer

<400> SEQUENCE: 159
uucaccugua uggagcuuu                                                  19

<210> SEQ ID NO 160
<211> LENGTH: 23
<212> TYPE: DNA
<213> ORGANISM: Lygus hesperus

<400> SEQUENCE: 160
aaaaacaagc acaaagacgg gtc                                             23

<210> SEQ ID NO 161
<211> LENGTH: 19
<212> TYPE: RNA
<213> ORGANISM: Artificial Sequence
<220> FEATURE:
<223> OTHER INFORMATION: primer

<400> SEQUENCE: 161
aaacaagcac aaagacggg                                                  19

<210> SEQ ID NO 162
<211> LENGTH: 19
```

```
<212> TYPE: RNA
<213> ORGANISM: Artificial Sequence
<220> FEATURE:
<223> OTHER INFORMATION: primer

<400> SEQUENCE: 162
cccgucuuug ugcuuguuu                                                    19

<210> SEQ ID NO 163
<211> LENGTH: 23
<212> TYPE: DNA
<213> ORGANISM: Lygus hesperus

<400> SEQUENCE: 163
aagtatttca gtcttcctct gct                                               23

<210> SEQ ID NO 164
<211> LENGTH: 19
<212> TYPE: RNA
<213> ORGANISM: Artificial Sequence
<220> FEATURE:
<223> OTHER INFORMATION: primer

<400> SEQUENCE: 164
guauuucagu cuuccucug                                                    19

<210> SEQ ID NO 165
<211> LENGTH: 19
<212> TYPE: RNA
<213> ORGANISM: Artificial Sequence
<220> FEATURE:
<223> OTHER INFORMATION: primer

<400> SEQUENCE: 165
cagaggaaga cugaaauac                                                    19

<210> SEQ ID NO 166
<211> LENGTH: 23
<212> TYPE: DNA
<213> ORGANISM: Lygus hesperus

<400> SEQUENCE: 166
aagtcagaat gtcgactgaa aag                                               23

<210> SEQ ID NO 167
<211> LENGTH: 19
<212> TYPE: RNA
<213> ORGANISM: Artificial Sequence
<220> FEATURE:
<223> OTHER INFORMATION: primer

<400> SEQUENCE: 167
gucagaaugu cgacugaaa                                                    19

<210> SEQ ID NO 168
<211> LENGTH: 19
<212> TYPE: RNA
<213> ORGANISM: Artificial Sequence
<220> FEATURE:
<223> OTHER INFORMATION: primer

<400> SEQUENCE: 168
uuucagucga cauucugac                                                    19

<210> SEQ ID NO 169
```

```
<211> LENGTH: 23
<212> TYPE: DNA
<213> ORGANISM: Lygus hesperus

<400> SEQUENCE: 169
aaggaacgtg agatgatcct gta                                              23

<210> SEQ ID NO 170
<211> LENGTH: 19
<212> TYPE: RNA
<213> ORGANISM: Artificial Sequence
<220> FEATURE:
<223> OTHER INFORMATION: primer

<400> SEQUENCE: 170
ggaacgugag augauccug                                                   19

<210> SEQ ID NO 171
<211> LENGTH: 19
<212> TYPE: RNA
<213> ORGANISM: Artificial Sequence
<220> FEATURE:
<223> OTHER INFORMATION: primer

<400> SEQUENCE: 171
caggaucauc ucacguucc                                                   19

<210> SEQ ID NO 172
<211> LENGTH: 23
<212> TYPE: DNA
<213> ORGANISM: Lygus hesperus
<220> FEATURE:
<221> NAME/KEY: misc_feature
<222> LOCATION: 6
<223> OTHER INFORMATION: n = A,T,C or G

<400> SEQUENCE: 172
aacccnactt tcttgtacaa agt                                              23

<210> SEQ ID NO 173
<211> LENGTH: 19
<212> TYPE: RNA
<213> ORGANISM: Artificial Sequence
<220> FEATURE:
<223> OTHER INFORMATION: primer
<220> FEATURE:
<221> NAME/KEY: misc_feature
<222> LOCATION: 4
<223> OTHER INFORMATION: n = A,T,C or G

<400> SEQUENCE: 173
cccnacuuuc uuguacaaa                                                   19

<210> SEQ ID NO 174
<211> LENGTH: 16
<212> TYPE: RNA
<213> ORGANISM: Artificial Sequence
<220> FEATURE:
<223> OTHER INFORMATION: primer

<400> SEQUENCE: 174
uuuguacaag aaagug                                                      16

<210> SEQ ID NO 175
<211> LENGTH: 23
<212> TYPE: DNA
<213> ORGANISM: Lygus hesperus
```

```
<400> SEQUENCE: 175
aagtttttgc ggtgtcggaa tgt                                        23

<210> SEQ ID NO 176
<211> LENGTH: 19
<212> TYPE: RNA
<213> ORGANISM: Artificial Sequence
<220> FEATURE:
<223> OTHER INFORMATION: primer

<400> SEQUENCE: 176
guuuuugcgg ugucggaau                                             19

<210> SEQ ID NO 177
<211> LENGTH: 19
<212> TYPE: RNA
<213> ORGANISM: Artificial Sequence
<220> FEATURE:
<223> OTHER INFORMATION: primer

<400> SEQUENCE: 177
auuccgacac cgcaaaaac                                             19

<210> SEQ ID NO 178
<211> LENGTH: 23
<212> TYPE: DNA
<213> ORGANISM: Lygus hesperus
<220> FEATURE:
<221> NAME/KEY: misc_feature
<222> LOCATION: 5, 6, 7, 8
<223> OTHER INFORMATION: n = A,T,C or G

<400> SEQUENCE: 178
aaaannnntc cgaacgccgc caa                                        23

<210> SEQ ID NO 179
<211> LENGTH: 19
<212> TYPE: RNA
<213> ORGANISM: Artificial Sequence
<220> FEATURE:
<223> OTHER INFORMATION: primer
<220> FEATURE:
<221> NAME/KEY: misc_feature
<222> LOCATION: 3, 4, 5, 6
<223> OTHER INFORMATION: n = A,T,C or G

<400> SEQUENCE: 179
aannnnuccg aacgccgcc                                             19

<210> SEQ ID NO 180
<211> LENGTH: 15
<212> TYPE: RNA
<213> ORGANISM: Artificial Sequence
<220> FEATURE:
<223> OTHER INFORMATION: primer

<400> SEQUENCE: 180
ggcggcguuc ggauu                                                 15

<210> SEQ ID NO 181
<211> LENGTH: 23
<212> TYPE: DNA
<213> ORGANISM: Lygus hesperus

<400> SEQUENCE: 181
```
aaactcacct tctctcaagc cgt                                          23

<210> SEQ ID NO 182
<211> LENGTH: 19
<212> TYPE: RNA
<213> ORGANISM: Artificial Sequence
<220> FEATURE:
<223> OTHER INFORMATION: primer

<400> SEQUENCE: 182
acucaccuuc ucucaagcc                                               19

<210> SEQ ID NO 183
<211> LENGTH: 19
<212> TYPE: RNA
<213> ORGANISM: Artificial Sequence
<220> FEATURE:
<223> OTHER INFORMATION: primer

<400> SEQUENCE: 183
ggcuugagag aaggugagu                                               19

<210> SEQ ID NO 184
<211> LENGTH: 23
<212> TYPE: DNA
<213> ORGANISM: Lygus hesperus

<400> SEQUENCE: 184
aattcaacga gataaccgaa tga                                          23

<210> SEQ ID NO 185
<211> LENGTH: 19
<212> TYPE: RNA
<213> ORGANISM: Artificial Sequence
<220> FEATURE:
<223> OTHER INFORMATION: primer

<400> SEQUENCE: 185
uucaacgaga uaaccgaau                                               19

<210> SEQ ID NO 186
<211> LENGTH: 19
<212> TYPE: RNA
<213> ORGANISM: Artificial Sequence
<220> FEATURE:
<223> OTHER INFORMATION: primer

<400> SEQUENCE: 186
auucgguuau cucguugaa                                               19

<210> SEQ ID NO 187
<211> LENGTH: 23
<212> TYPE: DNA
<213> ORGANISM: Lygus hesperus

<400> SEQUENCE: 187
aagtctgtgt tgtctgaaag tag                                          23

<210> SEQ ID NO 188
<211> LENGTH: 19
<212> TYPE: RNA
<213> ORGANISM: Artificial Sequence
<220> FEATURE:
<223> OTHER INFORMATION: primer

<400> SEQUENCE: 188
gucuguguug ucugaaagu                                                19

<210> SEQ ID NO 189
<211> LENGTH: 19
<212> TYPE: RNA
<213> ORGANISM: Artificial Sequence
<220> FEATURE:
<223> OTHER INFORMATION: primer

<400> SEQUENCE: 189
acuuucagac aacacagac                                                19

<210> SEQ ID NO 190
<211> LENGTH: 23
<212> TYPE: DNA
<213> ORGANISM: Lygus hesperus

<400> SEQUENCE: 190
aactcccagt gtcgtcctca aga                                           23

<210> SEQ ID NO 191
<211> LENGTH: 19
<212> TYPE: RNA
<213> ORGANISM: Artificial Sequence
<220> FEATURE:
<223> OTHER INFORMATION: primer

<400> SEQUENCE: 191
cucccagugu cguccucaa                                                19

<210> SEQ ID NO 192
<211> LENGTH: 19
<212> TYPE: RNA
<213> ORGANISM: Artificial Sequence
<220> FEATURE:
<223> OTHER INFORMATION: primer

<400> SEQUENCE: 192
uugaggacga cacugggag                                                19

<210> SEQ ID NO 193
<211> LENGTH: 23
<212> TYPE: DNA
<213> ORGANISM: Lygus hesperus

<400> SEQUENCE: 193
aagttccatc caaagcaccg cag                                           23

<210> SEQ ID NO 194
<211> LENGTH: 19
<212> TYPE: RNA
<213> ORGANISM: Artificial Sequence
<220> FEATURE:
<223> OTHER INFORMATION: primer

<400> SEQUENCE: 194
guuccaucca aagcaccgc                                                19

<210> SEQ ID NO 195
<211> LENGTH: 19
<212> TYPE: RNA
<213> ORGANISM: Artificial Sequence
<220> FEATURE:
<223> OTHER INFORMATION: primer

```
<400> SEQUENCE: 195
gcggugcuuu ggauggaac                                                  19

<210> SEQ ID NO 196
<211> LENGTH: 23
<212> TYPE: DNA
<213> ORGANISM: Lygus hesperus

<400> SEQUENCE: 196
aaggaagtat cgcaccacat tct                                             23

<210> SEQ ID NO 197
<211> LENGTH: 19
<212> TYPE: RNA
<213> ORGANISM: Artificial Sequence
<220> FEATURE:
<223> OTHER INFORMATION: primer

<400> SEQUENCE: 197
ggaaguaucg caccacauu                                                  19

<210> SEQ ID NO 198
<211> LENGTH: 19
<212> TYPE: RNA
<213> ORGANISM: Artificial Sequence
<220> FEATURE:
<223> OTHER INFORMATION: primer

<400> SEQUENCE: 198
aauguggugc gauacuucc                                                  19

<210> SEQ ID NO 199
<211> LENGTH: 23
<212> TYPE: DNA
<213> ORGANISM: Lygus hesperus

<400> SEQUENCE: 199
aaatcaagga caatgtggta gct                                             23

<210> SEQ ID NO 200
<211> LENGTH: 19
<212> TYPE: RNA
<213> ORGANISM: Artificial Sequence
<220> FEATURE:
<223> OTHER INFORMATION: primer

<400> SEQUENCE: 200
aucaaggaca auggguag                                                   19

<210> SEQ ID NO 201
<211> LENGTH: 19
<212> TYPE: RNA
<213> ORGANISM: Artificial Sequence
<220> FEATURE:
<223> OTHER INFORMATION: primer

<400> SEQUENCE: 201
cuaccacauu guccuugau                                                  19

<210> SEQ ID NO 202
<211> LENGTH: 23
<212> TYPE: DNA
<213> ORGANISM: Lygus hesperus

<400> SEQUENCE: 202
```
aaagtgaagg tgaagattgc gag                                              23

<210> SEQ ID NO 203
<211> LENGTH: 19
<212> TYPE: RNA
<213> ORGANISM: Artificial Sequence
<220> FEATURE:
<223> OTHER INFORMATION: primer

<400> SEQUENCE: 203
agugaaggug aagauugcg                                                   19

<210> SEQ ID NO 204
<211> LENGTH: 19
<212> TYPE: RNA
<213> ORGANISM: Artificial Sequence
<220> FEATURE:
<223> OTHER INFORMATION: primer

<400> SEQUENCE: 204
cgcaaucuuc accuucacu                                                   19

<210> SEQ ID NO 205
<211> LENGTH: 23
<212> TYPE: DNA
<213> ORGANISM: Lygus hesperus

<400> SEQUENCE: 205
aagatgttgt gttaggttta ccg                                              23

<210> SEQ ID NO 206
<211> LENGTH: 19
<212> TYPE: RNA
<213> ORGANISM: Artificial Sequence
<220> FEATURE:
<223> OTHER INFORMATION: primer

<400> SEQUENCE: 206
gauguugugu uagguuuac                                                   19

<210> SEQ ID NO 207
<211> LENGTH: 19
<212> TYPE: RNA
<213> ORGANISM: Artificial Sequence
<220> FEATURE:
<223> OTHER INFORMATION: primer

<400> SEQUENCE: 207
guaaaccuaa cacaacauc                                                   19

<210> SEQ ID NO 208
<211> LENGTH: 23
<212> TYPE: DNA
<213> ORGANISM: Lygus hesperus

<400> SEQUENCE: 208
aacaaagtcg attccaccta gag                                              23

<210> SEQ ID NO 209
<211> LENGTH: 19
<212> TYPE: RNA
<213> ORGANISM: Artificial Sequence
<220> FEATURE:
<223> OTHER INFORMATION: primer

```
<400> SEQUENCE: 209
caaagucgau uccaccuag                                                    19

<210> SEQ ID NO 210
<211> LENGTH: 19
<212> TYPE: RNA
<213> ORGANISM: Artificial Sequence
<220> FEATURE:
<223> OTHER INFORMATION: primer

<400> SEQUENCE: 210
cuagguggaa ucgacuuug                                                    19

<210> SEQ ID NO 211
<211> LENGTH: 23
<212> TYPE: DNA
<213> ORGANISM: Lygus hesperus

<400> SEQUENCE: 211
aactttggtc ctggtttgga tag                                               23

<210> SEQ ID NO 212
<211> LENGTH: 19
<212> TYPE: RNA
<213> ORGANISM: Artificial Sequence
<220> FEATURE:
<223> OTHER INFORMATION: primer

<400> SEQUENCE: 212
cuuugguccu gguuuggau                                                    19

<210> SEQ ID NO 213
<211> LENGTH: 19
<212> TYPE: RNA
<213> ORGANISM: Artificial Sequence
<220> FEATURE:
<223> OTHER INFORMATION: primer

<400> SEQUENCE: 213
auccaaacca ggaccaaag                                                    19

<210> SEQ ID NO 214
<211> LENGTH: 23
<212> TYPE: DNA
<213> ORGANISM: Lygus hesperus
<220> FEATURE:
<221> NAME/KEY: misc_feature
<222> LOCATION: 19
<223> OTHER INFORMATION: n = A,T,C or G

<400> SEQUENCE: 214
aagctacagg aatccggana att                                               23

<210> SEQ ID NO 215
<211> LENGTH: 19
<212> TYPE: RNA
<213> ORGANISM: Artificial Sequence
<220> FEATURE:
<223> OTHER INFORMATION: primer
<220> FEATURE:
<221> NAME/KEY: misc_feature
<222> LOCATION: 17
<223> OTHER INFORMATION: n = A,T,C or G

<400> SEQUENCE: 215
gcuacaggaa uccgganaa                                                    19
```

<210> SEQ ID NO 216
<211> LENGTH: 18
<212> TYPE: RNA
<213> ORGANISM: Artificial Sequence
<220> FEATURE:
<223> OTHER INFORMATION: primer

<400> SEQUENCE: 216
uuuccggauu ccuguagc                                                    18

<210> SEQ ID NO 217
<211> LENGTH: 23
<212> TYPE: DNA
<213> ORGANISM: Lygus hesperus

<400> SEQUENCE: 217
aaggcgtgta atctctcaag caa                                              23

<210> SEQ ID NO 218
<211> LENGTH: 19
<212> TYPE: RNA
<213> ORGANISM: Artificial Sequence
<220> FEATURE:
<223> OTHER INFORMATION: primer

<400> SEQUENCE: 218
ggcguguaau cucucaagc                                                   19

<210> SEQ ID NO 219
<211> LENGTH: 19
<212> TYPE: RNA
<213> ORGANISM: Artificial Sequence
<220> FEATURE:
<223> OTHER INFORMATION: primer

<400> SEQUENCE: 219
gcuugagaga uuacacgcc                                                   19

<210> SEQ ID NO 220
<211> LENGTH: 23
<212> TYPE: DNA
<213> ORGANISM: Lygus hesperus

<400> SEQUENCE: 220
aattcgcggt caactttatc tct                                              23

<210> SEQ ID NO 221
<211> LENGTH: 19
<212> TYPE: RNA
<213> ORGANISM: Artificial Sequence
<220> FEATURE:
<223> OTHER INFORMATION: primer

<400> SEQUENCE: 221
uucgcgguca acuuuaucu                                                   19

<210> SEQ ID NO 222
<211> LENGTH: 19
<212> TYPE: RNA
<213> ORGANISM: Artificial Sequence
<220> FEATURE:
<223> OTHER INFORMATION: primer

<400> SEQUENCE: 222
agauaaaguu gaccgcgaa                              19

<210> SEQ ID NO 223
<211> LENGTH: 23
<212> TYPE: DNA
<213> ORGANISM: Lygus hesperus

<400> SEQUENCE: 223
aagaggtaca aatgtctttc ctg                         23

<210> SEQ ID NO 224
<211> LENGTH: 19
<212> TYPE: RNA
<213> ORGANISM: Artificial Sequence
<220> FEATURE:
<223> OTHER INFORMATION: primer

<400> SEQUENCE: 224
gagguacaaa ugucuuucc                              19

<210> SEQ ID NO 225
<211> LENGTH: 19
<212> TYPE: RNA
<213> ORGANISM: Artificial Sequence
<220> FEATURE:
<223> OTHER INFORMATION: primer

<400> SEQUENCE: 225
ggaaagacau uuguaccuc                              19

<210> SEQ ID NO 226
<211> LENGTH: 23
<212> TYPE: DNA
<213> ORGANISM: Lygus hesperus

<400> SEQUENCE: 226
aagtcagtcc tacacgtgtc ctc                         23

<210> SEQ ID NO 227
<211> LENGTH: 19
<212> TYPE: RNA
<213> ORGANISM: Artificial Sequence
<220> FEATURE:
<223> OTHER INFORMATION: primer

<400> SEQUENCE: 227
gucaguccua cacgugucc                              19

<210> SEQ ID NO 228
<211> LENGTH: 19
<212> TYPE: RNA
<213> ORGANISM: Artificial Sequence
<220> FEATURE:
<223> OTHER INFORMATION: primer

<400> SEQUENCE: 228
ggacacgugu aggacugac                              19

<210> SEQ ID NO 229
<211> LENGTH: 23
<212> TYPE: DNA
<213> ORGANISM: Lygus hesperus

<400> SEQUENCE: 229
aacaacgttc gccaggattt ttt                         23

-continued

<210> SEQ ID NO 230
<211> LENGTH: 19
<212> TYPE: RNA
<213> ORGANISM: Artificial Sequence
<220> FEATURE:
<223> OTHER INFORMATION: primer

<400> SEQUENCE: 230
caacguucgc caggauuuu                                                    19

<210> SEQ ID NO 231
<211> LENGTH: 19
<212> TYPE: RNA
<213> ORGANISM: Artificial Sequence
<220> FEATURE:
<223> OTHER INFORMATION: primer

<400> SEQUENCE: 231
aaaauccugg cgaacguug                                                    19

<210> SEQ ID NO 232
<211> LENGTH: 23
<212> TYPE: DNA
<213> ORGANISM: Lygus hesperus

<400> SEQUENCE: 232
aagactgctg acggaataac gaa                                               23

<210> SEQ ID NO 233
<211> LENGTH: 19
<212> TYPE: RNA
<213> ORGANISM: Artificial Sequence
<220> FEATURE:
<223> OTHER INFORMATION: primer

<400> SEQUENCE: 233
gacugcugac ggaauaacg                                                    19

<210> SEQ ID NO 234
<211> LENGTH: 19
<212> TYPE: RNA
<213> ORGANISM: Artificial Sequence
<220> FEATURE:
<223> OTHER INFORMATION: primer

<400> SEQUENCE: 234
cguuauuccg ucagcaguc                                                    19

<210> SEQ ID NO 235
<211> LENGTH: 23
<212> TYPE: DNA
<213> ORGANISM: Lygus hesperus

<400> SEQUENCE: 235
aaccccgacg gcaccgtcgc tga                                               23

<210> SEQ ID NO 236
<211> LENGTH: 19
<212> TYPE: RNA
<213> ORGANISM: Artificial Sequence
<220> FEATURE:
<223> OTHER INFORMATION: primer

<400> SEQUENCE: 236
ccccgacggc accgucgcu                                            19

<210> SEQ ID NO 237
<211> LENGTH: 19
<212> TYPE: RNA
<213> ORGANISM: Artificial Sequence
<220> FEATURE:
<223> OTHER INFORMATION: primer

<400> SEQUENCE: 237
agcgacggug ccgucgggg                                            19

<210> SEQ ID NO 238
<211> LENGTH: 23
<212> TYPE: DNA
<213> ORGANISM: Lygus hesperus

<400> SEQUENCE: 238
aagatctcca aagctcgtgg aat                                       23

<210> SEQ ID NO 239
<211> LENGTH: 19
<212> TYPE: RNA
<213> ORGANISM: Artificial Sequence
<220> FEATURE:
<223> OTHER INFORMATION: primer

<400> SEQUENCE: 239
gaucuccaaa gcucgugga                                            19

<210> SEQ ID NO 240
<211> LENGTH: 19
<212> TYPE: RNA
<213> ORGANISM: Artificial Sequence
<220> FEATURE:
<223> OTHER INFORMATION: primer

<400> SEQUENCE: 240
uccacgagcu uuggagauc                                            19

<210> SEQ ID NO 241
<211> LENGTH: 23
<212> TYPE: DNA
<213> ORGANISM: Lygus hesperus

<400> SEQUENCE: 241
aaattacccg cggaggatac tca                                       23

<210> SEQ ID NO 242
<211> LENGTH: 19
<212> TYPE: RNA
<213> ORGANISM: Artificial Sequence
<220> FEATURE:
<223> OTHER INFORMATION: primer

<400> SEQUENCE: 242
auuacccgcg gaggauacu                                            19

<210> SEQ ID NO 243
<211> LENGTH: 19
<212> TYPE: RNA
<213> ORGANISM: Artificial Sequence
<220> FEATURE:
<223> OTHER INFORMATION: primer

<400> SEQUENCE: 243
aguauccucc gcggguaau 19

<210> SEQ ID NO 244
<211> LENGTH: 23
<212> TYPE: DNA
<213> ORGANISM: Lygus hesperus

<400> SEQUENCE: 244
aattgtggct tcagctcccg tat 23

<210> SEQ ID NO 245
<211> LENGTH: 19
<212> TYPE: RNA
<213> ORGANISM: Artificial Sequence
<220> FEATURE:
<223> OTHER INFORMATION: primer

<400> SEQUENCE: 245
uuguggcuuc agcucccgu 19

<210> SEQ ID NO 246
<211> LENGTH: 19
<212> TYPE: RNA
<213> ORGANISM: Artificial Sequence
<220> FEATURE:
<223> OTHER INFORMATION: primer

<400> SEQUENCE: 246
acgggagcug aagccacaa 19

<210> SEQ ID NO 247
<211> LENGTH: 23
<212> TYPE: DNA
<213> ORGANISM: Lygus hesperus

<400> SEQUENCE: 247
aagtctttaa ggacggattt acg 23

<210> SEQ ID NO 248
<211> LENGTH: 19
<212> TYPE: RNA
<213> ORGANISM: Artificial Sequence
<220> FEATURE:
<223> OTHER INFORMATION: primer

<400> SEQUENCE: 248
gucuuuaagg acggauuua 19

<210> SEQ ID NO 249
<211> LENGTH: 19
<212> TYPE: RNA
<213> ORGANISM: Artificial Sequence
<220> FEATURE:
<223> OTHER INFORMATION: primer

<400> SEQUENCE: 249
uaaauccguc cuuaaagac 19

<210> SEQ ID NO 250
<211> LENGTH: 23
<212> TYPE: DNA
<213> ORGANISM: Lygus hesperus

<400> SEQUENCE: 250
aatgcgtgtt ggctcatctg tca                                          23

<210> SEQ ID NO 251
<211> LENGTH: 19
<212> TYPE: RNA
<213> ORGANISM: Artificial Sequence
<220> FEATURE:
<223> OTHER INFORMATION: primer

<400> SEQUENCE: 251
ugcguguugg cucaucugu                                               19

<210> SEQ ID NO 252
<211> LENGTH: 19
<212> TYPE: RNA
<213> ORGANISM: Artificial Sequence
<220> FEATURE:
<223> OTHER INFORMATION: primer

<400> SEQUENCE: 252
acagaugagc caacacgca                                               19

<210> SEQ ID NO 253
<211> LENGTH: 23
<212> TYPE: DNA
<213> ORGANISM: Lygus hesperus

<400> SEQUENCE: 253
aagctggtgg tcgtctgaag gat                                          23

<210> SEQ ID NO 254
<211> LENGTH: 19
<212> TYPE: RNA
<213> ORGANISM: Artificial Sequence
<220> FEATURE:
<223> OTHER INFORMATION: primer

<400> SEQUENCE: 254
gcuggugguc gucugaagg                                               19

<210> SEQ ID NO 255
<211> LENGTH: 19
<212> TYPE: RNA
<213> ORGANISM: Artificial Sequence
<220> FEATURE:
<223> OTHER INFORMATION: primer

<400> SEQUENCE: 255
ccuucagacg accaccagc                                               19

<210> SEQ ID NO 256
<211> LENGTH: 23
<212> TYPE: DNA
<213> ORGANISM: Lygus hesperus

<400> SEQUENCE: 256
aacactcgga tgaaatcact gtg                                          23

<210> SEQ ID NO 257
<211> LENGTH: 19
<212> TYPE: RNA
<213> ORGANISM: Artificial Sequence
<220> FEATURE:
<223> OTHER INFORMATION: primer

<400> SEQUENCE: 257
cacucggaug aaaucacug                                              19

<210> SEQ ID NO 258
<211> LENGTH: 19
<212> TYPE: RNA
<213> ORGANISM: Artificial Sequence
<220> FEATURE:
<223> OTHER INFORMATION: primer

<400> SEQUENCE: 258
cagugauuuc auccgagug                                              19

<210> SEQ ID NO 259
<211> LENGTH: 23
<212> TYPE: DNA
<213> ORGANISM: Lygus hesperus

<400> SEQUENCE: 259
aatcagtatc acgctcagga tgt                                         23

<210> SEQ ID NO 260
<211> LENGTH: 19
<212> TYPE: RNA
<213> ORGANISM: Artificial Sequence
<220> FEATURE:
<223> OTHER INFORMATION: primer

<400> SEQUENCE: 260
ucaguaucac gcucaggau                                              19

<210> SEQ ID NO 261
<211> LENGTH: 19
<212> TYPE: RNA
<213> ORGANISM: Artificial Sequence
<220> FEATURE:
<223> OTHER INFORMATION: primer

<400> SEQUENCE: 261
auccugagcg ugauacuga                                              19

<210> SEQ ID NO 262
<211> LENGTH: 23
<212> TYPE: DNA
<213> ORGANISM: Lygus hesperus

<400> SEQUENCE: 262
aacacccatg aagtcgctgt cgc                                         23

<210> SEQ ID NO 263
<211> LENGTH: 19
<212> TYPE: RNA
<213> ORGANISM: Artificial Sequence
<220> FEATURE:
<223> OTHER INFORMATION: primer

<400> SEQUENCE: 263
cacccaugaa gucgcuguc                                              19

<210> SEQ ID NO 264
<211> LENGTH: 19
<212> TYPE: RNA
<213> ORGANISM: Artificial Sequence
<220> FEATURE:
<223> OTHER INFORMATION: primer

```
<400> SEQUENCE: 264
gacagcgacu ucaugggug                                                  19

<210> SEQ ID NO 265
<211> LENGTH: 23
<212> TYPE: DNA
<213> ORGANISM: Lygus hesperus

<400> SEQUENCE: 265
aagatctcca aagctcgtgg aat                                             23

<210> SEQ ID NO 266
<211> LENGTH: 19
<212> TYPE: RNA
<213> ORGANISM: Artificial Sequence
<220> FEATURE:
<223> OTHER INFORMATION: primer

<400> SEQUENCE: 266
gaucuccaaa gcucgugga                                                  19

<210> SEQ ID NO 267
<211> LENGTH: 19
<212> TYPE: RNA
<213> ORGANISM: Artificial Sequence
<220> FEATURE:
<223> OTHER INFORMATION: primer

<400> SEQUENCE: 267
uccacgagcu uuggagauc                                                  19

<210> SEQ ID NO 268
<211> LENGTH: 23
<212> TYPE: DNA
<213> ORGANISM: Lygus hesperus

<400> SEQUENCE: 268
aactacaagt atcctgtgga ggg                                             23

<210> SEQ ID NO 269
<211> LENGTH: 19
<212> TYPE: RNA
<213> ORGANISM: Artificial Sequence
<220> FEATURE:
<223> OTHER INFORMATION: primer

<400> SEQUENCE: 269
cuacaaguau ccuguggag                                                  19

<210> SEQ ID NO 270
<211> LENGTH: 19
<212> TYPE: RNA
<213> ORGANISM: Artificial Sequence
<220> FEATURE:
<223> OTHER INFORMATION: primer

<400> SEQUENCE: 270
cuccacagga uacuuguag                                                  19

<210> SEQ ID NO 271
<211> LENGTH: 23
<212> TYPE: DNA
<213> ORGANISM: Lygus hesperus

<400> SEQUENCE: 271
```
aaattggagt gtgactggtg ctg                                                    23

<210> SEQ ID NO 272
<211> LENGTH: 19
<212> TYPE: RNA
<213> ORGANISM: Artificial Sequence
<220> FEATURE:
<223> OTHER INFORMATION: primer

<400> SEQUENCE: 272
auuggagugu gacuggugc                                                         19

<210> SEQ ID NO 273
<211> LENGTH: 19
<212> TYPE: RNA
<213> ORGANISM: Artificial Sequence
<220> FEATURE:
<223> OTHER INFORMATION: primer

<400> SEQUENCE: 273
gcaccaguca cacuccaau                                                         19

<210> SEQ ID NO 274
<211> LENGTH: 23
<212> TYPE: DNA
<213> ORGANISM: Lygus hesperus

<400> SEQUENCE: 274
aacatcagac gccctctact gga                                                    23

<210> SEQ ID NO 275
<211> LENGTH: 19
<212> TYPE: RNA
<213> ORGANISM: Artificial Sequence
<220> FEATURE:
<223> OTHER INFORMATION: primer

<400> SEQUENCE: 275
caucagacgc ccucuacug                                                         19

<210> SEQ ID NO 276
<211> LENGTH: 19
<212> TYPE: RNA
<213> ORGANISM: Artificial Sequence
<220> FEATURE:
<223> OTHER INFORMATION: primer

<400> SEQUENCE: 276
caguagaggg cgucugaug                                                         19

<210> SEQ ID NO 277
<211> LENGTH: 23
<212> TYPE: DNA
<213> ORGANISM: Lygus hesperus

<400> SEQUENCE: 277
aaacggttct ttccgaaacg acg                                                    23

<210> SEQ ID NO 278
<211> LENGTH: 19
<212> TYPE: RNA
<213> ORGANISM: Artificial Sequence
<220> FEATURE:
<223> OTHER INFORMATION: primer

```
<400> SEQUENCE: 278 acguucuuu ccgaaacga                                                    19

<210> SEQ ID NO 279
<211> LENGTH: 19
<212> TYPE: RNA
<213> ORGANISM: Artificial Sequence
<220> FEATURE:
<223> OTHER INFORMATION: primer

<400> SEQUENCE: 279
ucguuucgga aagaaccgu                                                   19

<210> SEQ ID NO 280
<211> LENGTH: 23
<212> TYPE: DNA
<213> ORGANISM: Lygus hesperus

<400> SEQUENCE: 280
aaccatcgtt cctggtgatg cat                                              23

<210> SEQ ID NO 281
<211> LENGTH: 19
<212> TYPE: RNA
<213> ORGANISM: Artificial Sequence
<220> FEATURE:
<223> OTHER INFORMATION: primer

<400> SEQUENCE: 281
ccaucguucc uggugaugc                                                   19

<210> SEQ ID NO 282
<211> LENGTH: 19
<212> TYPE: RNA
<213> ORGANISM: Artificial Sequence
<220> FEATURE:
<223> OTHER INFORMATION: primer

<400> SEQUENCE: 282
gcaucaccag gaacgaugg                                                   19

<210> SEQ ID NO 283
<211> LENGTH: 23
<212> TYPE: DNA
<213> ORGANISM: Lygus hesperus

<400> SEQUENCE: 283
aaagtcttca gagaggaagc tgc                                              23

<210> SEQ ID NO 284
<211> LENGTH: 19
<212> TYPE: RNA
<213> ORGANISM: Artificial Sequence
<220> FEATURE:
<223> OTHER INFORMATION: primer

<400> SEQUENCE: 284
agucuucaga gaggaagcu                                                   19

<210> SEQ ID NO 285
<211> LENGTH: 19
<212> TYPE: RNA
<213> ORGANISM: Artificial Sequence
<220> FEATURE:
<223> OTHER INFORMATION: primer
```

```
<400> SEQUENCE: 285
agcuuccucu cugaagacu                                                    19

<210> SEQ ID NO 286
<211> LENGTH: 23
<212> TYPE: DNA
<213> ORGANISM: Lygus hesperus

<400> SEQUENCE: 286
aagatgttcc atggagaggc aca                                               23

<210> SEQ ID NO 287
<211> LENGTH: 19
<212> TYPE: RNA
<213> ORGANISM: Artificial Sequence
<220> FEATURE:
<223> OTHER INFORMATION: primer

<400> SEQUENCE: 287
gauguuccau ggagaggca                                                    19

<210> SEQ ID NO 288
<211> LENGTH: 19
<212> TYPE: RNA
<213> ORGANISM: Artificial Sequence
<220> FEATURE:
<223> OTHER INFORMATION: primer

<400> SEQUENCE: 288
ugccucucca uggaacauc                                                    19

<210> SEQ ID NO 289
<211> LENGTH: 23
<212> TYPE: DNA
<213> ORGANISM: Lygus hesperus

<400> SEQUENCE: 289
aaatagggca acttcacgga tta                                               23

<210> SEQ ID NO 290
<211> LENGTH: 19
<212> TYPE: RNA
<213> ORGANISM: Artificial Sequence
<220> FEATURE:
<223> OTHER INFORMATION: primer

<400> SEQUENCE: 290
auagggcaac uucacggau                                                    19

<210> SEQ ID NO 291
<211> LENGTH: 19
<212> TYPE: RNA
<213> ORGANISM: Artificial Sequence
<220> FEATURE:
<223> OTHER INFORMATION: primer

<400> SEQUENCE: 291
auccgugaag uugcccuau                                                    19

<210> SEQ ID NO 292
<211> LENGTH: 23
<212> TYPE: DNA
<213> ORGANISM: Lygus hesperus
```

```
<400> SEQUENCE: 292
aagaaccatt cgccgttatc acc                                              23

<210> SEQ ID NO 293
<211> LENGTH: 19
<212> TYPE: RNA
<213> ORGANISM: Artificial Sequence
<220> FEATURE:
<223> OTHER INFORMATION: primer

<400> SEQUENCE: 293
gaaccauucg ccguuauca                                                   19

<210> SEQ ID NO 294
<211> LENGTH: 19
<212> TYPE: RNA
<213> ORGANISM: Artificial Sequence
<220> FEATURE:
<223> OTHER INFORMATION: primer

<400> SEQUENCE: 294
ugauaacggc gaaugguuc                                                   19

<210> SEQ ID NO 295
<211> LENGTH: 23
<212> TYPE: DNA
<213> ORGANISM: Lygus hesperus

<400> SEQUENCE: 295
aagctgcact gggattcatt cct                                              23

<210> SEQ ID NO 296
<211> LENGTH: 19
<212> TYPE: RNA
<213> ORGANISM: Artificial Sequence
<220> FEATURE:
<223> OTHER INFORMATION: primer

<400> SEQUENCE: 296
gcugcacugg gauucauuc                                                   19

<210> SEQ ID NO 297
<211> LENGTH: 19
<212> TYPE: RNA
<213> ORGANISM: Artificial Sequence
<220> FEATURE:
<223> OTHER INFORMATION: primer

<400> SEQUENCE: 297
gaaugaaucc cagugcagc                                                   19

<210> SEQ ID NO 298
<211> LENGTH: 23
<212> TYPE: DNA
<213> ORGANISM: Lygus hesperus

<400> SEQUENCE: 298
aatacaaaag tcgcgtcttc cgg                                              23

<210> SEQ ID NO 299
<211> LENGTH: 19
<212> TYPE: RNA
<213> ORGANISM: Artificial Sequence
<220> FEATURE:
<223> OTHER INFORMATION: primer
```

-continued

```
<400> SEQUENCE: 299
uacaaaaguc gcgucuucc                                          19

<210> SEQ ID NO 300
<211> LENGTH: 19
<212> TYPE: RNA
<213> ORGANISM: Artificial Sequence
<220> FEATURE:
<223> OTHER INFORMATION: primer

<400> SEQUENCE: 300
ggaagacgcg acuuugua                                           19

<210> SEQ ID NO 301
<211> LENGTH: 23
<212> TYPE: DNA
<213> ORGANISM: Lygus hesperus

<400> SEQUENCE: 301
aagatctttc gactcttgac gtg                                     23

<210> SEQ ID NO 302
<211> LENGTH: 19
<212> TYPE: RNA
<213> ORGANISM: Artificial Sequence
<220> FEATURE:
<223> OTHER INFORMATION: primer

<400> SEQUENCE: 302
gaucuuucga cucuugacg                                          19

<210> SEQ ID NO 303
<211> LENGTH: 19
<212> TYPE: RNA
<213> ORGANISM: Artificial Sequence
<220> FEATURE:
<223> OTHER INFORMATION: primer

<400> SEQUENCE: 303
cgucaagagu cgaaagauc                                          19

<210> SEQ ID NO 304
<211> LENGTH: 23
<212> TYPE: DNA
<213> ORGANISM: Lygus hesperus

<400> SEQUENCE: 304
aatatcggta ctattggtca cgt                                     23

<210> SEQ ID NO 305
<211> LENGTH: 19
<212> TYPE: RNA
<213> ORGANISM: Artificial Sequence
<220> FEATURE:
<223> OTHER INFORMATION: primer

<400> SEQUENCE: 305
uaucgguacu auuggucac                                          19

<210> SEQ ID NO 306
<211> LENGTH: 19
<212> TYPE: RNA
<213> ORGANISM: Artificial Sequence
<220> FEATURE:
```

```
<223> OTHER INFORMATION: primer

<400> SEQUENCE: 306
gugaccaaua guaccgaua                                                    19

<210> SEQ ID NO 307
<211> LENGTH: 23
<212> TYPE: DNA
<213> ORGANISM: Lygus hesperus

<400> SEQUENCE: 307
aatttcgacg tggaagtgtt aag                                               23

<210> SEQ ID NO 308
<211> LENGTH: 19
<212> TYPE: RNA
<213> ORGANISM: Artificial Sequence
<220> FEATURE:
<223> OTHER INFORMATION: primer

<400> SEQUENCE: 308
uuucgacgug aaguguua                                                     19

<210> SEQ ID NO 309
<211> LENGTH: 19
<212> TYPE: RNA
<213> ORGANISM: Artificial Sequence
<220> FEATURE:
<223> OTHER INFORMATION: primer

<400> SEQUENCE: 309
uaacacuucc acgucgaaa                                                    19

<210> SEQ ID NO 310
<211> LENGTH: 23
<212> TYPE: DNA
<213> ORGANISM: Lygus hesperus

<400> SEQUENCE: 310
aatgttgcat ctcgaaggtg caa                                               23

<210> SEQ ID NO 311
<211> LENGTH: 19
<212> TYPE: RNA
<213> ORGANISM: Artificial Sequence
<220> FEATURE:
<223> OTHER INFORMATION: primer

<400> SEQUENCE: 311
uguugcaucu cgaaggugc                                                    19

<210> SEQ ID NO 312
<211> LENGTH: 19
<212> TYPE: RNA
<213> ORGANISM: Artificial Sequence
<220> FEATURE:
<223> OTHER INFORMATION: primer

<400> SEQUENCE: 312
gcaccuucga gaugcaaca                                                    19

<210> SEQ ID NO 313
<211> LENGTH: 23
<212> TYPE: DNA
<213> ORGANISM: Lygus hesperus
```

-continued

```
<400> SEQUENCE: 313
aacactgggt aaagatgtag gac                                              23

<210> SEQ ID NO 314
<211> LENGTH: 19
<212> TYPE: RNA
<213> ORGANISM: Artificial Sequence
<220> FEATURE:
<223> OTHER INFORMATION: primer

<400> SEQUENCE: 314
cacuggguaa agauguagg                                                   19

<210> SEQ ID NO 315
<211> LENGTH: 19
<212> TYPE: RNA
<213> ORGANISM: Artificial Sequence
<220> FEATURE:
<223> OTHER INFORMATION: primer

<400> SEQUENCE: 315
ccuacaucuu uacccagug                                                   19

<210> SEQ ID NO 316
<211> LENGTH: 23
<212> TYPE: DNA
<213> ORGANISM: Lygus hesperus

<400> SEQUENCE: 316
aacccgggtc ttttctgtaa aga                                              23

<210> SEQ ID NO 317
<211> LENGTH: 19
<212> TYPE: RNA
<213> ORGANISM: Artificial Sequence
<220> FEATURE:
<223> OTHER INFORMATION: primer

<400> SEQUENCE: 317
cccgggucuu uucuguaaa                                                   19

<210> SEQ ID NO 318
<211> LENGTH: 19
<212> TYPE: RNA
<213> ORGANISM: Artificial Sequence
<220> FEATURE:
<223> OTHER INFORMATION: primer

<400> SEQUENCE: 318
uuuacagaaa agacccggg                                                   19

<210> SEQ ID NO 319
<211> LENGTH: 23
<212> TYPE: DNA
<213> ORGANISM: Lygus hesperus

<400> SEQUENCE: 319
aaacctcgaa accaaaaacg tag                                              23

<210> SEQ ID NO 320
<211> LENGTH: 19
<212> TYPE: RNA
<213> ORGANISM: Artificial Sequence
<220> FEATURE:
```

```
<223> OTHER INFORMATION: primer

<400> SEQUENCE: 320
accucgaaac caaaaacgu                                                    19

<210> SEQ ID NO 321
<211> LENGTH: 19
<212> TYPE: RNA
<213> ORGANISM: Artificial Sequence
<220> FEATURE:
<223> OTHER INFORMATION: primer

<400> SEQUENCE: 321
acguuuuugg uuucgaggu                                                    19

<210> SEQ ID NO 322
<211> LENGTH: 23
<212> TYPE: DNA
<213> ORGANISM: Lygus hesperus

<400> SEQUENCE: 322
aagttggaaa ctggagtcca gat                                               23

<210> SEQ ID NO 323
<211> LENGTH: 19
<212> TYPE: RNA
<213> ORGANISM: Artificial Sequence
<220> FEATURE:
<223> OTHER INFORMATION: primer

<400> SEQUENCE: 323
guuggaaacu ggaguccag                                                    19

<210> SEQ ID NO 324
<211> LENGTH: 19
<212> TYPE: RNA
<213> ORGANISM: Artificial Sequence
<220> FEATURE:
<223> OTHER INFORMATION: primer

<400> SEQUENCE: 324
cuggacucca guuccaac                                                     19

<210> SEQ ID NO 325
<211> LENGTH: 23
<212> TYPE: DNA
<213> ORGANISM: Lygus hesperus

<400> SEQUENCE: 325
aaatcttctt cgggactatc cat                                               23

<210> SEQ ID NO 326
<211> LENGTH: 19
<212> TYPE: RNA
<213> ORGANISM: Artificial Sequence
<220> FEATURE:
<223> OTHER INFORMATION: primer

<400> SEQUENCE: 326
aucuucuucg ggacuaucc                                                    19

<210> SEQ ID NO 327
<211> LENGTH: 19
<212> TYPE: RNA
<213> ORGANISM: Artificial Sequence
```

```
<220> FEATURE:
<223> OTHER INFORMATION: primer

<400> SEQUENCE: 327
ggauaguccc gaagaagau                                              19

<210> SEQ ID NO 328
<211> LENGTH: 23
<212> TYPE: DNA
<213> ORGANISM: Lygus hesperus

<400> SEQUENCE: 328
aaaaccagaa cagaaaccgg agt                                         23

<210> SEQ ID NO 329
<211> LENGTH: 19
<212> TYPE: RNA
<213> ORGANISM: Artificial Sequence
<220> FEATURE:
<223> OTHER INFORMATION: primer

<400> SEQUENCE: 329
aaccagaaca gaaaccgga                                              19

<210> SEQ ID NO 330
<211> LENGTH: 19
<212> TYPE: RNA
<213> ORGANISM: Artificial Sequence
<220> FEATURE:
<223> OTHER INFORMATION: primer

<400> SEQUENCE: 330
uccgguuucu guucugguu                                              19

<210> SEQ ID NO 331
<211> LENGTH: 23
<212> TYPE: DNA
<213> ORGANISM: Lygus hesperus

<400> SEQUENCE: 331
aagtgatgac cttctctttg gga                                         23

<210> SEQ ID NO 332
<211> LENGTH: 19
<212> TYPE: RNA
<213> ORGANISM: Artificial Sequence
<220> FEATURE:
<223> OTHER INFORMATION: primer

<400> SEQUENCE: 332
gugaugaccu ucucuuugg                                              19

<210> SEQ ID NO 333
<211> LENGTH: 19
<212> TYPE: RNA
<213> ORGANISM: Artificial Sequence
<220> FEATURE:
<223> OTHER INFORMATION: primer

<400> SEQUENCE: 333
ccaaagagaa ggucaucac                                              19

<210> SEQ ID NO 334
<211> LENGTH: 23
<212> TYPE: DNA
```

<213> ORGANISM: Lygus hesperus

<400> SEQUENCE: 334
aacaggacat catatttcgc agg                                    23

<210> SEQ ID NO 335
<211> LENGTH: 19
<212> TYPE: RNA
<213> ORGANISM: Artificial Sequence
<220> FEATURE:
<223> OTHER INFORMATION: primer

<400> SEQUENCE: 335
caggacauca uauuucgca                                         19

<210> SEQ ID NO 336
<211> LENGTH: 19
<212> TYPE: RNA
<213> ORGANISM: Artificial Sequence
<220> FEATURE:
<223> OTHER INFORMATION: primer

<400> SEQUENCE: 336
ugcgaaauau gauguccug                                         19

<210> SEQ ID NO 337
<211> LENGTH: 23
<212> TYPE: DNA
<213> ORGANISM: Lygus hesperus

<400> SEQUENCE: 337
aaaaagcact agatgagccg aag                                    23

<210> SEQ ID NO 338
<211> LENGTH: 19
<212> TYPE: RNA
<213> ORGANISM: Artificial Sequence
<220> FEATURE:
<223> OTHER INFORMATION: primer

<400> SEQUENCE: 338
aaagcacuag augagccga                                         19

<210> SEQ ID NO 339
<211> LENGTH: 19
<212> TYPE: RNA
<213> ORGANISM: Artificial Sequence
<220> FEATURE:
<223> OTHER INFORMATION: primer

<400> SEQUENCE: 339
ucggcucauc uagugcuuu                                         19

<210> SEQ ID NO 340
<211> LENGTH: 23
<212> TYPE: DNA
<213> ORGANISM: Lygus hesperus

<400> SEQUENCE: 340
aagttcatcg gagagctttg caa                                    23

<210> SEQ ID NO 341
<211> LENGTH: 19
<212> TYPE: RNA
<213> ORGANISM: Artificial Sequence

```
<220> FEATURE:
<223> OTHER INFORMATION: primer

<400> SEQUENCE: 341
guucaucgga gagcuuugc                                                    19

<210> SEQ ID NO 342
<211> LENGTH: 19
<212> TYPE: RNA
<213> ORGANISM: Artificial Sequence
<220> FEATURE:
<223> OTHER INFORMATION: primer

<400> SEQUENCE: 342
gcaaagcucu ccgaugaac                                                    19

<210> SEQ ID NO 343
<211> LENGTH: 23
<212> TYPE: DNA
<213> ORGANISM: Lygus hesperus

<400> SEQUENCE: 343 aacttttga tcgtatggcg tcc                                                23

<210> SEQ ID NO 344
<211> LENGTH: 19
<212> TYPE: RNA
<213> ORGANISM: Artificial Sequence
<220> FEATURE:
<223> OTHER INFORMATION: primer

<400> SEQUENCE: 344
cuuuuugauc guauggcgu                                                    19

<210> SEQ ID NO 345
<211> LENGTH: 19
<212> TYPE: RNA
<213> ORGANISM: Artificial Sequence
<220> FEATURE:
<223> OTHER INFORMATION: primer

<400> SEQUENCE: 345
acgccauacg aucaaaaag                                                    19

<210> SEQ ID NO 346
<211> LENGTH: 23
<212> TYPE: DNA
<213> ORGANISM: Lygus hesperus
<220> FEATURE:
<221> NAME/KEY: misc_feature
<222> LOCATION: 22
<223> OTHER INFORMATION: n = A,T,C or G

<400> SEQUENCE: 346
aagagaacgg agataacgag gna                                               23

<210> SEQ ID NO 347
<211> LENGTH: 19
<212> TYPE: RNA
<213> ORGANISM: Artificial Sequence
<220> FEATURE:
<223> OTHER INFORMATION: primer

<400> SEQUENCE: 347
gagaacggag auaacgagg                                                    19
```

```
<210> SEQ ID NO 348
<211> LENGTH: 19
<212> TYPE: RNA
<213> ORGANISM: Artificial Sequence
<220> FEATURE:
<223> OTHER INFORMATION: primer

<400> SEQUENCE: 348
ccucguuauc uccguucuc                                                  19

<210> SEQ ID NO 349
<211> LENGTH: 23
<212> TYPE: DNA
<213> ORGANISM: Lygus hesperus
<220> FEATURE:
<221> NAME/KEY: misc_feature
<222> LOCATION: 22
<223> OTHER INFORMATION: n = A,T,C or G

<400> SEQUENCE: 349
aaaaaggctc cgactgtttg gna                                             23

<210> SEQ ID NO 350
<211> LENGTH: 19
<212> TYPE: RNA
<213> ORGANISM: Artificial Sequence
<220> FEATURE:
<223> OTHER INFORMATION: primer

<400> SEQUENCE: 350
aaaggcuccg acuguuugg                                                  19

<210> SEQ ID NO 351
<211> LENGTH: 19
<212> TYPE: RNA
<213> ORGANISM: Artificial Sequence
<220> FEATURE:
<223> OTHER INFORMATION: primer

<400> SEQUENCE: 351
ccaaacaguc ggagccuuu                                                  19

<210> SEQ ID NO 352
<211> LENGTH: 23
<212> TYPE: DNA
<213> ORGANISM: Lygus hesperus

<400> SEQUENCE: 352
aaaaagctcc atacaggtga acg                                             23

<210> SEQ ID NO 353
<211> LENGTH: 19
<212> TYPE: RNA
<213> ORGANISM: Artificial Sequence
<220> FEATURE:
<223> OTHER INFORMATION: primer

<400> SEQUENCE: 353
aaagcuccau acaggugaa                                                  19

<210> SEQ ID NO 354
<211> LENGTH: 19
<212> TYPE: RNA
<213> ORGANISM: Artificial Sequence
<220> FEATURE:
<223> OTHER INFORMATION: primer
```

```
<400> SEQUENCE: 354
uucaccugua uggagcuuu                                                    19

<210> SEQ ID NO 355
<211> LENGTH: 23
<212> TYPE: DNA
<213> ORGANISM: Lygus hesperus

<400> SEQUENCE: 355
aaaaacaagc acaaagacgg gtc                                               23

<210> SEQ ID NO 356
<211> LENGTH: 19
<212> TYPE: RNA
<213> ORGANISM: Artificial Sequence
<220> FEATURE:
<223> OTHER INFORMATION: primer

<400> SEQUENCE: 356
aaacaagcac aaagacggg                                                    19

<210> SEQ ID NO 357
<211> LENGTH: 19
<212> TYPE: RNA
<213> ORGANISM: Artificial Sequence
<220> FEATURE:
<223> OTHER INFORMATION: primer

<400> SEQUENCE: 357
cccgucuuug ugcuuguuu                                                    19

<210> SEQ ID NO 358
<211> LENGTH: 23
<212> TYPE: DNA
<213> ORGANISM: Lygus hesperus

<400> SEQUENCE: 358
aagtatttca gtcttcctct gct                                               23

<210> SEQ ID NO 359
<211> LENGTH: 19
<212> TYPE: RNA
<213> ORGANISM: Artificial Sequence
<220> FEATURE:
<223> OTHER INFORMATION: primer

<400> SEQUENCE: 359
guauuucagu cuuccucug                                                    19

<210> SEQ ID NO 360
<211> LENGTH: 19
<212> TYPE: RNA
<213> ORGANISM: Artificial Sequence
<220> FEATURE:
<223> OTHER INFORMATION: primer

<400> SEQUENCE: 360
cagaggaaga cugaaauac                                                    19

<210> SEQ ID NO 361
<211> LENGTH: 23
<212> TYPE: DNA
<213> ORGANISM: Lygus hesperus
```

<400> SEQUENCE: 361
aagtcagaat gtcgactgaa aag                                   23

<210> SEQ ID NO 362
<211> LENGTH: 19
<212> TYPE: RNA
<213> ORGANISM: Artificial Sequence
<220> FEATURE:
<223> OTHER INFORMATION: primer

<400> SEQUENCE: 362
gucagaaugu cgacugaaa                                        19

<210> SEQ ID NO 363
<211> LENGTH: 19
<212> TYPE: RNA
<213> ORGANISM: Artificial Sequence
<220> FEATURE:
<223> OTHER INFORMATION: primer

<400> SEQUENCE: 363
uuucagucga cauucugac                                        19

<210> SEQ ID NO 364
<211> LENGTH: 23
<212> TYPE: DNA
<213> ORGANISM: Lygus hesperus

<400> SEQUENCE: 364
aaggaacgtg agatgatcct gta                                   23

<210> SEQ ID NO 365
<211> LENGTH: 19
<212> TYPE: RNA
<213> ORGANISM: Artificial Sequence
<220> FEATURE:
<223> OTHER INFORMATION: primer

<400> SEQUENCE: 365
ggaacgugag augauccug                                        19

<210> SEQ ID NO 366
<211> LENGTH: 19
<212> TYPE: RNA
<213> ORGANISM: Artificial Sequence
<220> FEATURE:
<223> OTHER INFORMATION: primer

<400> SEQUENCE: 366
caggaucauc ucacguucc                                        19

<210> SEQ ID NO 367
<211> LENGTH: 23
<212> TYPE: DNA
<213> ORGANISM: Lygus hesperus

<400> SEQUENCE: 367 aagttttgc ggtgtcggaa tgt                                    23

<210> SEQ ID NO 368
<211> LENGTH: 19
<212> TYPE: RNA
<213> ORGANISM: Artificial Sequence
<220> FEATURE:
<223> OTHER INFORMATION: primer -continued

<400> SEQUENCE: 368
guuuuugcgg ugucggaau                                              19

<210> SEQ ID NO 369
<211> LENGTH: 19
<212> TYPE: RNA
<213> ORGANISM: Artificial Sequence
<220> FEATURE:
<223> OTHER INFORMATION: primer

<400> SEQUENCE: 369
auuccgacac cgcaaaaac                                              19

<210> SEQ ID NO 370
<211> LENGTH: 23
<212> TYPE: DNA
<213> ORGANISM: Lygus hesperus

<400> SEQUENCE: 370
aaactcacct tctctcaagc cgt                                         23

<210> SEQ ID NO 371
<211> LENGTH: 19
<212> TYPE: RNA
<213> ORGANISM: Artificial Sequence
<220> FEATURE:
<223> OTHER INFORMATION: primer

<400> SEQUENCE: 371
acucaccuuc ucucaagcc                                              19

<210> SEQ ID NO 372
<211> LENGTH: 19
<212> TYPE: RNA
<213> ORGANISM: Artificial Sequence
<220> FEATURE:
<223> OTHER INFORMATION: primer

<400> SEQUENCE: 372
ggcuugagag aaggugagu                                              19

<210> SEQ ID NO 373
<211> LENGTH: 23
<212> TYPE: DNA
<213> ORGANISM: Lygus hesperus

<400> SEQUENCE: 373
aattcaacga gataaccgaa tga                                         23

<210> SEQ ID NO 374
<211> LENGTH: 19
<212> TYPE: RNA
<213> ORGANISM: Artificial Sequence
<220> FEATURE:
<223> OTHER INFORMATION: primer

<400> SEQUENCE: 374
uucaacgaga uaaccgaau                                              19

<210> SEQ ID NO 375
<211> LENGTH: 19
<212> TYPE: RNA
<213> ORGANISM: Artificial Sequence
<220> FEATURE:

<223> OTHER INFORMATION: primer

<400> SEQUENCE: 375
auucgguuau cucguugaa                                          19

<210> SEQ ID NO 376
<211> LENGTH: 23
<212> TYPE: DNA
<213> ORGANISM: Lygus hesperus

<400> SEQUENCE: 376
aagtctgtgt tgtctgaaag tag                                     23

<210> SEQ ID NO 377
<211> LENGTH: 19
<212> TYPE: RNA
<213> ORGANISM: Artificial Sequence
<220> FEATURE:
<223> OTHER INFORMATION: primer

<400> SEQUENCE: 377
gucuguguug ucugaaagu                                          19

<210> SEQ ID NO 378
<211> LENGTH: 19
<212> TYPE: RNA
<213> ORGANISM: Artificial Sequence
<220> FEATURE:
<223> OTHER INFORMATION: primer

<400> SEQUENCE: 378 acuucagac aacacagac                                           19

<210> SEQ ID NO 379
<211> LENGTH: 23
<212> TYPE: DNA
<213> ORGANISM: Lygus hesperus

<400> SEQUENCE: 379
aactcccagt gtcgtcctca aga                                     23

<210> SEQ ID NO 380
<211> LENGTH: 19
<212> TYPE: RNA
<213> ORGANISM: Artificial Sequence
<220> FEATURE:
<223> OTHER INFORMATION: primer

<400> SEQUENCE: 380
cucccagugu cguccucaa                                          19

<210> SEQ ID NO 381
<211> LENGTH: 19
<212> TYPE: RNA
<213> ORGANISM: Artificial Sequence
<220> FEATURE:
<223> OTHER INFORMATION: primer

<400> SEQUENCE: 381
uugaggacga cacugggag                                          19

<210> SEQ ID NO 382
<211> LENGTH: 23
<212> TYPE: DNA
<213> ORGANISM: Lygus hesperus

<400> SEQUENCE: 382
aagttccatc caaagcaccg cag                                          23

<210> SEQ ID NO 383
<211> LENGTH: 19
<212> TYPE: RNA
<213> ORGANISM: Artificial Sequence
<220> FEATURE:
<223> OTHER INFORMATION: primer

<400> SEQUENCE: 383
guuccaucca aagcaccgc                                               19

<210> SEQ ID NO 384
<211> LENGTH: 19
<212> TYPE: RNA
<213> ORGANISM: Artificial Sequence
<220> FEATURE:
<223> OTHER INFORMATION: primer

<400> SEQUENCE: 384
gcggugcuuu ggauggaac                                               19

<210> SEQ ID NO 385
<211> LENGTH: 23
<212> TYPE: DNA
<213> ORGANISM: Lygus hesperus

<400> SEQUENCE: 385
aaggaagtat cgcaccacat tct                                          23

<210> SEQ ID NO 386
<211> LENGTH: 19
<212> TYPE: RNA
<213> ORGANISM: Artificial Sequence
<220> FEATURE:
<223> OTHER INFORMATION: primer

<400> SEQUENCE: 386
ggaaguaucg caccacauu                                               19

<210> SEQ ID NO 387
<211> LENGTH: 19
<212> TYPE: RNA
<213> ORGANISM: Artificial Sequence
<220> FEATURE:
<223> OTHER INFORMATION: primer

<400> SEQUENCE: 387
aauguggugc gauacuucc                                               19

<210> SEQ ID NO 388
<211> LENGTH: 23
<212> TYPE: DNA
<213> ORGANISM: Lygus hesperus

<400> SEQUENCE: 388
aaatcaagga caatgtggta gct                                          23

<210> SEQ ID NO 389
<211> LENGTH: 19
<212> TYPE: RNA
<213> ORGANISM: Artificial Sequence
<220> FEATURE:
<223> OTHER INFORMATION: primer

```
<400> SEQUENCE: 389
aucaaggaca auggguag                                                    19

<210> SEQ ID NO 390
<211> LENGTH: 19
<212> TYPE: RNA
<213> ORGANISM: Artificial Sequence
<220> FEATURE:
<223> OTHER INFORMATION: primer

<400> SEQUENCE: 390
cuaccacauu guccuugau                                                   19

<210> SEQ ID NO 391
<211> LENGTH: 23
<212> TYPE: DNA
<213> ORGANISM: Lygus hesperus

<400> SEQUENCE: 391
aaagtgaagg tgaagattgc gag                                              23

<210> SEQ ID NO 392
<211> LENGTH: 19
<212> TYPE: RNA
<213> ORGANISM: Artificial Sequence
<220> FEATURE:
<223> OTHER INFORMATION: primer

<400> SEQUENCE: 392
agugaaggug aagauugcg                                                   19

<210> SEQ ID NO 393
<211> LENGTH: 19
<212> TYPE: RNA
<213> ORGANISM: Artificial Sequence
<220> FEATURE:
<223> OTHER INFORMATION: primer

<400> SEQUENCE: 393
cgcaaucuuc accuucacu                                                   19

<210> SEQ ID NO 394
<211> LENGTH: 23
<212> TYPE: DNA
<213> ORGANISM: Lygus hesperus

<400> SEQUENCE: 394
aagatgttgt gttaggttta ccg                                              23

<210> SEQ ID NO 395
<211> LENGTH: 19
<212> TYPE: RNA
<213> ORGANISM: Artificial Sequence
<220> FEATURE:
<223> OTHER INFORMATION: primer

<400> SEQUENCE: 395
gauguugugu uagguuuac                                                   19

<210> SEQ ID NO 396
<211> LENGTH: 19
<212> TYPE: RNA
<213> ORGANISM: Artificial Sequence
<220> FEATURE:
<223> OTHER INFORMATION: primer
```

```
<400> SEQUENCE: 396
guaaaccuaa cacaacauc                                              19

<210> SEQ ID NO 397
<211> LENGTH: 23
<212> TYPE: DNA
<213> ORGANISM: Lygus hesperus

<400> SEQUENCE: 397
aacaaagtcg attccaccta gag                                         23

<210> SEQ ID NO 398
<211> LENGTH: 19
<212> TYPE: RNA
<213> ORGANISM: Artificial Sequence
<220> FEATURE:
<223> OTHER INFORMATION: primer

<400> SEQUENCE: 398
caaagucgau uccaccuag                                              19

<210> SEQ ID NO 399
<211> LENGTH: 19
<212> TYPE: RNA
<213> ORGANISM: Artificial Sequence
<220> FEATURE:
<223> OTHER INFORMATION: primer

<400> SEQUENCE: 399
cuagguggaa ucgacuuug                                              19

<210> SEQ ID NO 400
<211> LENGTH: 23
<212> TYPE: DNA
<213> ORGANISM: Lygus hesperus

<400> SEQUENCE: 400
aactttggtc ctggtttgga tag                                         23

<210> SEQ ID NO 401
<211> LENGTH: 19
<212> TYPE: RNA
<213> ORGANISM: Artificial Sequence
<220> FEATURE:
<223> OTHER INFORMATION: primer

<400> SEQUENCE: 401
cuuugguccu gguuuggau                                              19

<210> SEQ ID NO 402
<211> LENGTH: 19
<212> TYPE: RNA
<213> ORGANISM: Artificial Sequence
<220> FEATURE:
<223> OTHER INFORMATION: primer

<400> SEQUENCE: 402
auccaaacca ggaccaaag                                              19

<210> SEQ ID NO 403
<211> LENGTH: 23
<212> TYPE: DNA
<213> ORGANISM: Lygus hesperus
```

```
<400> SEQUENCE: 403
aaggcgtgta atctctcaag caa                                         23

<210> SEQ ID NO 404
<211> LENGTH: 19
<212> TYPE: RNA
<213> ORGANISM: Artificial Sequence
<220> FEATURE:
<223> OTHER INFORMATION: primer

<400> SEQUENCE: 404
ggcguguaau cucucaagc                                              19

<210> SEQ ID NO 405
<211> LENGTH: 19
<212> TYPE: RNA
<213> ORGANISM: Artificial Sequence
<220> FEATURE:
<223> OTHER INFORMATION: primer

<400> SEQUENCE: 405
gcuugagaga uuacacgcc                                              19

<210> SEQ ID NO 406
<211> LENGTH: 23
<212> TYPE: DNA
<213> ORGANISM: Lygus hesperus

<400> SEQUENCE: 406
aattcgcggt caactttatc tct                                         23

<210> SEQ ID NO 407
<211> LENGTH: 19
<212> TYPE: RNA
<213> ORGANISM: Artificial Sequence
<220> FEATURE:
<223> OTHER INFORMATION: primer

<400> SEQUENCE: 407
uucgcgguca acuuuaucu                                              19

<210> SEQ ID NO 408
<211> LENGTH: 19
<212> TYPE: RNA
<213> ORGANISM: Artificial Sequence
<220> FEATURE:
<223> OTHER INFORMATION: primer

<400> SEQUENCE: 408
agauaaaguu gaccgcgaa                                              19
```